US007541433B2

(12) United States Patent
Matz et al.

(10) Patent No.: US 7,541,433 B2

(45) Date of Patent: Jun. 2, 2009

(54) FLUORESCENT AND COLORED PROTEINS, AND POLYNUCLEOTIDES THAT ENCODE THESE PROTEINS

(75) Inventors: Mikhail Vladimirovitch Matz, Palm Coast, FL (US); Ilya Vladimirovitch Kelmanson, Moscow (RU); Ella A. Meleshkevitch, Palm Coast, FL (US); Anya Salih, Sydney (AU)

(73) Assignees: University of Florida Research Foundation, Inc., Gainesville, FL (US); University of Sydney, Sydney (AU)

( * ) Notice: Subject to any disclaimer, the term of this patent is extended or adjusted under 35 U.S.C. 154(b) by 0 days.

(21) Appl. No.: 11/637,340

(22) Filed: Dec. 12, 2006

(65) Prior Publication Data

US 2007/0122851 A1 May 31, 2007

Related U.S. Application Data

(63) Continuation of application No. 10/851,636, filed on May 20, 2004, now Pat. No. 7,160,698.

(60) Provisional application No. 60/472,196, filed on May 20, 2003.

(51) Int. Cl.
*C07K 14/00* (2006.01)

(52) U.S. Cl. ........................ 530/350; 530/300; 435/7.1

(58) Field of Classification Search ...................... None
See application file for complete search history.

(56) References Cited

U.S. PATENT DOCUMENTS 5,268,463 A 12/1993 Jefferson
5,491,084 A 2/1996 Chalfie et al.
5,639,663 A 6/1997 Crosby et al.
5,804,387 A 9/1998 Cormack et al.
5,874,304 A 2/1999 Zolotukhin et al.
5,919,445 A 7/1999 Chao
5,958,713 A 9/1999 Thastrup et al.
5,968,738 A 10/1999 Anderson et al.
5,968,750 A 10/1999 Zolotukhin et al.
5,976,796 A 11/1999 Szalay et al.
5,985,577 A 11/1999 Bulinski et al.
6,020,192 A 2/2000 Muzyczka et al.
6,066,476 A 5/2000 Tsien et al.
6,455,759 B1 9/2002 Vierstra et al.
7,090,976 B2 * 8/2006 Anderson et al. .............. 435/6
2003/0219717 A1 11/2003 Dahl et al.

FOREIGN PATENT DOCUMENTS

DE 197 18 640 5/1997
WO WO 99/49019 9/1999
WO WO 00/46233 8/2000

OTHER PUBLICATIONS

Wells, Biochemistry, vol. 29, pp. 8509-8517, 1990.*
Seffernick et al. (J. Bacteriology, vol. 183, pp. 2405-2410, 2001.*
Anderluh G. et al., "Cloning, Sequencing, and Expression of Equinatoxin II," *Biochemical and Biophysical Research Communications*, 1996, vol. 220, pp. 437-442.
Ando, R. et al., "An Optical Marker Based on the UV-Induced Green-to-Red Photoconversion of a Fluorescent Protein," *Proceedings of the National Academy of Sciences*, 2002, vol. 99, No. 20, pp. 12651-12656.
Chudakov D. M. et al., "Kindling Fluorescent Proteins for Precise in vivo Photolabeling," *Nature Biotechnology*, 2003, vol. 21, pp. 191-194.
Eichinger L. et al., "Dictyostelium as Model System for Studies of the Actin Cytoskeleton by Molecular Genetics," *Microscopy Research and Technique*, 1999, vol. 47, pp. 124-134.
Falk M. M. et al., "High Resolution, Fluorescent Deconvolution Microscopy and Tagging With the Autofluorescent Tracers CFP, GFP, and YFP to Study the Structural Composition of Gap Junctions in Living Cells," *Microscopy Research and Technique*, 2001, vol. 52, pp. 251-262.
Fradkov A. F. et al., "Novel Fluorescent Protein From Discosoma Coral and Its Mutants Possesses a Unique Far-Red Fluorescent," *FEBS Letters*, 2000, vol. 479, pp. 127-130.
Gurskaya N. G. et al., "Color Transitions in Coral's Fluorescent Proteins by Site-Directed Mutagenesis," *BMC Biochemistry*, 2001, vol. 2, p. 6.
Gurskaya N. G. et al., "GFP-like Chromosomes as a Source of Far-Red Fluorescent Proteins," *FEBS Letters*, 2001, vol. 507, pp. 16-20.
Hanson M. R. et al., "GFP Imaging: Methodology and Application to Investigate Cellular Compartmentation in plants," *Journal of Experimental Botany*, 2001, vol. 52, pp. 529-539.
Hillisch A. et al., "Recent Advances in FRET: Distance Determination in Protein-DNA Complexes," *Current Opinion in Structural Biology*, 2001, vol. 11, pp. 201-207.
Houtsmuller A. B. et al., "Macromolecular Dynamics in Living Cell Nuclei Revealed by Fluorescent Redistribution After Photobleaching," *Histochem Cell Biol*, 2001, vol. 115, pp. 13-21.
Kallal L. et al., "Using Green Fluorescent Proteins to Study G-Protein-Coupled Receptor Localization and Trafficking," *Trends Pharmacol Sci*, vol. 21, pp. 175-180.
Labas Y. A. et al., "Diversity and Evolution of the Green Fluorescent Protein Family," *Proc Natl Acad Sci USA*, 2002, vol. 99, pp. 4256-4261.
Laird D. W. et al., "Comparative Analysis and Application of Fluorescent Protein-Tagged Connexins," *Microscopy and Research Technique*, 2001, vol. 52, pp. 263-272.

(Continued)

*Primary Examiner*—Hope A Robinson
(74) *Attorney, Agent, or Firm*—Saliwanchik, Lloyd & Saliwanchik

(57) ABSTRACT

The subject invention provides new fluorescent and/or colored proteins, and polynucleotide sequences that encode these proteins. The subject invention further provides materials and methods useful for expressing these detectable proteins in biological systems.

4 Claims, 15 Drawing Sheets
(2 of 15 Drawing Sheet(s) Filed in Color)

OTHER PUBLICATIONS

Lukyanov K. A. et al., "Natural Animal Coloration Can Be Determined by a Nonfluorescent Green Fluorescent Protein Homolog," *J Biol Chemistry*, 2000, vol. 275, No. 34, pp. 25879-25882.

Macek, P. et al., "Intrinsic Tryptophan Fluorescence of Equinatoxin II, a Pore-Forming Polypeptide From the Sea Anemone *Actinia equina* L, Monitors Its Interaction With Lipid Membranes," *European Journal of Biochemistry*, 1995, vol. 234, pp. 329-335.

Martynov V. I. et al., "Alternative Cyclization in GFP-like Proteins Family," *J Biol Chem*, 2001, vol. 276, pp. 21012-21016.

Matz M. V. et al, "Family of the Green Fluorescent Protein: Journey to the End of the Rainbow," *Bioessays*, 2002, vol. 24, pp. 953-959.

Matz M. V. et al., "Fluorescent Proteins From Nonbioluminescent Anthozoa Species," *Nature Biotechnol*, 1999, vol. 17, pp. 969-973.

Patterson G. H. et al, "A Photoactivatable GFP for Selective Photolabeling of Proteins and Cells," *Science*, 2002, vol. 297, pp. 1873-1877.

Pollok B. A. et al., "Using GFP in FRET-based Applications," *Cell Biology*, 1999, vol. 9, pp. 57-60.

Reits E. et al., "From Fixed to FRAP: Measuring Protein Mobility and Activity in Living Cells," *Nature Cell Biology*, 2001, vol. 3, pp. E145-147.

Seffernick J. et al., "Melamine Deaminase and Atrazine Chlorohydrolase: 98 Percent Identical but Functionally Different," *Journal of Bacteriology*, Apr. 2001, vol. 183, No. 8, pp. 2405-2410.

Terskikh A. et al., "Fluorescent Timer: Protein That Changes Color With Time," *Science*, 2000, vol. 290, pp. 1585-1588.

Tsien R. Y., "The Green Fluorescent Protein," *Annu Rev Biochem*, 1998, vol. 67, pp. 509-544.

Tsien R. Y., "Rosy Dawn for Fluorescent Proteins," *Nat Biotech*, 1999, vol. 17, pp. 956-957.

Verkhusha V. V., et al., "An Enhanced Mutant of Red Fluorescent Protein DsRed for Developmental Timer of Neural Fiber Bundle Formation," *Journal of Biological Chemistry*, 2001, vol. 276, pp. 29621-29624.

Ward W. W. et al., "An Energy Transfer Protein in Coelenterate Bioluminescence," *J Biol Chem*, 1979, vol. 254, pp. 781-788.

Wells, J. A., "Additivity of Mutational Effects in Proteins," *Biochemistry*, Sep. 18, 1990, vol. 29, No. 37, pp. 8509-8517.

Yanushevich Y. G. et al., "A Strategy for the Generation of Non-Aggregating Mutants of Anthozoa Fluorescent Proteins," *FEBS Letters*, 2002, vol. 511, pp. 11-14.

Yarbrough D. et al., "Refined Crystal Structure of DsRed, a Red Fluorescent Protein From Coral, at 2.0-A Resolution," *Proc Natl Acad Sci USA*, 2001, vol. 98, pp. 462-467.

* cited by examiner

FLUORESCENT AND COLORED PROTEINS, AND POLYNUCLEOTIDES THAT ENCODE THESE PROTEINS

CROSS-REFERENCE TO A RELATED APPLICATION

This application is a continuation application of application Ser. No. 10/851,636, filed May 20, 2004, now U.S. Pat. No. 7,160,698; which claims the benefit of U.S. provisional patent application Ser. No. 60/472,196, filed May 20, 2003, in it's entirety.

GOVERNMENT SUPPORT

The subject matter of this application has been supported in part by U.S. Government Support under NIH RO1 GM066243-01. Accordingly, the U.S. Government has certain rights in this invention.

FIELD OF THE INVENTION

The present invention relates to novel fluorescent and colored proteins, and their use. These materials and methods are particularly advantageous for labeling and detection technology. Specifically, exemplified are novel colored and/or fluorescent proteins, and mutants thereof, isolated from marine organisms. These new proteins offer a wider array of colors and biochemical features compared to existing wild-type green fluorescent protein (GFP) or its modified variants utilized in current labeling and detection technology.

BACKGROUND OF THE INVENTION

Genetic markers are important for monitoring gene expression and tracking movement of proteins in cells. Markers have been extensively used for monitoring biological activity of genetic elements such as promoters, enhancers and terminators, and other aspects of gene regulation in numerous biological systems. Over the years numerous marker genes have been developed and utilized widely in molecular and genetic studies aimed at the identification, isolation and characterization of genetic regulatory elements and genes, and the development of gene transfer techniques.

In general, markers can be grouped into selectable markers and reporter markers. Selectable markers are typically enzymes with catalytic capability to convert chemical substrates usually harmful to host cells into non-toxic products, thus providing transformed host cells a conditionally selectable growth advantage under selective environment and allowing the recovery of stable transformants after transformation. A number of commonly used selectable markers include those that confer resistance characteristics to antibiotics (Gritz and Davies 1983; Bevan et al., 1983) and herbicides (De Block et al., 1987), and those with enzymatic activity to detoxify metabolic compounds that can adversely affect cell growth (Joersbo and Okkels 1996).

Reporter markers are compounds that provide biochemically assayable or identifiable activities. Reporter markers have been widely used in studies to reveal biological functions and modes of action of genetic elements such as promoters, enhancers, terminators, and regulatory proteins including signal peptides, transcription factors and related gene products. Over the years, several reporter markers have been developed for use in both prokaryotic and eukaryotic systems, including β-galactosidase (LacZ) (Stanley and Luzio 1984), β-glucuronidase (GUS) (Jefferson et al., 1987; U.S. Pat. No. 5,268,463), chloramphenicol acetyltransferase (CAT) (Gorman et al., 1982), green fluorescent protein (GFP) (Prasher et al., 1992; U.S. Pat. No. 5,491,084) and luciferase (Luc) (Ow et al., 1986).

Among reporter markers, GUS offers a sensitive and versatile reporting capability for gene expression in plants. β-glucuronidase or GUS, encoded by the uidA gene from *Escherichia coli*, catalyzes the conversion of several colorigenic and fluorogenic glucorogenic substrates such as p-nitrophenyl β-D-glucuronide and 4-methylumbelliferyl β-D-glucuronide into easily detectable products. GUS activity can be measured by highly sensitive colorimetric and fluorimetric methods (Jefferson et al., 1987). However, the GUS assay often requires total destruction of the sample tissues or exposure of sample tissues to phytotoxic chemical substrates. This prevents repeated use of the same sample tissue for continuous expression analysis and precludes the recovery of transformants from analyzed materials.

Recently, GFP isolated from the Pacific Northwest jellyfish (*Aequorea victoria*) has become an important reporter marker for non-destructive analysis of gene expression. GFP fluoresces in vivo by receiving light energy without the involvement of any chemical substrates. Thus, GFP is especially suitable for real time and continuous monitoring of temporal and spatial control of gene expression and protein activities without any physical damage to assay samples.

The gene for GFP has been cloned and used as a reporter gene, which can be expressed as a functional transgene in living organisms, marking the organisms with fluorescent color and thus allowing detection of those organisms. Accordingly, GFP has become a versatile fluorescent marker for monitoring a variety of physiological processes, visualizing protein localization and detecting the expression of transferred genes in various living systems, including bacteria, fungi, and mammalian tissues.

This in vivo labeling and detection technology was originally based on a single fluorescent protein: the green fluorescent protein from *Aequorea victoria*. Numerous modifications have been made to alter the spectral properties of GFP to provide for significant enhancement in fluorescence intensity (Prasher et al., 1992; Cubitt et al., 1995, Heim et al., 1994, 1995; Cormack et al., 1996; U.S. Pat. No. 5,804,387). In addition, GFP genes have been modified to contain more silent base mutations that correspond to codon-usage preferences in order to improve its expression efficacy, making it a reporter gene in both animal and plant systems (U.S. Pat. Nos. 5,874,304; 5,968,750; and 6,020,192).

In addition to GFP, there are now a number of other fluorescent proteins, substantially different from GFP, which are being developed into biotechnology tools. Most prominent of these proteins is the red fluorescent protein DsRed. See, for example, Labas, Y. A., N. G. Gurskaya, Y. G. Yanushevich, A. F. Fradkov, K. A. Lukyanov, S. A. Lukyanov and M. V. Matz. (2002) "Diversity and evolution of the green fluorescent protein family" *Proc Natl Acad Sci USA* 99:4256-4261 and Matz, M. V., K. A. Lukyanov and S. A. Lukyanov (2002) "Family of the green fluorescent protein: journey to the end of the rainbow" *Bioessays* 24: 953-959.

Labeling technologies based on GFP and related proteins have become indispensable in such areas as basic biomedical research, cell and molecular biology, transgenic research and drug discovery. The number of PubMed records containing the phrase "green fluorescent protein" exceeds 5500 only within the last three years. Demand for labeling and detection based on the fluorescent protein technology is large and steady.

Currently, there are very few known natural pigments essentially encoded by a single gene, wherein both the substrate for pigment biosynthesis and the necessary catalytic moieties are provided within a single polypeptide chain. The limited availability of fluorescent marker proteins makes the current technology based on fluorescent proteins very expensive, rendering it unaffordable and inaccessible to many mid-size (or smaller) companies that are interested in using the technology. Therefore, there is a need for less expensive, readily available fluorescent and/or colored materials.

BRIEF SUMMARY OF THE INVENTION

The patent or application file contains at least one drawing executed in color. Copies of this patent or patent application with color drawing(s) will be provided by the Office upon request and payment of the necessary fees.

The subject invention provides new fluorescent and/or colored proteins, and polynucleotide sequences that encode these proteins. The subject invention further provides materials and methods useful for expressing these detectable proteins in biological systems.

In specific embodiments, the subject invention provides a red fluorescent protein from *Scolymia cubensis* scubRFP, featuring rapid conversion from immature green to mature red form under UV-A light; and three fluorescent proteins from *Montastraea cavernosa*, namely g5.2 (cyan), mc6 (green) and R7 (green) proteins. The invention also includes proteins substantially similar to, or mutants or variants of, the exemplified proteins.

Another aspect of the subject invention pertains to polynucleotide sequences that encode the detectable proteins of the present invention. In one embodiment, the present invention provides polynucleotide constructs comprising cDNA encoding novel colored and/or fluorescent proteins and mutants thereof.

The subject invention also provides proteins from *Acropora* ("staghorn corals") and *Agarica fragilis* ("fragile saucer coral"), as well as polynucleotides encoding these proteins.

In one embodiment, the invention provides nucleotide sequences of the inserts in pGEM-T vector (Promega), the conceptual translations of these inserts, and special properties of purified protein products.

The proteins and polynucleotides of the present invention can be used as described herein as colored and/or fluorescent (detectable) labels in a variety of ways, including but not limited to, as reporter genes for monitoring gene expression in living organisms, as protein tags for tracing the location of proteins within living cells and organisms, as reporter molecules for engineering various protein-based biosensors, and as genetically encoded pigments for modifying color and/or fluorescence of living organisms or their parts.

In a specific embodiment, the proteins of the subject invention can be used in molecular fluorescent tagging whereby the coding region of a protein of interest is fused with the coding region for a fluorescent protein of the subject invention. The product of such a gene shows the functional characteristics of the protein of interest, but bears the fluorescent label allowing tracing its movements.

Advantageously, the present invention provides proteins and polynucleotides to improve on the current technology of labeling and detection by offering a wider choice of colors and biochemical features never before provided by GFP and its modified variants.

BRIEF DESCRIPTION OF THE FIGURES

The patent or application file contains at least one drawing executed in color. Copies of this patent or patent application with color drawing(s) will be provided by the Office upon request and payment of the necessary fee.

FIG. 3A is a graph showing the change in ratio or emission amplitudes of 520 and 575 nm. FIG. 3B graph shows changes in the emission spectra.

BRIEF DESCRIPTION OF THE SEQUENCES

Figure 1:
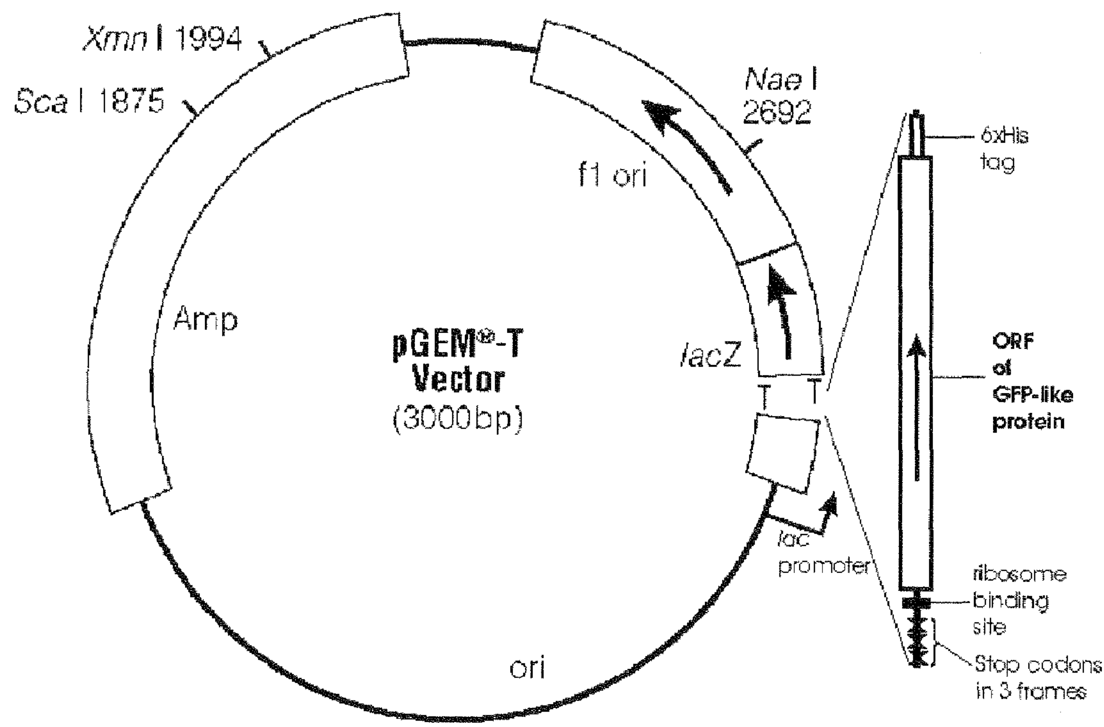
FIG. 1 shows design of bacterial expression constructs for the proteins of interests of the present invention.
Figure 2:
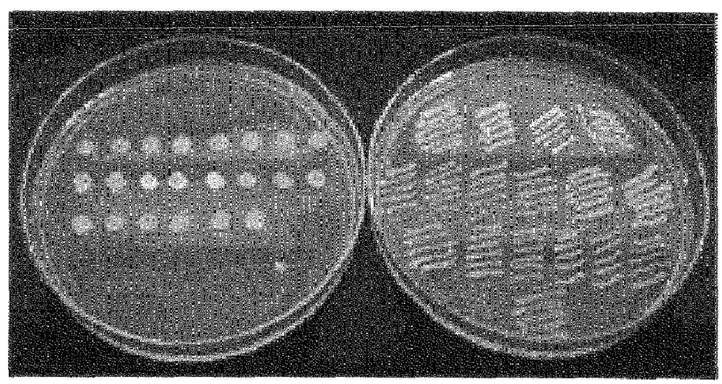
FIG. 2 shows the bacterial colonies expressing genes described in the present invention (cyan, green and red) under UV-A light. The bacterial colonies affected by the expression show red and greenish color and fluorescent appearance. These bacterial colonies are normally non-fluorescent under UV-A light.
Figure 3A:
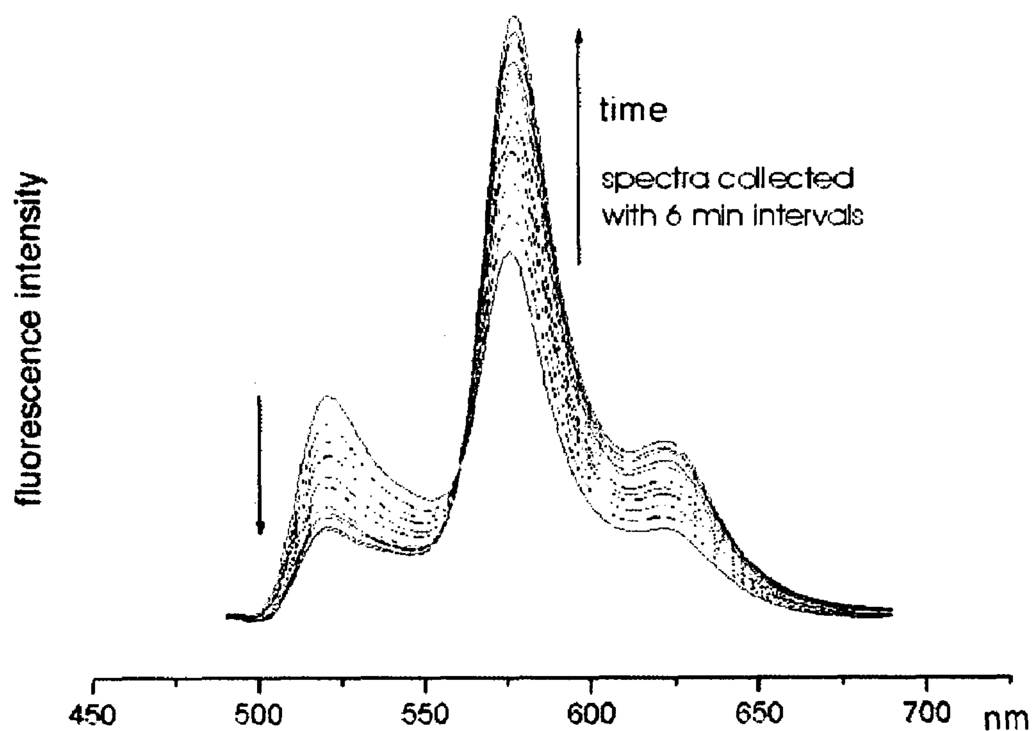
FIG. 3A-3B shows maturation of scubRFP under low-intensity UV-A light, resulting in conversion from a green-emitting form (emission maximum 520 nm) into red-emitting form (emission maximum 575 nm).
Figure 3B:
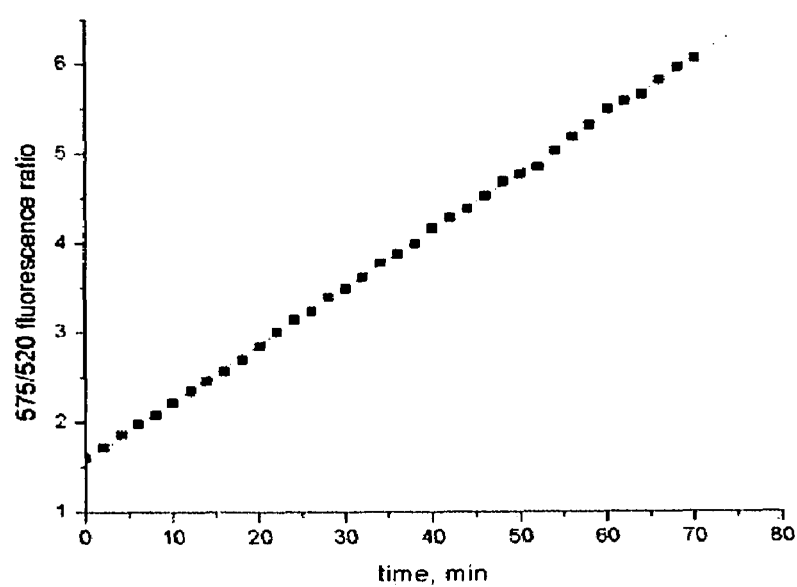
Figure 4:
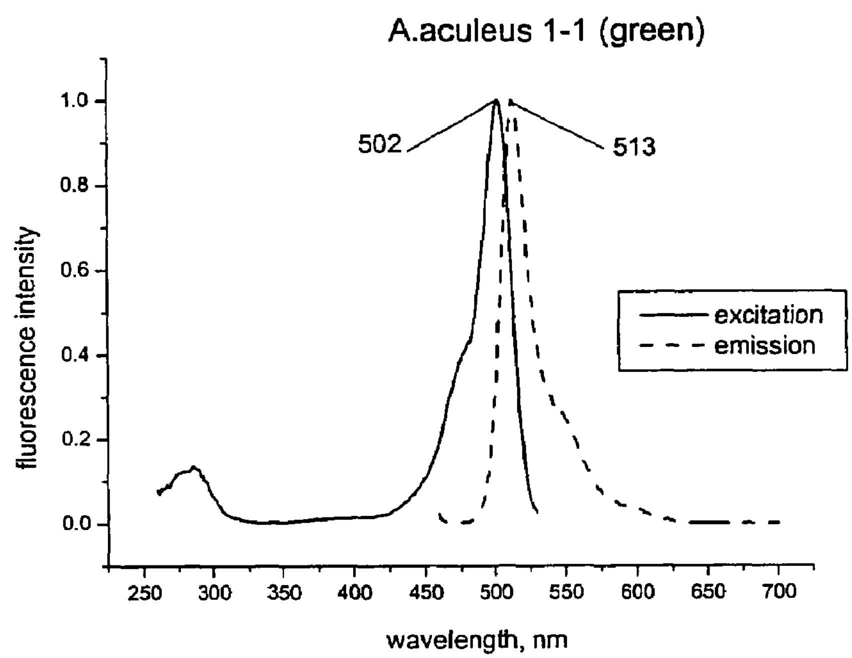
FIG. 4 shows the excitation and emission spectra of *A. aculeus* 1-1 (green).
Figure 5:
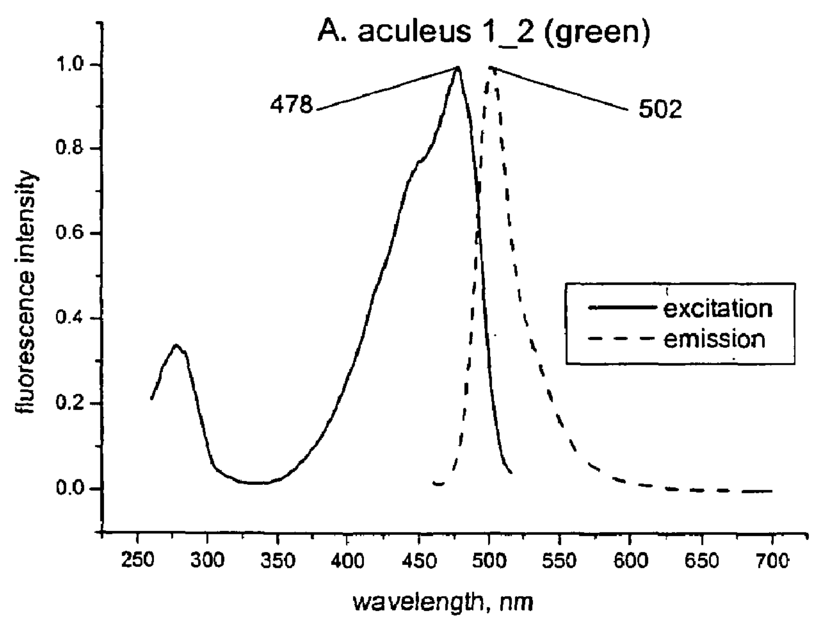
FIG. 5 shows the excitation and emission spectra of *A. aculeus* 1-2 (green).
Figure 6:
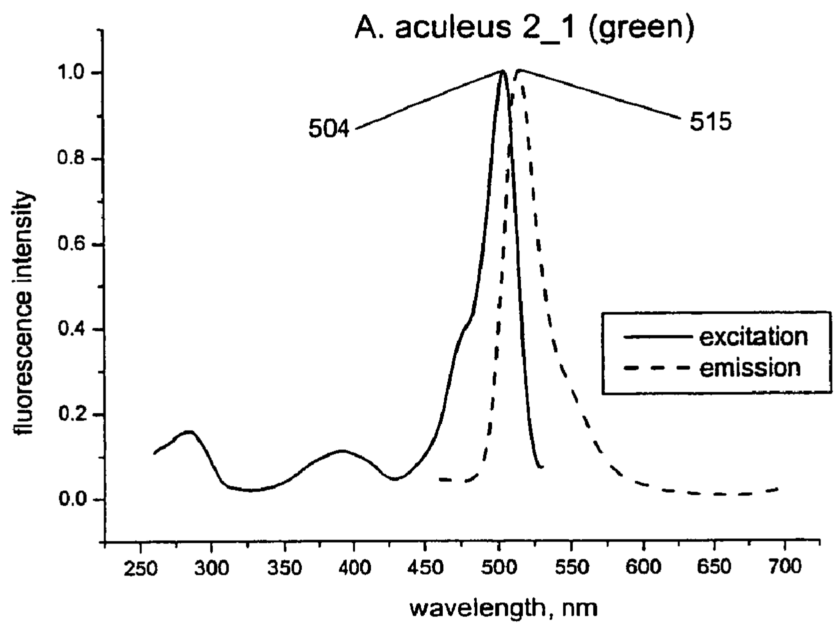
FIG. 6 shows the excitation and emission spectra of *A. aculeus* 2-1 (green).
Figure 7:
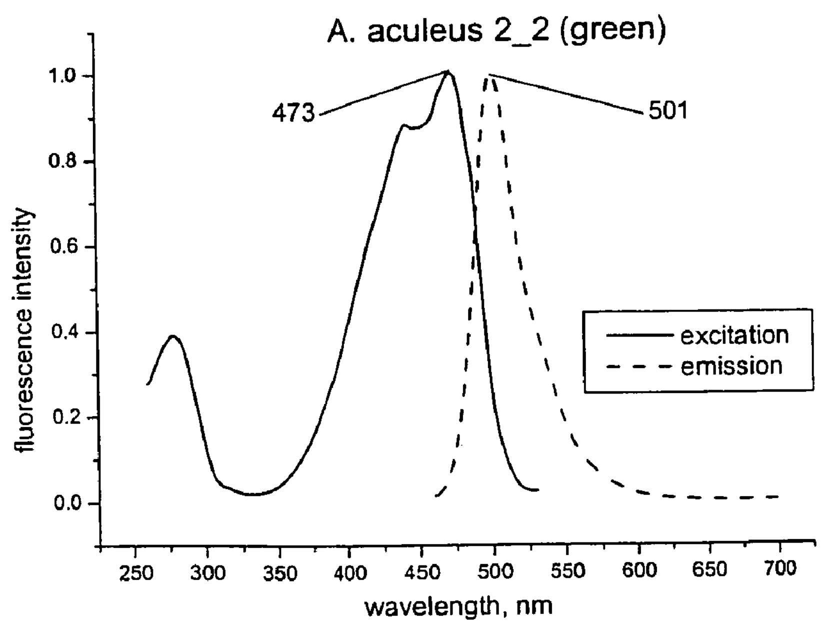
FIG. 7 shows the excitation and emission spectra of *A. aculeus* 2-2 (green).
Figure 8:
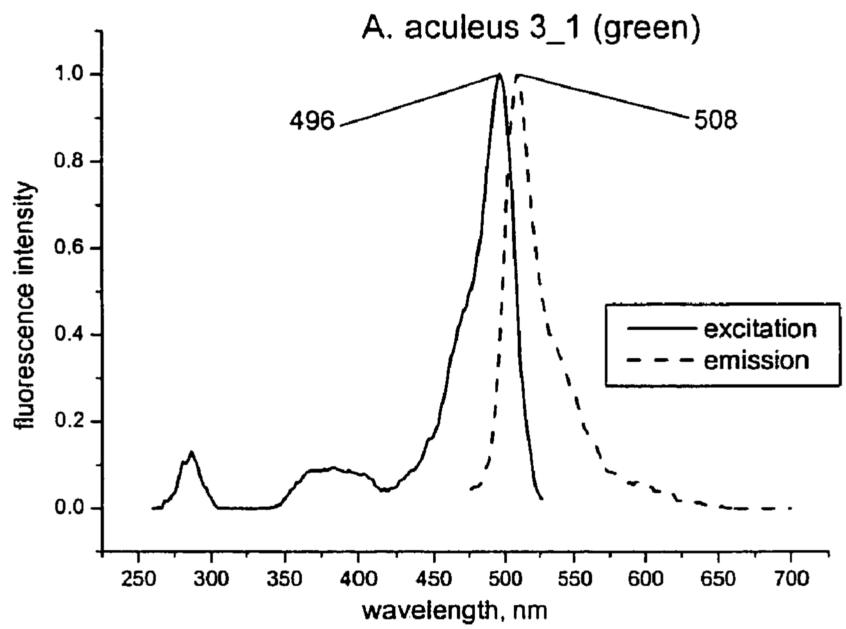
FIG. 8 shows the excitation and emission spectra of *A. aculeus* 3-1 (green).
Figure 9:
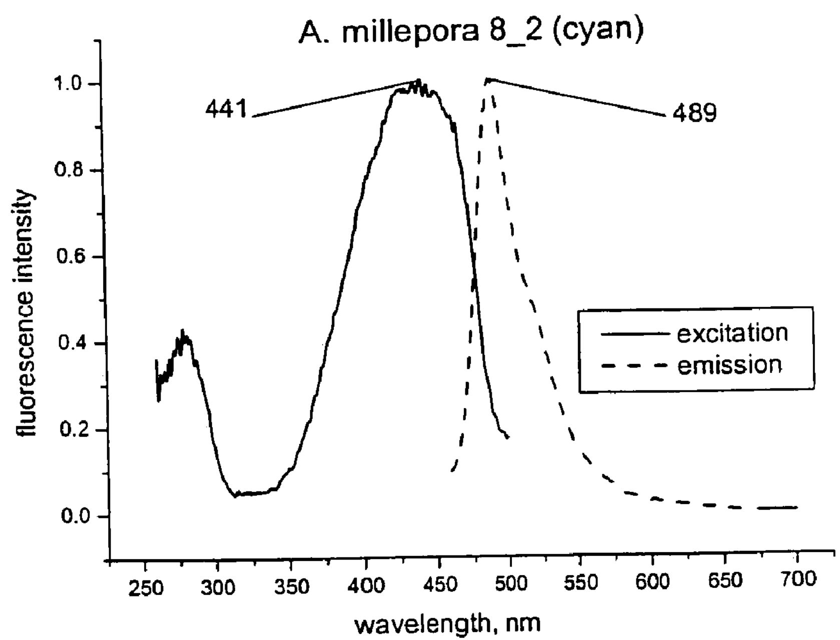
FIG. 9 shows the excitation and emission spectra of *A. millepora* 8-2 (cyan).
Figure 10:
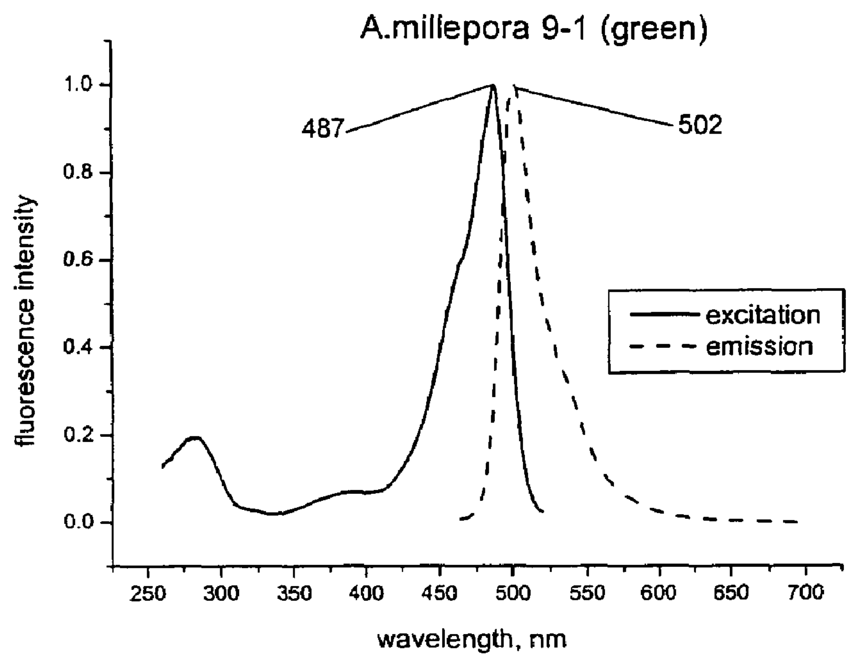
FIG. 10 shows the excitation and emission spectra of *A. millepora* 9-1 (green).
Figure 11:
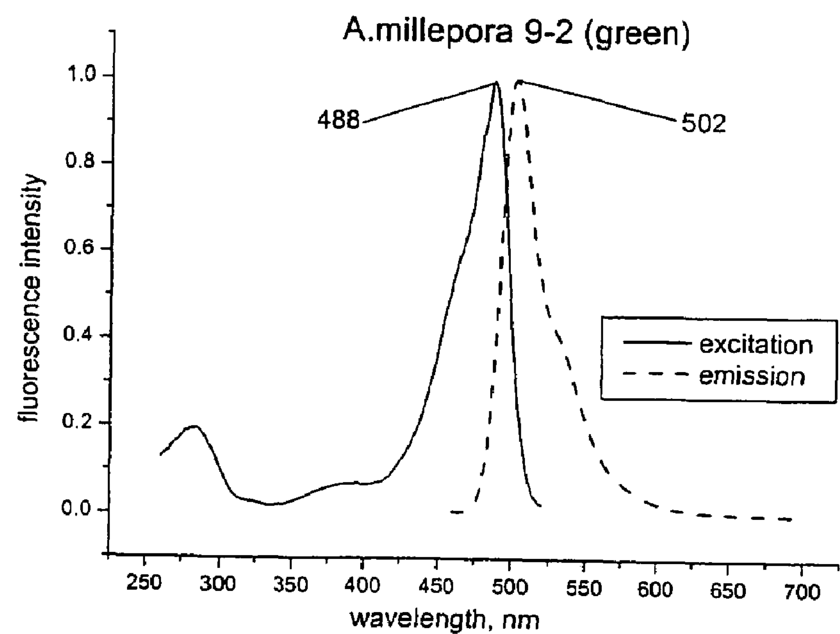
FIG. 11 shows the excitation and emission spectra of *A. millepora* 9-2 (green).
Figure 12:
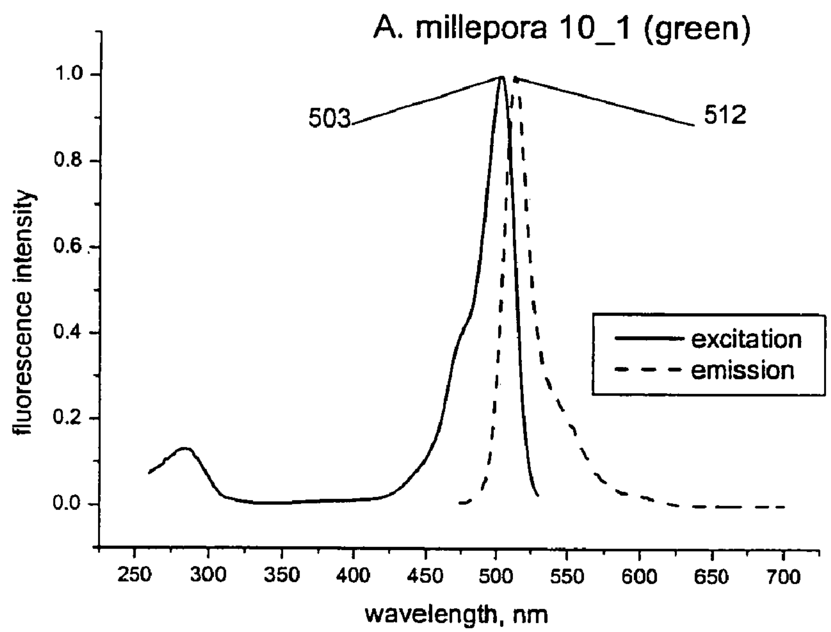
FIG. 12 shows the excitation and emission spectra of *A. millepora* 10-1 (green).
Figure 13:
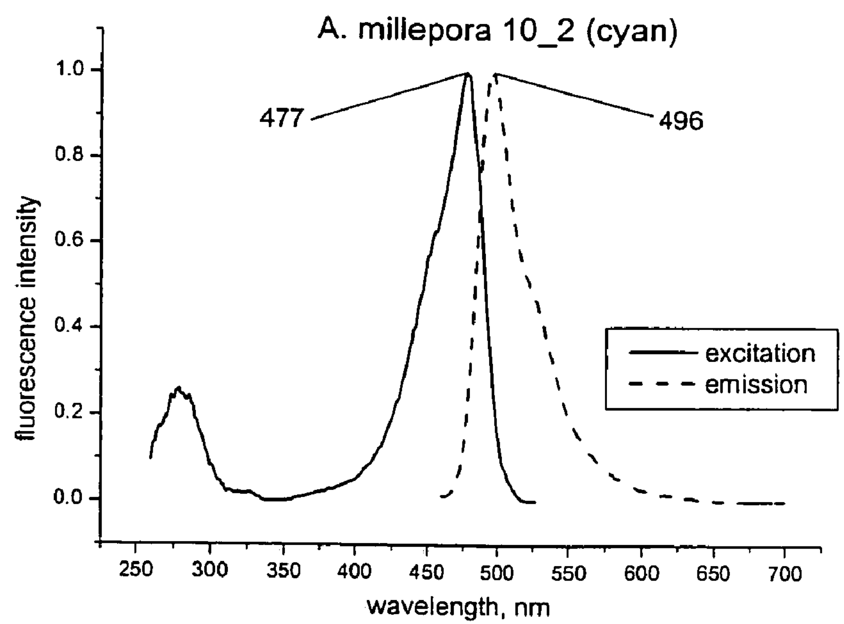
FIG. 13 shows the excitation and emission spectra of *A. millepora* 10-2 (cyan).
Figure 14:
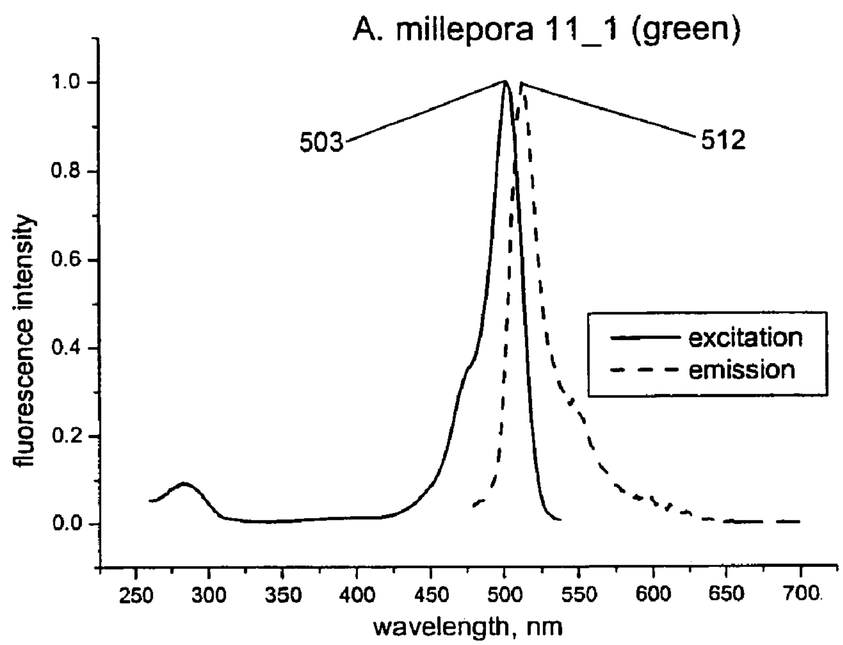
FIG. 14 shows the excitation and emission spectra of *A. millepora* 11-1 (green).
Figure 15:
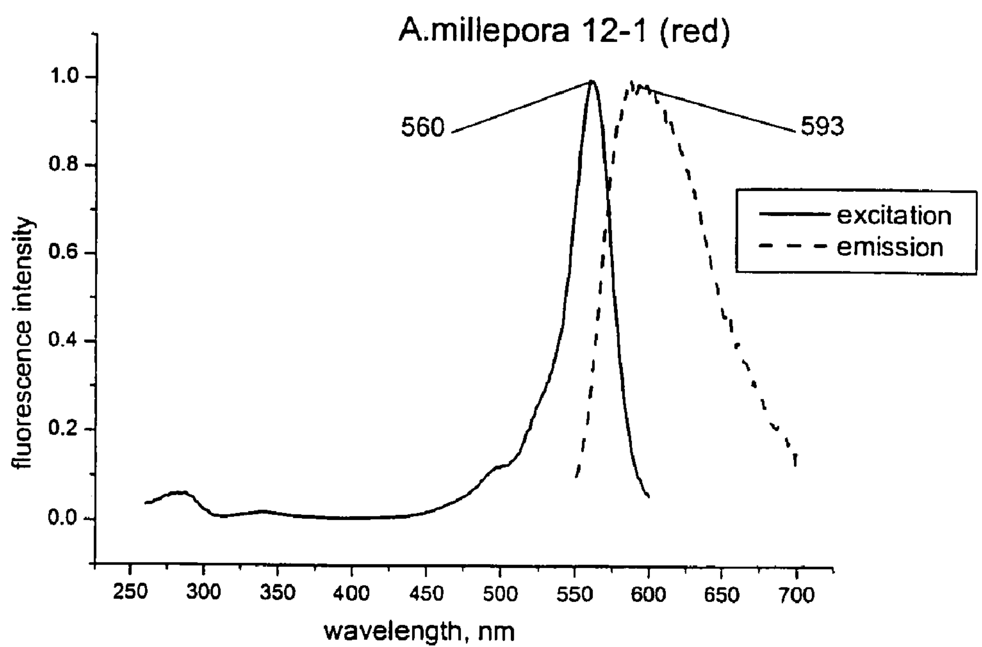
FIG. 15 shows the excitation and emission spectra of *A. millepora* 12-1 (red).
Figure 16:
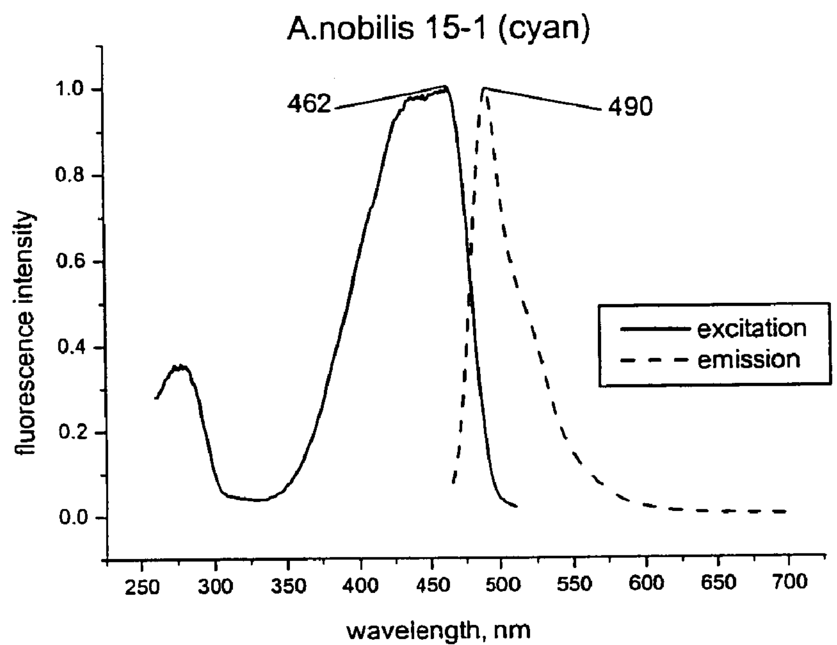
FIG. 16 shows the excitation and emission spectra of *A. nobilis* 15-1 (cyan).
Figure 17:
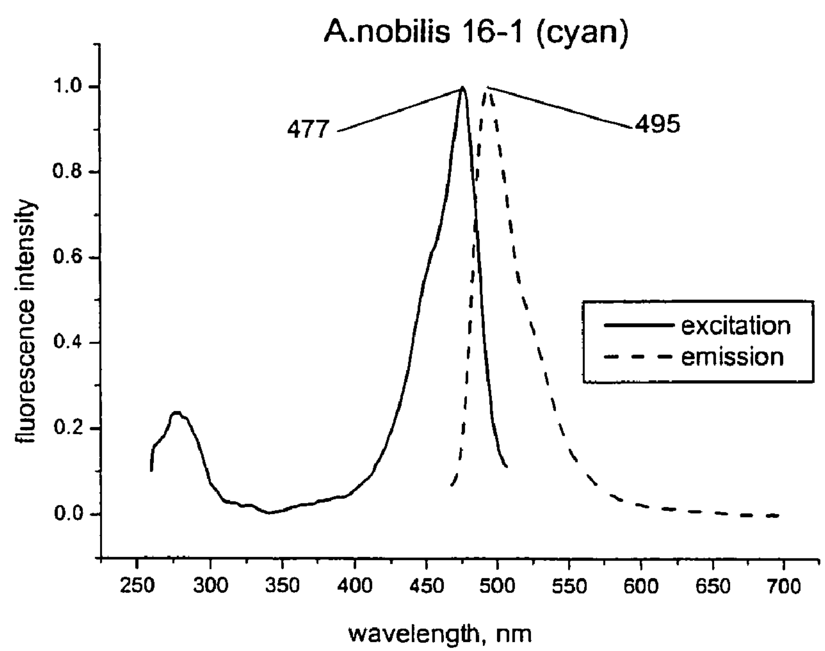
FIG. 17 shows the excitation and emission spectra of *A. nobilis* 16-1 (cyan).
Figure 18:
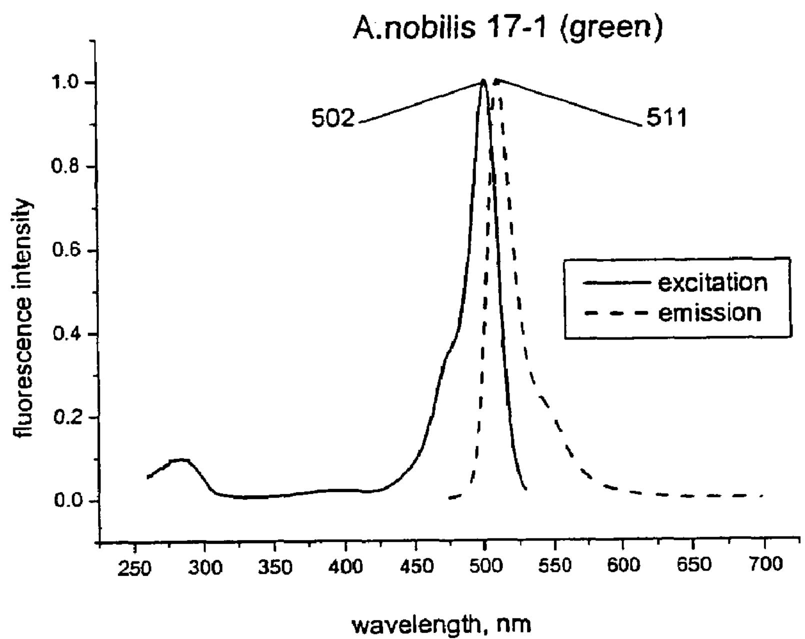
FIG. 18 shows the excitation and emission spectra of *A. nobilis* 17-1 (green).
Figure 19:
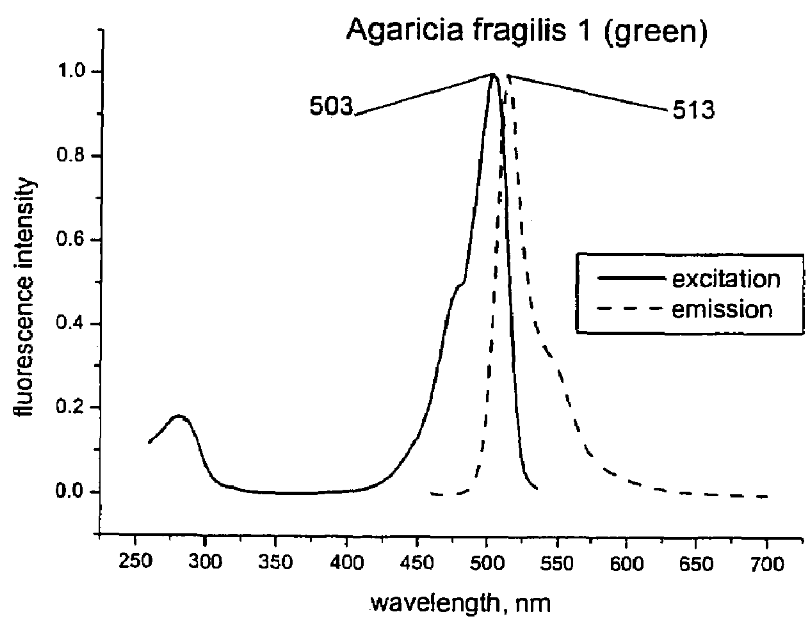
FIG. 19 shows the excitation and emission spectra of *Agaricia fragilis* 1 (green).
Figure 20:
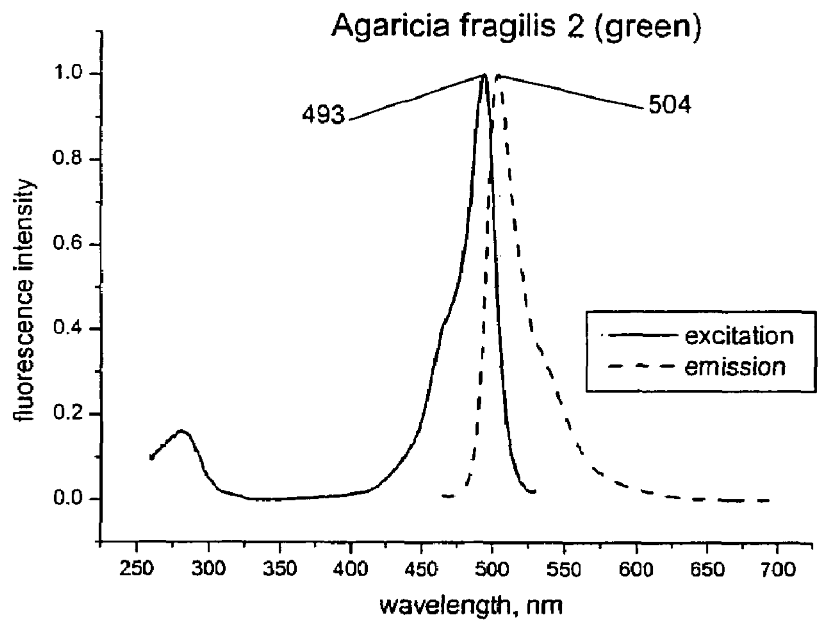
FIG. 20 shows the excitation and emission spectra of *Agaricia fragilis* 2 (green).
Figure 21:
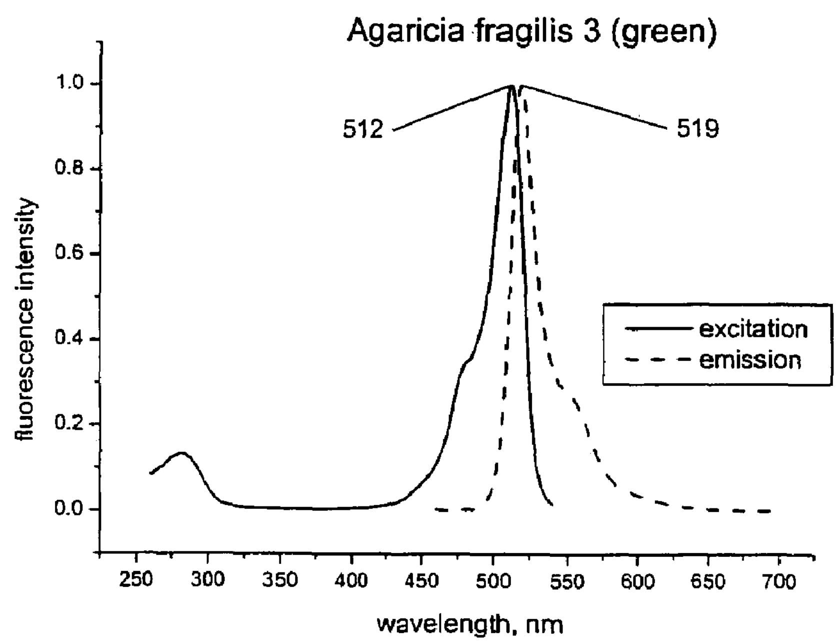
FIG. 21 shows the excitation and emission spectra of *Agaricia fragilis* 3 (green).
Figure 22:
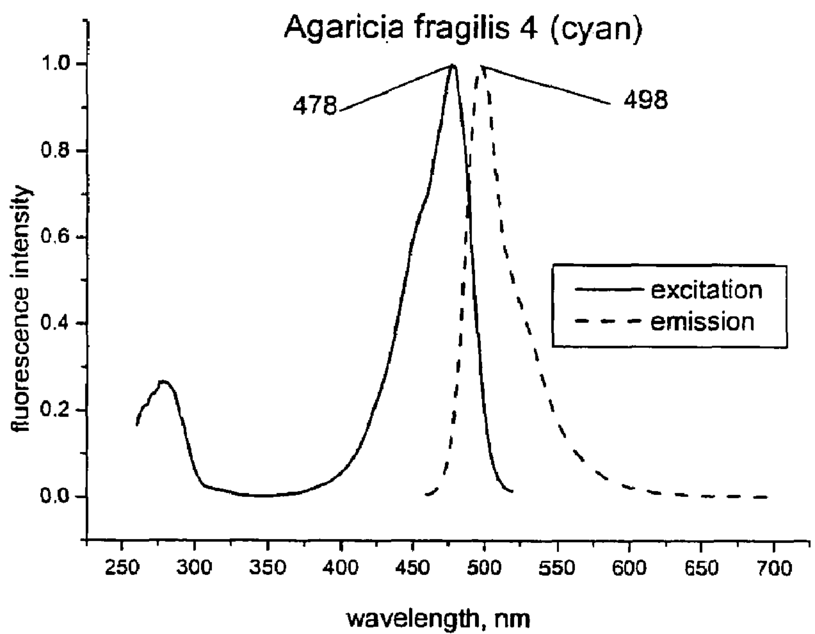
FIG. 22 shows the excitation and emission spectra of *Agaricia fragilis* 4 (cyan).
Figure 23:
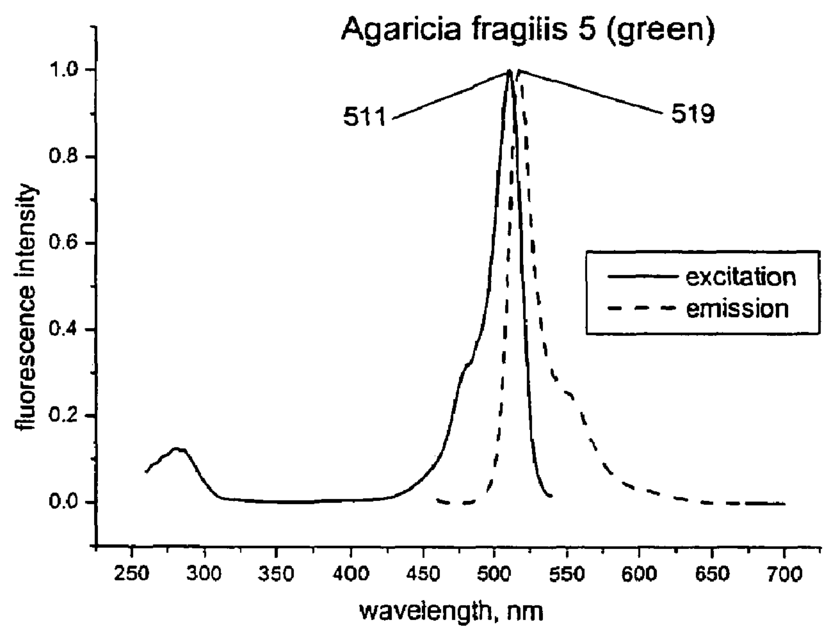
FIG. 23 shows the excitation and emission spectra of *Agaricia fragilis* 5 (green).
Figure 24:
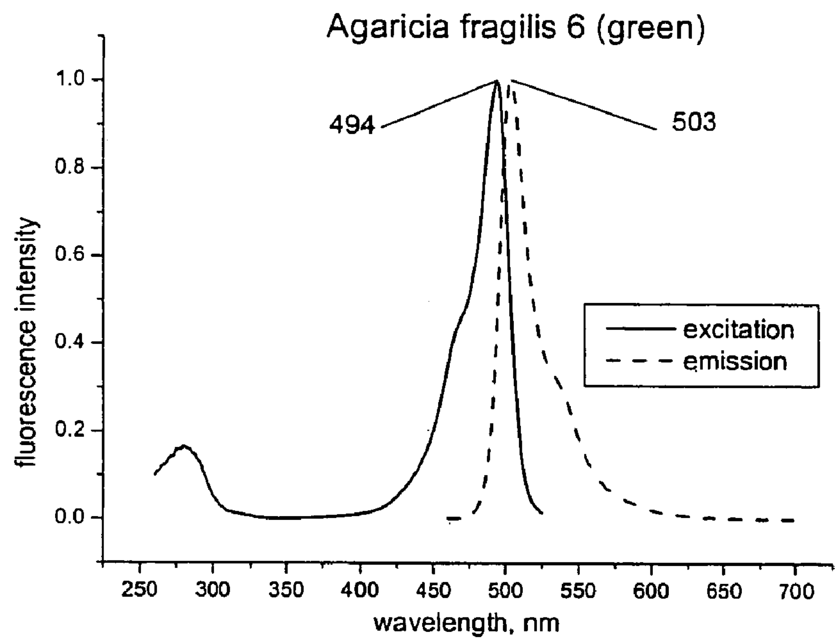
FIG. 24 shows the excitation and emission spectra of *Agaricia fragilis* 6 (green).
Figure 25:
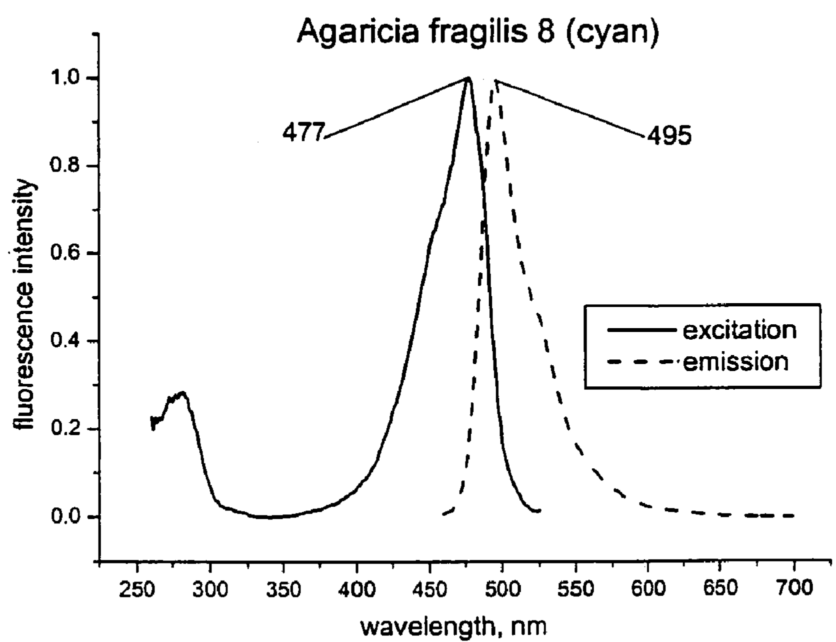
FIG. 25 shows the excitation and emission spectra of *Agaricia fragilis* 8 (cyan).
Figure 26:
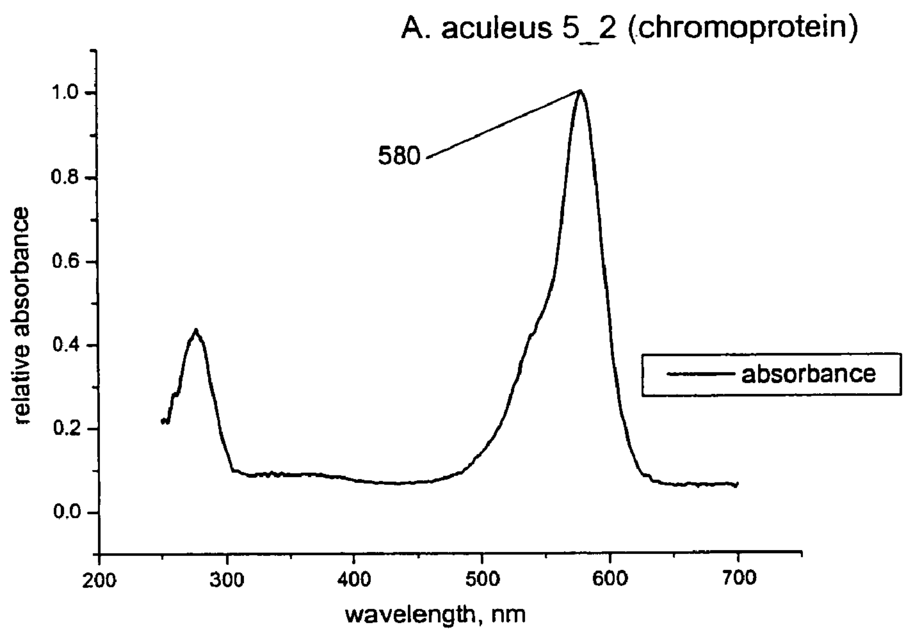
FIG. 26 shows the excitation and emission spectra of *A. aculeus* 5-2 (chromoprotein).
Figure 27:
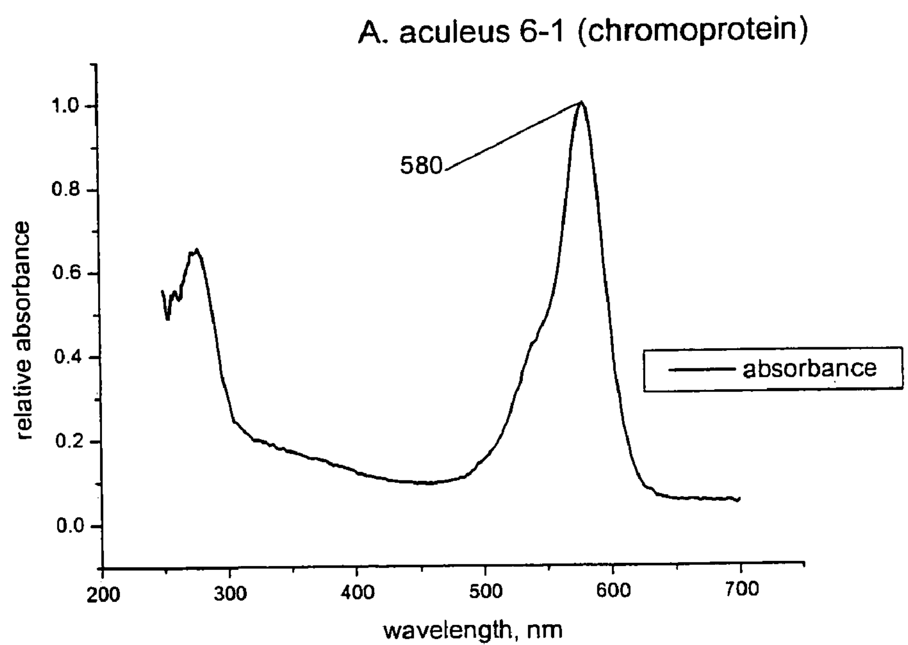
FIG. 27 shows the excitation and emission spectra of *A. aculeus* 6-1 (chromoprotein).
Figure 28:
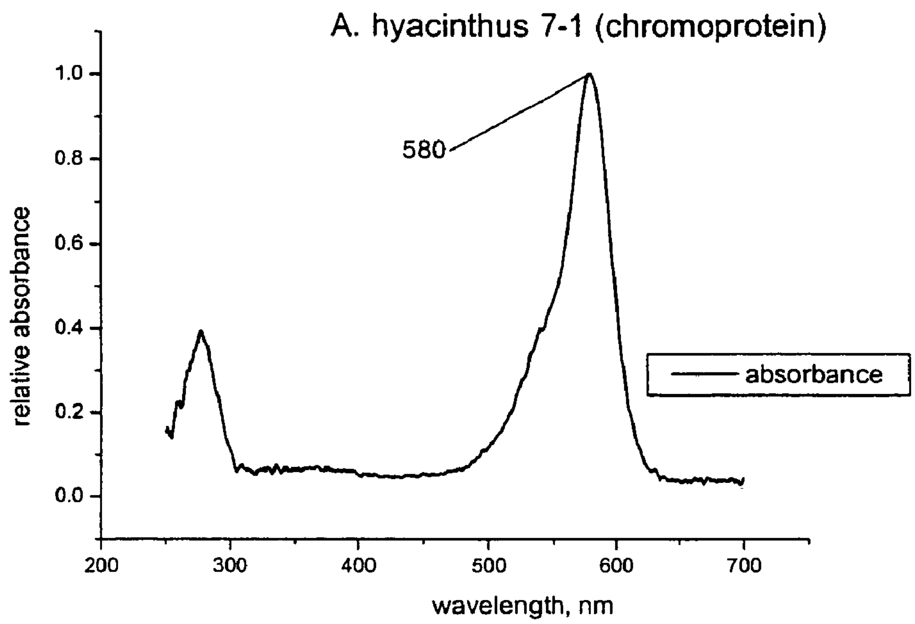
FIG. 28 shows the excitation and emission spectra of *A. hyacinthus* 7-1 (chromoprotein).
Figure 29:
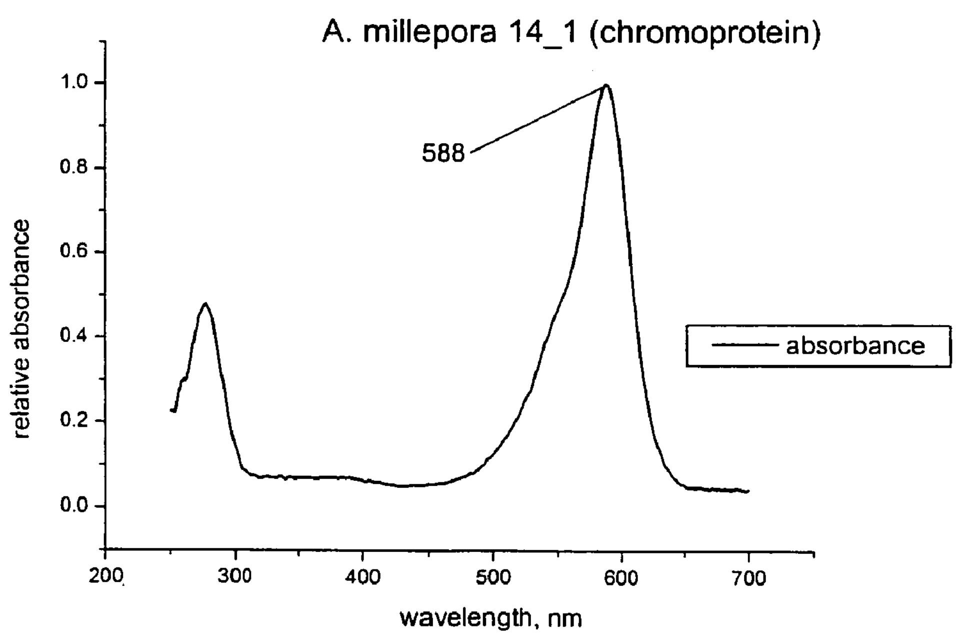
FIG. 29 shows the excitation and emission spectra of *A. millepora* 14-1 (chromoprotein).

SEQ ID NO:1 is the 5' heel of an upstream primer used according to the subject invention.

SEQ ID NO:2 is the 5' heel of a downstream primer used according to the subject invention.

SEQ ID NO:3 is the open reading frame of the cDNA encoding the g5.2 (cyan) protein of interest from *Montastraea cavernosa.*

SEQ ID NO:4 is the open reading frame of the cDNA encoding the mc6 (green) protein of interest from *Montastraea cavernosa.*

SEQ ID NO:5 is the open reading frame of the cDNA encoding the R7 (green) protein of interest from *Montastraea cavernosa.*

SEQ ID NO:6 is the open reading frame of the cDNA encoding the scubRFP protein of interest from *Scolymia cubensis.*

SEQ ID NO:7 is the amino acid sequence encoded by SEQ ID NO:3.

SEQ ID NO:8 is the amino acid sequence encoded by SEQ ID NO:4.

SEQ ID NO:9 is the amino acid sequence encoded by SEQ ID NO:5.

SEQ ID NO:10 is the amino acid sequence encoded by SEQ ID NO:6.

SEQ ID NO:11 is the bacterial expression construct for the g5.2 (cyan) protein of interest from *Montastraea cavernosa.*

SEQ ID NO:12 is the bacterial expression construct for the mc6 (green) protein of interest from *Montastraea cavernosa.*

SEQ ID NO:13 is the bacterial expression construct for the R7 (green) protein of interest from *Montastraea cavernosa.*

SEQ ID NO:14 is the bacterial expression construct for the scubRFP protein of interest from *Scolymia cubensis.*

SEQ ID NO:15 is the amino acid sequence encoded by SEQ ID NO:11.

SEQ ID NO:16 is the amino acid sequence encoded by SEQ ID NO:12.

SEQ ID NO:17 is the amino acid sequence encoded by SEQ ID NO:13.

SEQ ID NO:18 is the amino acid sequence encoded by SEQ ID NO:14.

SEQ ID NO:19 is the nucleotide sequence of an insert in the pGEM-T vector, according to subject invention (*Acropora aculeus* 1-1 in pGEM-T).

SEQ ID NO:20 is the nucleotide sequence of an insert in the pGEM-T vector, according to subject invention (*Acropora aculeus* 1-2 in pGEM-T).

SEQ ID NO:21 is the nucleotide sequence of an insert in the pGEM-T vector, according to subject invention (*Acropora aculeus* 2-1 in gGEM-T).

SEQ ID NO:22 is the nucleotide sequence of an insert in the pGEM-T vector, according to subject invention (*Acropora aculeus* 2-2 in pGEM-T).

SEQ ID NO:23 is the nucleotide sequence of an insert in the pGEM-T vector, according to subject invention (*Acropora aculeus* 3-1 in pGEM-T).

SEQ ID NO:24 is the nucleotide sequence insert of the subject invention (*Acropora aculeus* 5-2 in pGEM-T).

SEQ ID NO:25 is the nucleotide sequence of an insert in the pGEM-T vector, according to subject invention (*Acropora aculeus* 6-1 in pGEM-T).

SEQ ID NO:26 is the nucleotide sequence insert of the subject invention (*Acropora hyacinthus* 7-1 in pGEM-T).

SEQ ID NO:27 is the nucleotide sequence of an insert in the pGEM-T vector, according to subject invention *Acropora millepora* 8-2 in pGEM-T).

SEQ ID NO:28 i is the nucleotide sequence of an insert in the pGEM-T vector, according to subject invention (*Acropora millepora* 9-1 in pGEM-T).

SEQ ID NO:29 is the nucleotide sequence of an insert in the pGEM-T vector, according to subject invention (*Acropora millepora* 9-2 in pGEM-T).

SEQ ID NO:30 is the nucleotide sequence of an insert in the pGEM-T vector, according to subject invention (*Acropora millepora* 10-1 in pGEM-T).

SEQ ID NO:31 is the nucleotide sequence of an insert in the pGEM-T vector, according to subject invention (*Acropora millepora* 10-2 in pGEM-T).

SEQ ID NO:32 is the nucleotide sequence of an insert in the pGEM-T vector, according to subject invention (*Acropora millepora* 11-1 in pGEM-T).

SEQ ID NO:33 is the nucleotide sequence of an insert in the pGEM-T vector, according to subject invention (*Acropora millepora* 12-1 in pGEM-T).

SEQ ID NO:34 is the nucleotide sequence of an insert in the pGEM-T vector, according to subject invention (*Acropora millepora* 14-1 in pGEM-T).

SEQ ID NO:35 is the nucleotide sequence of an insert in the pGEM-T vector, according to subject invention (*Acropora nobilis* 15-1 in pGEM-T).

SEQ ID NO:36 is the nucleotide sequence of an insert in the pGEM-T vector, according to subject invention (*Acropora nobilis* 16-1 in pGEM-T).

SEQ ID NO:37 is the nucleotide sequence of an insert in the pGEM-T vector, according to subject invention (*Acropora nobilis* 17-1 in pGEM-T).

SEQ ID NO:38 is the nucleotide sequence of an insert in the pGEM-T vector, according to subject invention (*Agaricia fragilis* 1 in pGEM-T).

SEQ ID NO:39 is the nucleotide sequence of an insert in the pGEM-T vector, according to subject invention (*Agaricia fragilis* 2 in pGEM-T).

SEQ ID NO:40 is the nucleotide sequence of an insert in the pGEM-T vector, according to subject invention (*Agaricia fragilis* 3 in pGEM-T).

SEQ ID NO:41 is the nucleotide sequence of an insert in the pGEM-T vector, according to subject invention (*Agaricia fragilis* 4 in pGEM-T).

SEQ ID NO:42 is the nucleotide sequence of an insert in the pGEM-T vector, according to subject invention (*Agaricia fragilis* 5 in pGEM-T).

SEQ ID NO:43 is the nucleotide sequence of an insert in the pGEM-T vector, according to subject invention (*Agaricia fragilis* 6 in pGEM-T).

SEQ ID NO:44 is the nucleotide sequence of an insert in the pGEM-T vector, according to subject invention (*Agaricia fragilis* 8 in pGEM-T).

SEQ ID NO:45 is the amino aid sequence of a protein of the subject invention as encoded by the following construct: *Acropora aculeus* 1-1 in pGEM-T.

SEQ ID NO:46 is the amino aid sequence of a protein of the subject invention as encoded by the following construct: *Acropora aculeus* 1-2 in pGEM-T.

SEQ ID NO:47 is the amino aid sequence of a protein of the subject invention as expressed by the following construct: *Acropora aculeus* 2-1 in pGEM-T.

SEQ ID NO:48 is the amino aid sequence of a protein of the subject invention as encoded by the following construct: *Acropora aculeus* 2-2 in pGEM-T.

SEQ ID NO:49 is the amino aid sequence of a protein of the subject invention as encoded by the following construct: *Acropora aculeus* 3-1 in pGEM-T.

SEQ ID NO:50 is the amino aid sequence of a protein of the subject invention as encoded by the following construct: *Acropora aculeus* 5-2 in pGEM-T.

SEQ ID NO:51 is the amino aid sequence of a protein of the subject invention as encoded by the following construct: *Acropora aculeus* 6-1 in pGEM-T.

SEQ ID NO:52 is the amino aid sequence of a protein of the subject invention as encoded by the following construct: *Acropora hyacinthus* 7-1 in pGEM-T.

SEQ ID NO:53 is the amino aid sequence of a protein of the subject invention as encoded by the following construct: *Acropora millepora* 8-2 in pGEM-T.

SEQ ID NO:54 is the amino aid sequence of a protein of the subject invention as encoded by the following construct: *Acropora millepora* 9-1 in pGEM-T.

SEQ ID NO:55 is the amino aid sequence of a protein of the subject invention as encoded by the following construct: *Acropora millepora* 9-2 in pGEM-T.

SEQ ID NO:56 is the amino aid sequence of a protein of the subject invention as encoded by the following construct: *Acropora millepora* 10-1 in pGEM-T.

SEQ ID NO:57 is the amino aid sequence of a protein of the subject invention as encoded by the following construct: *Acropora millepora* 10-2 in pGEM-T.

SEQ ID NO:58 is the amino aid sequence of a protein of the subject invention as encoded by the following construct: *Acropora millepora* 11-1 in pGEM-T.

SEQ ID NO:59 is the amino aid sequence of a protein of the subject invention as encoded by the following construct: *Acropora millepora* 12-1 in pGEM-T.

SEQ ID NO:60 is the amino aid sequence of a protein of the subject invention as encoded by the following construct: *Acropora millepora* 14-1 in pGEM-T.

SEQ ID NO:61 is the amino aid sequence of a protein of the subject invention as encoded by the following construct: *Acropora nobilis* 15-1 in pGEM-T.

SEQ ID NO:62 is the amino aid sequence of a protein of the subject invention as encoded by the following construct: *Acropora nobilis* 16-1 in pGEM-T.

SEQ ID NO:63 is the amino aid sequence of a protein of the subject invention as encoded by the following construct: *Acropora nobilis* 17-1 in pGEM-T.

SEQ ID NO:64 is the amino aid sequence of a protein of the subject invention as encoded by the following construct: *Agaricia fragilis* 1 in pGEM-T.

SEQ ID NO:65 is the amino aid sequence of a protein of the subject invention as expressed by the following construct: *Agaricia fragilis* 2 in pGEM-T.

SEQ ID NO:66 is the amino aid sequence of a protein of the subject invention as encoded by the following construct: *Agaricia fragilis* 3 in pGEM-T.

SEQ ID NO:67 is the amino aid sequence of a protein of the subject invention as encoded by the following construct: *Agaricia fragilis* 4 in pGEM-T.

SEQ ID NO:68 is the amino aid sequence of a protein of the subject invention as encoded by the following construct: *Agaricia fragilis* 5 in pGEM-T.

SEQ ID NO:69 is the amino aid sequence of a protein of the subject invention as encoded by the following construct: *Agaricia fragilis* 6 in pGEM-T.

SEQ ID NO:70 is the amino aid sequence of a protein of the subject invention as encoded by the following construct: *Agaricia fragilis* 8 in pGEM-T.

SEQ ID NO:71 is the coding region of the construct of SEQ ID NO:45.

SEQ ID NO:72 is the coding region of the construct of SEQ ID NO:46.

SEQ ID NO:73 is the coding region of the construct of SEQ ID NO:47.

SEQ ID NO:74 is the coding region of the construct of SEQ ID NO:48.

SEQ ID NO:75 is the coding region of the construct of SEQ ID NO:49.

SEQ ID NO:76 is the coding region of the construct of SEQ ID NO:50.

SEQ ID NO:77 is the coding region of the construct of SEQ ID NO:51.

SEQ ID NO:78 is the coding region of the construct of SEQ ID NO:52.

SEQ ID NO:79 is the coding region of the construct of SEQ ID NO:53.

SEQ ID NO:80 is the coding region of the construct of SEQ ID NO:54.

SEQ ID NO:81 is the coding region of the construct of SEQ ID NO:55.

SEQ ID NO:82 is the coding region of the construct of SEQ ID NO:56.

SEQ ID NO:83 is the coding region of the construct of SEQ ID NO:57.

SEQ ID NO:84 is the coding region of the construct of SEQ ID NO:58.

SEQ ID NO:85 is the coding region of the construct of SEQ ID NO:59.

SEQ ID NO:86 is the coding region of the construct of SEQ ID NO:60.

SEQ ID NO:87 is the coding region of the construct of SEQ ID NO:61.

SEQ ID NO:88 is the coding region of the construct of SEQ ID NO:62.

SEQ ID NO:89 is the coding region of the construct of SEQ ID NO:63.

SEQ ID NO:90 is the coding region of the construct of SEQ ID NO:64.

SEQ ID NO:91 is the coding region of the construct of SEQ ID NO:65.

SEQ ID NO:92 is the coding region of the construct of SEQ ID NO:66.

SEQ ID NO:93 is the coding region of the construct of SEQ ID NO:67.

SEQ ID NO:94 is the coding region of the construct of SEQ ID NO:68.

SEQ ID NO:95 is the coding region of the construct of SEQ ID NO:69.

SEQ ID NO:96 is the coding region of the construct of SEQ ID NO:70.

DETAILED DESCRIPTION OF THE INVENTION

The present invention provides novel fluorescent and colored proteins isolated from marine organisms other than *Aequorea Victoria*. In a particularly preferred embodiment, these proteins are red fluorescent proteins featuring rapid conversion from immature green to mature red under UV-A light. Specifically exemplified herein are scubRFP from *Scolymia cubensis; and g*5.2 (cyan), mc6 (green) and R7 (green) proteins, from *Montastraea cavernosa.*

The subject invention further provides polynucleotide sequences encoding these proteins. These polynucleotide sequences include open reading frames encoding the specific exemplified detectable proteins, as well as expression constructs for expressing these proteins, for example, in bacterial hosts.

The proteins of the present invention can be readily, expressed by any one of the recombinant technology methods known to those skilled in the art having the benefit of the instant disclosure. The preferred method will vary depending upon many factors and considerations, including the host, and the cost and availability of materials and other economic considerations. The optimum production procedure for a given situation will be apparent to those skilled in the art having the benefit of the current disclosure.

The subject invention also concerns cells transformed with a polynucleotide of the present invention comprising a nucleotide sequences encoding a novel detectable protein. These cells may be prokaryotic or eukaryotic, plant or animal. In one embodiment, animals, such as fish, are transformed to provide them with a unique color or ability to fluoresce. Polynucleotides providing the markers of the present invention are stable in a diverse range of hosts, including prokaryotic and eukaryotic organisms, and the translation products are fully functional and capable of providing assayable characteristics.

In another embodiment, the present invention provides methods to synthesize colored and fluorescent proteins in a recombinant cell.

In a specific embodiment, the proteins of the subject invention can be used in molecular fluorescent tagging whereby the coding region of a protein of interest is fused with the coding region for a fluorescent protein of the subject invention. The product of such a gene shows the functional characteristics of the protein of interest, but bears the fluorescent label allowing tracing its movements. See, for example, Eichinger, L., S. S. Lee and M. Schleicher (1999) "Dictyostelium as model system for studies of the actin cytoskeleton by molecular genetics" *Microsc Res Tech* 47:124-134; Falk, M. M. and U. Lauf (2001) "High resolution, fluorescence deconvolution microscopy and tagging with the autofluorescent tracers CFP, GFP, and YFP to study the structural composition of gap junctions in living cells" Microsc Res Tech 52:251-262; Kallal, L. and J. L. Benovic (2000) "Using green fluorescent proteins to study G-protein-coupled receptor localization and trafficking" Trends Pharmacol Sci 21:175-180; and Laird, D. W., K. Jordan, T. Thomas, H. Qin, P. Fistouris and Q. Shao (2001) "Comparative analysis and application of fluorescent protein-tagged connexins" Microsc Res Tech 52:263-272.

In a further embodiment, the subject invention concerns polynucleotides comprising an in-frame fusion of nucleotide sequences encoding multiple genetic markers. In one embodiment, the polynucleotides encode the genetic markers GUS, and a detectable protein of the subject invention.

The subject invention helps to provide a more abundant and diverse collection of proteins, which can be used in place of a GFP protein, such that new proteins are readily available for commercial exploitation by small companies that cannot take advantage of the current technology for financial reasons.

Definitions

As used herein, the terms "nucleic acid" and "polynucleotide" refer to a deoxyribonucleotide, ribonucleotide, or a mixed deoxyribonucleotide and ribonucleotide polymer in either single- or double-stranded form, and unless otherwise limited, would encompass known analogs of natural nucleotides that can function in a similar manner as naturally-occurring nucleotides.

As used herein, "a vector" is a DNA sequence having the elements necessary for the transcription/translation of a gene. Such elements would include, for example, promoters. Various classes of promoters are well known in the art and can be obtained commercially or assembled from the sequences and methods, which are also well known in the art. A number of vectors are available for expression and/or cloning, and include, but are not limited to, pBR322, pUC series, M13 series, and pBLUESCRIPT vectors (Stratagene, La Jolla, Calif.).

As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation.

Detectable Proteins

The subject invention provides novel fluorescent and/or colored proteins. These proteins are exemplified by scubRFP from *Scolymia cubensis* (SEQ ID NO: 7); and g5.2 (cyan) (SEQ ID NO: 8), mc6 (green) (SEQ ID NO: 9) and R7 (green) (SEQ ID NO: 10) proteins, from *Montastraea cavernosa.*

The novel colored and fluorescent proteins of the present invention can be detected using standard long-wave UV light sources or, preferably, optical designs appropriate for detecting agents with the excitation/emission characteristics of the proteins exemplified herein (see, for example, FIGS. 2-29). These proteins are referred to herein as "detectable proteins" or "marker proteins." The interaction of two or more residues of the protein and external agents such as molecular oxygen give rise to the colored and/or fluorescent feature of the proteins.

Advantageously, the use of these proteins facilitate real-time detection in vivo, a substrate is not required, and the relatively small size make the proteins very advantageous.

Substitution of amino acids other than those specifically exemplified or naturally present in the genetic marker proteins of the invention are also contemplated within the scope of the present invention. Such substitutions will create "variant proteins" within the scope of the subject invention. Variants and fragments preferably have emission and excitation maxima within 10 nm of the values shown in FIGS. 2-29. For example, non-natural amino acids can be substituted for the amino acids of the marker proteins, so long as a marker protein having the substituted amino acids retains its ability to be detected through fluorescence and/or color. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ϵ-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form. Allelic variants of a protein sequence of a detectable protein used in the present invention are also encompassed within the scope of the invention.

Amino acids can be generally categorized in the following classes: non-polar, uncharged polar, basic, and acidic. Conservative substitutions whereby a marker protein having an amino acid of one class is replaced with another amino acid of the same class fall within the scope of the subject invention so long as a marker protein having the substitution still is detectable Table 1 below provides a listing of examples of amino acids belonging to each class.

TABLE 1

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

Polynucleotides cDNA sequences encoding the proteins of the present invention are provided. Polynucleotides of the present invention can be composed of either RNA or DNA. Preferably, the polynucleotides are composed of DNA. The subject invention also encompasses those polynucleotides that are complementary in sequence to the polynucleotides disclosed herein.

Specifically exemplified are DNA sequences that encode for scubRFP from *Scolymia cubensis*; and g5.2 (cyan), mc6 (green) and R7 (green) proteins, from *Montastraea cavernosa*. These DNA sequences are set forth in SEQ. ID NOS. 3-6.

Sequences of the subject invention may utilize codons preferred for expression by the selected host strains. These sequences may also have sites for cleavage by restriction enzymes, and/or initial, terminal, or intermediate DNA sequences which facilitate construction of readily expressed vectors.

Because of the degeneracy of the genetic code, a variety of different polynucleotide sequences can encode the detectable proteins of the present invention. In addition, it is well within the skill of a person trained in the art to create alternative polynucleotide sequences encoding the same, or essentially the same, detectable proteins of the subject invention. These variant or alternative polynucleotide sequences are within the scope of the subject invention. As used herein, references to "essentially the same" sequence refers to sequences which encode amino acid substitutions, deletions, additions, or insertions which do not eliminate the detectability of the polypeptide encoded by the polynucleotides of the present invention. Allelic variants of the nucleotide sequences encoding a genetic marker protein of the invention are also encompassed within the scope of the invention.

The subject invention also concerns variants of the polynucleotides of the present invention that encode detectable proteins. Variant sequences include those sequences wherein one or more nucleotides of the sequence have been substituted, deleted, and/or inserted. The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

Polynucleotides and polypeptides of the subject invention can also be defined in terms of more particular identity and/or similarity ranges with those exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used.

The subject invention also contemplates those polynucleotide molecules having sequences that are sufficiently homologous with the polynucleotide sequences exemplified herein so as to permit hybridization with that sequence under standard stringent conditions and standard methods (Maniatis et al. 1982). As used herein, "stringent" conditions for hybridization refers to conditions wherein hybridization is typically carried out overnight at 20-25 C below the melting temperature (Tm) of the DNA hybrid in 6×SSPE, 5× Denhardt's solution, 0.1% SDS, 0.1 mg/ml denatured DNA. The melting temperature, Tm, is described by the following formula (Beltz et al., 1983):

$$Tm=81.5\ C+16.6\ Log\ [Na+]+0.41(\%\ G+C)-0.61(\%\ formamide)-600/\text{length of duplex in base pairs.}$$

Washes are typically carried out as follows:

(1) Twice at room temperature for 15 minutes in 1×SSPE, 0.1% SDS (low stringency wash).

(2) Once at Tm-20 C for 15 minutes in 0.2×SSPE, 0.1% SDS (moderate stringency wash).

The polynucleotide sequences include the DNA strand sequence that is transcribed into RNA and the strand sequence that is complementary to the DNA strand that is transcribed. The polynucleotide sequences also include both full-length sequences as well as shorter sequences derived from the full-length sequences. The polynucleotide sequence includes both the sense and antisense strands either as individual strands or in the duplex.

Recombinant Hosts

Polynucleotide molecules containing DNA sequences encoding the colored and/or fluorescent proteins of the present invention can be introduced into a variety of host cells including bacterial cells, yeast cells, fungal cells, plant cells and animal cells. Methods by which the exogenous genetic material can be introduced into such host cells are well known in the art.

In one embodiment, the invention provides a bacteria cell capable of expressing the novel colored and fluorescent proteins.

Plants, plant tissues, and plant cells bred to contain, or transformed with, a polynucleotide of the invention are also contemplated by the present invention. In one embodiment, the polynucleotide encodes a detectable polypeptide shown in SEQ ID NOS. 7-10, or a functional fragment or variant thereof. Plants within the scope of the present invention include monocotyledonous plants, such as rice, wheat, barley, oats, sorghum, maize, sugarcane, pineapple, onion, bananas, coconut, lilies, grasses, and millet; and dicotyledonous plants, such as peas, alfalfa, tomato, melon, chickpea, chicory, clover, kale, lentil, soybean, tobacco, potato, sweet potato, radish, cabbage, rape, apple trees, grape, cotton, sunflower, and lettuce; and conifers. Techniques for transforming plant cells with a gene are known in the art and include, for example, *Agrobacterium* infection, biolistic methods, electroporation, calcium chloride treatment, etc. Transformed cells can be selected, redifferentiated, and grown into plants using standard methods known in the art. The progeny of any transformed plant cells or plants are also included within the scope of the present invention.

The subject invention also concerns non-human transgenic animals which have incorporated into the host cell genome a polynucleotide of the invention. Methods for producing transgenic animals, including mice, rats, pigs, sheep, cows, fish, and the like are well known in the art.

The subject invention also concerns methods for isolating transformants expressing a transgene. In one embodiment, an expression construct of the present invention comprising a transgene of interest operably linked to a nucleotide sequence encoding a detectable marker of the present invention is used to transform a cell. Methods for transforming cells are well known in the art. Transformed cells expressing the transgene are selected by identifying those cells expressing a genetic marker of the invention.

Expression Constructs

An expression construct of the invention typically comprises a structural gene sequence (encoding a protein), an antisense sequence, or other polynucleotide sequences, or a site for insertion of such sequences, operably linked to a polynucleotide of the present invention encoding a marker. The structural gene can be a gene encoding a protein from a prokaryotic or eukaryotic organism, for example, a human, mammal, insect, plant, bacteria, or virus. Proteins that can be encoded by a gene sequence include, but are not limited to, enzymes, hormones, cytokines, interleukins, receptors, growth factors, immunoglobulins, transcription factors, and *Bacillus thuringiensis* (B.t.) crystal toxin proteins. Sequences encoding B.t. proteins which have codon usage for preferential expression in plants are described in U.S. Pat. Nos. 5,380,831; 5,567,862; 5,567,600; 6,013,523; and 6,015,891. An antisense sequence is a sequence wherein the RNA transcribed from the antisense sequence is at least partially complementary to RNA transcribed from a gene encoding a protein.

Expression constructs of the invention will also generally include regulatory elements that are functional in the intended host cell in which the expression construct is to be expressed. Thus, a person of ordinary skill in the art can select regulatory elements for use in, for example, bacterial host cells, yeast host cells, plant host cells, insect host cells, mammalian host cells, and human host cells. Regulatory elements include promoters, transcription termination sequences, translation termination sequences, enhancers, and polyadenylation elements.

An expression construct of the invention can comprise a promoter sequence operably linked to a polynucleotide sequence encoding a marker of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site as it is from the transcription start site in its natural genetic environment. Some variation in this distance is permitted without substantial decrease in promoter activity. A transcription start site is typically included in the expression construct.

For expression in prokaryotic systems, an expression construct of the invention can comprise promoters such as, for example, alkaline phosphatase promoter, tryptophan (trp) promoter, lambda $P_L$ promoter, β-lactamase promoter, lactose promoter, phoA promoter, T3 promoter, T7 promoter, or tac promoter (de Boer et al., 1983).

Expression constructs for use in bacteria are given in SEQ ID NOS. 11-14, and the corresponding amino acid sequences are given in SEQ ID NOS. 15-18.

If the expression construct is to be provided in a plant cell, plant viral promoters, such as, for example, the cauliflower mosaic virus (CaMV) 35S (including the enhanced CaMV 35S promoter (see, for example U.S. Pat. No. 5,106,739)) or 19S promoter can be used. Plant promoters such as prolifera promoter, Ap3 promoter, heat shock promoters, T-DNA 1'- or 2'-promoter of *A. tumafaciens*, polygalacturonase promoter, chalcone synthase A (CHS-A) promoter from petunia, tobacco PR-1a promoter, ubiquitin promoter, actin promoter, alcA gene promoter, pin2 promoter (Xu et al., 1993), maize WipI promoter, maize trpA gene promoter (U.S. Pat. No. 5,625,136), maize CDPK gene promoter, and RUBISCO SSU promoter (U.S. Pat. No. 5,034,322) can also be used. Seed-specific promoters such as the promoter from a β-phaseolin gene (of kidney bean) or a glycinin gene (of soybean), and others, can also be used. Constitutive promoters (such as the CaMV, ubiquitin, actin, or NOS promoter), tissue-specific promoters (such as the E8 promoter from tomato), developmentally-regulated promoters, and inducible promoters (such as those promoters than can be induced by heat, light, hormones, or chemicals) are contemplated for use with the polynucleotides of the invention.

For expression in animal cells, an expression construct of the invention can comprise suitable promoters that can drive transcription of the polynucleotide sequence. If the cells are mammalian cells, then promoters such as, for example, actin promoter, metallothionein promoter, NF-kappaB promoter, EGR promoter, SRE promoter, IL-2 promoter, NFAT promoter, osteocalcin promoter, SV40 early promoter and SV40 late promoter, Lck promoter, BMP5 promoter, TRP-1 promoter, murine mammary tumor virus long terminal repeat promoter, STAT promoter, or an immunoglobulin promoter can be used in the expression construct. The baculovirus polyhedrin promoter can be used with an expression construct of the invention for expression in insect cells. Promoters suitable for use with an expression construct of the invention in yeast cells include, but are not limited to, 3-phosphoglycerate kinase promoter, glyceraldehyde-3-phosphate dehydrogenase promoter, metallothionein promoter, alcohol dehydrogenase-2 promoter, and hexokinase promoter.

Expression constructs of the invention may optionally contain a transcription termination sequence, a translation termination sequence, signal peptide sequence, and/or enhancer elements. Transcription termination regions can typically be obtained from the 3' untranslated region of a eukaryotic or viral gene sequence. Transcription termination sequences can be positioned downstream of a coding sequence to provide for efficient termination. Signal peptides are a group of short amino terminal sequences that encode information responsible for the relocation of an operably linked mature polypeptide to a wide range of post-translational cellular destinations, ranging from a specific organelle compartment to sites of protein action and the extracellular environment. Targeting marker gene products to an intended cellular and/or extracellular destination through the use of operably linked signal peptide sequence is contemplated for use with the polypeptides of the invention. Enhancers are cis-acting elements that increase activity of a promoter and can also be included in the expression construct. Enhancer elements are known in the art, and include, but are not limited to, the CaMV 35S enhancer element, maize shrunken-1 enhancer element, cytomegalovirus (CMV) early promoter enhancer element, and the SV40 enhancer element.

DNA sequences which direct polyadenylation of the mRNA encoded by the structural gene can also be included in the expression construct. The expression constructs of the invention can also include a polynucleotide sequence that directs transposition of other genes, i.e., a transposon.

Applications

There are many ways in which the novel proteins of the subject invention can be used. In one embodiment, the proteins can be used to identify cells. In these methods the proteins can be used to express fluorescence in a cell. One use for this method is in pre-labeling isolated cells or a population of similar cells prior to exposing the cells to an environment in which different cell types are present. Detection of fluorescence in only the original cells allows the location of such cells to be determined and compared with the total population.

A second group of methods concerns the identification of cells that have been transformed with exogenous DNA of interest. Identifying cells transformed with exogenous DNA is required in many in vitro procedures as well as in in vivo applications such as gene therapy.

In one embodiment of the subject invention, a polynucleotide sequence encoding a protein of the subject invention is fused to a DNA sequence encoding a selected protein in order to directly label the encoded protein. Expressing such a fluorescent and/or colored protein in a cell results in the production of labeled proteins that can be readily detected. This is useful in confirming that a protein is being produced by a chosen host cell. It also allows the location of the selected protein to be determined.

Cells that have been transformed with exogenous DNA can also be identified without creating a fusion protein. Here, the method relies on the identification of cells that have received a plasmid or vector that comprises at least two transcriptional or translational units. A first unit encodes and directs expression of the desired protein, while the second unit encodes and directs expression of the detectable protein. Co-expression of the detectable protein from the second transcriptional or translational unit ensures that cells containing the vector are detected and differentiated from cells that do not contain the vector.

In methods to produce fluorescent molecular weight markers, a gene sequence is generally fused to one or more DNA sequences that encode proteins having defined amino acid sequences and the fusion proteins are expressed from an expression vector. Expression results in the production of fluorescent proteins of defined molecular weight or weights that may be used as markers (following calculation of the size of the complete amino acid sequence).

Amino acid replacements that produce different color forms permit simultaneous use of multiple reporter genes. Different colored proteins can be used to identify multiple cell populations in a mixed cell culture or to track multiple cell types, enabling differences in cell movement or migration to be visualized in real time without the need to add additional agents or fix or kill the cells.

Other options include tracking and determining the ultimate location of multiple proteins within a single cell, tissue or organism; differential promoter analysis in which gene expression from two different promoters is determined in the same cell, tissue or organism; and FACS sorting of mixed cell populations.

The techniques that can be used with spectrally separable proteins are exemplified by confocal microscopy, flow cytometry, and fluorescence activated cell sorting (FACS) using modular flow, dual excitation techniques.

In one embodiment, the subject invention concerns polynucleotides comprising an in-frame fusion of nucleotide sequences encoding multiple genetic markers. For example, a polynucleotide of the invention may comprise a first nucleotide sequence that is operably linked in-frame to a second nucleotide sequence. The polynucleotide encodes the amino acid sequences of the detectable protein and another genetic marker such that the genetic markers are in direct contact with one another, i.e., where the last amino acid of the fluorescent genetic marker is immediately contiguous with the first amino acid of the other genetic marker, or they can be separated by a peptide linker sequence, for example, as described in U.S. Pat. No. 5,891,680 and Li et al., 2001, that do not substantially alter functional activity of the genetic markers.

The subject invention also concerns kits comprising in one or more containers and a polynucleotide and/or protein of the present invention.

Additional useful applications of the technology described herein include, but are not limited to, the following:

FRET—Fluorescence Resonant Energy Transfer: This technique allows observation and quantification of molecular interactions. It requires at least two fluorescent proteins of different colors. Currently the most widely used pair is CFP and YFP (mutated variants of GFP); the proteins of the subject invention may be substituted for either or both of them.

REFERENCES

1. Hanson, M. R. and R. H. Kohler. 2001. GFP imaging: methodology and application to investigate cellular compartmentation in plants. *J Exp Bot* 52: 529-539.
2. Pollok, B. A. and R. Heim. 1999. Using GFP in FRET-based applications. *Trends Cell Biol* 9: 57-60.
3. Schuttrigkeit, T. A., U. Zachariae, T. von Feilitzsch, J. Wiehler, J. von Hummel, B. Steipe and M. E. Michel-Beyerle. 2001. Picosecond time-resolved FRET in the fluorescent protein from Discosoma Red (wt-DsRed). *Chemphyschem* 2:325-328.
4. Hillisch, A., M. Lorenz and S. Diekmann. 2001. Recent advances in FRET: distance determination in protein-DNA complexes. *Curr Opin Struct Biol* 11:201-207.

FRAP—Fluorescence Redistribution After Photobleaching: This technique quantifies the dynamics of tagged molecules or the reporter molecules themselves. It involves in photobleaching (burning out) of all the fluorescent molecules within a small area by intense excitation light and monitoring the process of fluorescence recovery within this area (due to migration of tagged molecules from adjacent areas).

REFERENCES

1. Reits, E. A. and J. J. Neefjes. 2001. From fixed to FRAP: measuring protein mobility and activity in living cells. *Nat Cell Biol* 3: E145-147.

2. Houtsmuller, A. B. and W. Vermeulen. 2001. Macromolecular dynamics in living cell nuclei revealed by fluorescence redistribution after photobleaching. *Histochem Cell Biol* 115:13-21.

"Fluorescent timer" applications: one of the proteins exemplified herein—scubRFP—due to its natural spectroscopic properties, can be used as a reporter that changes color with time. Such reporters make it possible to estimate the time elapsed since the reporter protein was synthesized by quantifying its color. In addition, since the maturation speed (the rate of conversion from green to red) in scubRFP can be increased by UV-A light, it is possible to adjust its timing scale: experiments that need timing in shorter intervals may use appropriate background UV illumination to speed up the green-to-red conversion.

REFERENCES

1. Terskikh, A. V., A. Fradkov, A. Zaraiskiy, A. V. Kajava, M. Matz, S. Kim, I. Weissman and P. Siebert. 2000. "Fluorescent timer": Protein that changes color over time. *Molecular Biology of the Cell* 11:648.

2. Verkhusha, V. V., H. Otsuna, T. Awasaki, H. Oda, S. Tsukita and K. Ito. 2001. An enhanced mutant of red fluorescent protein DsRed for double labeling and developmental timer of neural fiber bundle formation. *Journal of Biological Chemistry* 276:29621-29624.

"Light-inducible fluorescence": since the red fluorescence of scubRFP can be induced by exposure to UV-A light, it is possible to use this protein as a light-inducible reporter. Such a reporter can be used for studying molecular dynamics, in a way that is analogous to FRAP (see above). A small area can be irradiated by the fluorescence-inducing light, after which the process of redistribution of active fluorescent molecules from the irradiated spot can be followed.

REFERENCES

1. Ando, R., H. Hama, M. Yamamoto-Hino, H. Mizuno and A. Miyawaki. 2002. An optical marker based on the UV-induced green-to-red photoconversion of a fluorescent protein. Proceedings of the National Academy of Sciences of the United States of America 99:12651-12656.

2. Patterson, G. H. and J. Lippincott-Schwartz. 2002. A photoactivatable GFP for selective photolabeling of proteins and cells. *Science* 297:1873-1877.

3. Chudakov, D. M., V. V. Belousov, A. G. Zaraisky, V. V. Novoselov, D. B. Staroverov, D. B. Zorov, S. Lukyanov and K. A. Lukyanov. 2003. Kindling fluorescent proteins for precise in vivo photolabeling (vol 21, pg 191, 2003). *Nature Biotechnology* 21:452-452.

Coloring of biological objects for decorative and other non-scientific purposes. Examples: producing decorative fish for aquariums; coloring of fur, wool and milk by means of genetic modifications of appropriate animals; and coloring of decorative plants. Such uses can be implemented by a person skilled in the art having the benefit of the teachings of the current disclosure.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

Bacterial Expression Construct

As illustrated in FIG. 1, to prepare a bacterial expression construct, the ORF of the target detectable protein was amplified by means of polymerase chain reaction (PCR), using primers corresponding to the beginning and end of the protein's ORF. The upstream primer carried a 5'-heel ttgattgattga aggagaaatatcATG (SEQ ID NO:1), which encoded three termination codons in three frames (bold), followed by the ribosome binding site (underlined), 6 spacer bases and initiation ATG codon.

The downstream primer encoded a 6×His tag in place of the original termination codon (the heel sequence was 5'-tta tta gtg atg gtg atg gtg atg (SEQ ID NO:2)), to facilitate protein purification by means of metal-affinity chromatography.

The products of amplification were cloned into pGEM-T vector (Promega) using manufacturer-provided reagents and protocol. The expressing clones were identified after overnight growth of the colonies by their fluorescent appearance.

EXAMPLE 2

Additional Proteins and Polynucleotides

The subject invention also provides proteins from *Acropora* ("staghorn corals") and *Agarica fragilis* ("fragile saucer coral"), as well as polynucleotides encoding these proteins.

In one embodiment, the invention provides nucleotide sequences of the inserts in pGEM-T vector (Promega), the conceptual translations of these inserts, and special properties of purified protein products.

The vector constructs are shown in SEQ ID NO:19-44. The encoded proteins are shown in SEQ ID NO:45-70. The open reading frames encoding the proteins of SEQ ID NO: 45-70 are shown in SEQ ID NO:71-96. The spectral characteristics of the proteins are shown in FIGS. 4-29.

EXAMPLE 3

Excitation and Emission Spectra of the Detectable Proteins

The excitation spectra were measured from the proteins purified after bacterial expression. The spectra are shown in FIGS. 2-29. Emission spectra (dotted lines) were measured using USB2000 uv-vis spectrometer (Ocean Optics), excitation spectra (solid lines)—using spectrofluorometer LS-50B (Perkin Elmer). The indicated positions of excitation and emission maxima are accurate within 5 nm.

EXAMPLE 4

Multiple Marker Constructs

There are several advantages associated with the use of fusion markers, including: 1) achievement of combined functionalities in a single transcription unit, 2) reduced usage of genetic elements, such as promoters and terminators, for expressing multiple marker genes, 3) reduced overall length of insertion sequences that may lead to increased transformation efficiency, and most importantly 4) elimination of molecular interactions between adjacent genetic elements. Such unwanted interactions are frequently encountered when multiple expression units associated with different marker genes are used simultaneously and often complicate the interpretation of expression results.

In an effort to improve marker functionality and versatility, several translational fusions between two genetic markers have been developed. Datla et al. (1991; U.S. Pat. No. 5,639,663) created a bifunctional fusion between GUS and neomycin phosphotransferase (NPTII) to provide a biochemically assayable reporter activity and a conditionally selectable growth advantage for use in plant transformation. Another bifunctional fusion, between GUS and GFP, was also developed to provide both indicative and assayable reporter activities for monitoring transient and stable transgene expression in plant cells (Quaedvlieg et al., 1998). More recently, Li et al. (2001) constructed a bifunctional fusion between GFP and NPTII and successfully used this marker for continuous analysis of promoter activity and transgene expression in transgenic grape plants throughout the entire process of plant development.

Small portions of a protein that provide unique functions such as protein/DNA/substrate binding activity can be inserted into another heterologous protein to create a hybrid fusion with enhanced functionality and utility. In other cases, an entire gene or protein of interest has been fused in-frame to another heterologous gene or protein to form a double fusion to provide combined functionalities. Production of multiple proteins using fusion constructs composed of two genes from transgenic plants has been demonstrated previously (U.S. Pat. No. 6,455,759).

In one embodiment, the subject invention provides cells transformed with a polynucleotide of the present invention comprising an in-frame fusion of nucleotide sequences encoding multiple markers. Preferably, the polynucleotide sequence is provided in an expression construct of the invention. The transformed cell can be a prokaryotic cell, for example, a bacterial cell such as *E. coli* or *B. subtilis*, or the transformed cell can be a eukaryotic cell, for example, a plant or animal cell. Animal cells include human cells, mammalian cells, avian cells, fish cells and insect cells. Mammalian cells include, but are not limited to, COS, 3T3, and CHO cells.

Genetic markers that can be used in conjunction with the detectable proteins of the present invention are known in the art and include, for example, polynucleotides encoding proteins that confer a conditionally selective growth advantage, such as antibiotic resistance and herbicide-resistance; polynucleotides encoding proteins that confer a biochemically assayable reporter activity; and polynucleotides encoding proteins that confer an indicative reporter activity. Examples of polynucleotides encoding proteins providing antibiotic resistance include those that can provide for resistance to one or more of the following antibiotics: hygromycin, kanamycin, bleomycin, G418, streptomycin, paromomycin, and spectinomycin. Kanamycin resistance can be provided by neomycin phosphotransferase (NPTII). Examples of polynucleotides encoding proteins providing herbicide resistance include those that can provide for resistance to phosphinothricin acetyltransferase or glyphosate. Examples of genetic markers that confer assayable or indicative reporters activity that can be used in the present invention include, but are not limited to, polynucleotides encoding β-glucuronidase (GUS), β-galactosidase, chloramphenicol acetyltransferase (CAT), luciferase, nopaline synthase (NOS), and green fluorescence protein (GFP).

It should be understood that the examples and embodiments described herein are for illustrative purposes only and that various modifications or changes in light thereof will be suggested to persons skilled in the art and are to be included within the spirit and purview of this application.

We claim:

1. An isolated protein comprising the amino acid sequence of SEQ ID NO:59, or an amino acid sequence that is at least 95% identical to SEQ ID NO:59; wherein the protein is a fluorescent protein having an excitation maximum between 550 nm and 570 nm and an emission maximum between 583 nm and 603 nm.

2. The isolated protein, according to claim 1, wherein said protein comprises an amino acid sequence that is at least 98% identical to SEQ ID NO:59.

3. The protein, according to claim 1, wherein said protein comprises an amino acid sequence that is at least 99% identical to SEQ ID NO:59.

4. The protein, according to claim 1, wherein said protein comprises the amino acid sequence of SEQ ID NO:59.

* * * * *

SEQUENCE LISTING

```
<160> NUMBER OF SEQ ID NOS: 96

<210> SEQ ID NO 1
<211> LENGTH: 27
<212> TYPE: DNA
<213> ORGANISM: Artificial Sequence
<220> FEATURE:
<223> OTHER INFORMATION: 5' heel of upstream primer

<400> SEQUENCE: 1

ttgattgatt gaaggagaaa tatcatg                                          27


<210> SEQ ID NO 2
<211> LENGTH: 24
<212> TYPE: DNA
<213> ORGANISM: Artificial Sequence
<220> FEATURE:
<223> OTHER INFORMATION: 5' heel of downstream primer

<400> SEQUENCE: 2
```

```
ttattagtga tggtgatggt gatg                                          24


<210> SEQ ID NO 3
<211> LENGTH: 675
<212> TYPE: DNA
<213> ORGANISM: Montastraea cavernosa

<400> SEQUENCE: 3

atgagtgtga ttaagtcaga catgaagatc aagctgccta tggaaggcac tgtaaacggg    60

cacaagtttg tcatcacagg agaaggagaa ggcaagcctt tccagggaac acacactata   120

acccttaaag tcaaagaagg gggacctctg cctttccctt acgacatctt gacaacagca   180

ttccagtacg gcaacagggt attcaccaaa tacccaagag acataccaga ctatttcaag   240

cagtcgtttc ctgaggggta ttcctgggaa agaagcatga ctttcgaaga ccagggcatt   300

tgcaccgtca caagcgacat aaagttggaa ggcgactgtt ttttctacga aattcgattt   360

tatggtgtga actttccctc caatggtcca gttatgcaga agaagacgct gaaatgggag   420

ccatccactg agaatatgta cgtgcgtgat ggagtgctac tgggggatgt taacaggact   480

ctgttgcttg aaggagataa acatcaccga tgtaacttca gaagtactta cagggcgaag   540

aagggtgtcg tgttgccaga atatcacttt gtggaccacc gaattgaaat tctgagccat   600

gacaaagatt acaacaccgt tgaggtgtat gagaatgccg ttgctcgccc ttctatgctg   660

ccgagtaagg cctaa                                                    675


<210> SEQ ID NO 4
<211> LENGTH: 678
<212> TYPE: DNA
<213> ORGANISM: Montastraea cavernosa

<400> SEQUENCE: 4

atgagtgtga ttaaaccaga catgaagatc aagctgcgta tggaaggcgc tgtaaacggg    60

cacaacttcg tgattgaagg agaaggaaaa ggcaagcctt tcgagggaac acagactata   120

aaccttacag tcaaagaagg cggacctctg ccttttgctt acgatatctt gacagcagca   180

ttccagtacg gcaacagggc attcaccaaa tacccaagag acatagcaga ctatttcaag   240

cagtcttttc ctgaggggta ttcctgggaa cgaagcatga cttatgaaga ccagggcatt   300

tgcatcatca agagcgacat aagaatggaa ggcgactgct ttatctatga aattcgatat   360

gatggtgtga actttccccc aagtggtcca gttatgcaaa agaagacgct gaaatgggag   420

ccatccactg agaaaatgta tgtgcgtgat ggagtgctga agggtgatgt taacatggct   480

ctgttgcttg aaggaggtgg ccattaccga tgtgactttc gaagtactta caaagcgaag   540

aaacgtgttc agttgccaga ctatcacttt gtggaccacc gcattgagat tttgagccat   600

gacaatgact acaacaccgt aaagctgtct gagaatgccg aggctcgcta ttctatgctg   660

ccgagtcagg ccaagtaa                                                 678


<210> SEQ ID NO 5
<211> LENGTH: 678
<212> TYPE: DNA
<213> ORGANISM: Montastraea cavernosa

<400> SEQUENCE: 5

atgagtgtga ttaaaccaga tatgaagatc aagctgcgta tgcaaggcgt tgtaaacggg    60

cacaagttcg tgattaaagg agaaggagag ggcaagcctt tcgagggaac gcagactata   120
```

-continued

```
aaccttacag tcaaagaagg cgcacctctc ccttttgctt acgacatctt gacatcagca    180

ttccagtatg gcaacagggt attcaccaaa tatccagacg atataccaga ctatttcaag    240

cagacgtttc ctgaagggta ttcgtgggag cgaatcatgg cttatgaaga ccagagtatt    300

tgcacggcca caagcgacat aaaaatggaa ggcgactgtt ttatctacga aattcaattt    360

catggtgtga actttccacc caatggtcca gttatgcaga agaagacgct gaaatgggaa    420

ccatccaccg agaaaatgta tgtgcgtgat ggagtgctga agggtgatgt taacatggct    480

ctgttgcttg aaggaggtgg ccattaccga tgtgacttca gaagtactta caaagcgaag    540

aaggatgttc atttgccaga ctatcactac gtggaccacc gcattgagat tttgagccat    600

gacaaagatt acaaaaatgt tacgctgtat gagcatgcca aagctcgcta ttctatgctg    660

ccgagtaagg ccaagtaa                                                  678


<210> SEQ ID NO 6
<211> LENGTH: 693
<212> TYPE: DNA
<213> ORGANISM: Scolymia cubensis

<400> SEQUENCE: 6

atgtctgcca tcaagactgt ggtaaagcaa ttcatgaaga tcaagatgtc tttggaaggc     60

actgtaaacg ggcactactt caagattgta ggagagggtg atggcactcc ttttgaggga    120

aaacagactt tacacctcaa ggtcaaagag ggcgcacctc tgccttttgc ctacgatatc    180

ctgacaacag ctcttcatta cggaaacagg gtattcgtcg aatacccaga aaacatccca    240

gactatttca agcagtcgtt ccctaaggga tattcatggg aaagaagcct aactttcgaa    300

gacgggggaa tttgcatcgc cagaagcgac atcaaaatgg ttggcgacac tttccataac    360

gaggttcaat tttacggggt aaactttccc cccaatggtc ctgttatgca gaggcacacg    420

gtgaaatggg agccatccac tgagaagatt tatgtgcgtg atggagtgtt gacgggtgat    480

attaccatgg ctctgttgct taaaggaggt acccattacc gatgtgactt cagaactact    540

tataaagcta aggagaaggg tcccaagttc ccaggctatc accttgtcga tcattgtatt    600

gagattacaa gccatgacaa agattacaac gtggttgagc tgtatgagca tgccgtcgct    660

cattctggat tgccggacag tgccaatcga taa                                 693


<210> SEQ ID NO 7
<211> LENGTH: 224
<212> TYPE: PRT
<213> ORGANISM: Montastraea cavernosa

<400> SEQUENCE: 7

Met Ser Val Ile Lys Ser Asp Met Lys Ile Lys Leu Pro Met Glu Gly
1               5                   10                  15

Thr Val Asn Gly His Lys Phe Val Ile Thr Gly Glu Gly Glu Gly Lys
            20                  25                  30

Pro Phe Gln Gly Thr His Thr Ile Thr Leu Lys Val Lys Glu Gly Gly
        35                  40                  45

Pro Leu Pro Phe Pro Tyr Asp Ile Leu Thr Thr Ala Phe Gln Tyr Gly
    50                  55                  60

Asn Arg Val Phe Thr Lys Tyr Pro Arg Asp Ile Pro Asp Tyr Phe Lys
65                  70                  75                  80

Gln Ser Phe Pro Glu Gly Tyr Ser Trp Glu Arg Ser Met Thr Phe Glu
                85                  90                  95

Asp Gln Gly Ile Cys Thr Val Thr Ser Asp Ile Lys Leu Glu Gly Asp
```

-continued

```
            100                 105                 110

Cys Phe Phe Tyr Glu Ile Arg Phe Tyr Gly Val Asn Phe Pro Ser Asn
        115                 120                 125

Gly Pro Val Met Gln Lys Lys Thr Leu Lys Trp Glu Pro Ser Thr Glu
    130                 135                 140

Asn Met Tyr Val Arg Asp Gly Val Leu Leu Gly Asp Val Asn Arg Thr
145                 150                 155                 160

Leu Leu Leu Glu Gly Asp Lys His His Arg Cys Asn Phe Arg Ser Thr
                165                 170                 175

Tyr Arg Ala Lys Lys Gly Val Val Leu Pro Glu Tyr His Phe Val Asp
            180                 185                 190

His Arg Ile Glu Ile Leu Ser His Asp Lys Asp Tyr Asn Thr Val Glu
        195                 200                 205

Val Tyr Glu Asn Ala Val Ala Arg Pro Ser Met Leu Pro Ser Lys Ala
    210                 215                 220


<210> SEQ ID NO 8
<211> LENGTH: 225
<212> TYPE: PRT
<213> ORGANISM: Montastraea cavernosa

<400> SEQUENCE: 8

Met Ser Val Ile Lys Pro Asp Met Lys Ile Lys Leu Arg Met Glu Gly
1               5                   10                  15

Ala Val Asn Gly His Asn Phe Val Ile Glu Gly Glu Gly Lys Gly Lys
            20                  25                  30

Pro Phe Glu Gly Thr Gln Thr Ile Asn Leu Thr Val Lys Glu Gly Gly
        35                  40                  45

Pro Leu Pro Phe Ala Tyr Asp Ile Leu Thr Ala Ala Phe Gln Tyr Gly
    50                  55                  60

Asn Arg Ala Phe Thr Lys Tyr Pro Arg Asp Ile Ala Asp Tyr Phe Lys
65                  70                  75                  80

Gln Ser Phe Pro Glu Gly Tyr Ser Trp Glu Arg Ser Met Thr Tyr Glu
                85                  90                  95

Asp Gln Gly Ile Cys Ile Ile Lys Ser Asp Ile Arg Met Glu Gly Asp
            100                 105                 110

Cys Phe Ile Tyr Glu Ile Arg Tyr Asp Gly Val Asn Phe Pro Pro Ser
        115                 120                 125

Gly Pro Val Met Gln Lys Lys Thr Leu Lys Trp Glu Pro Ser Thr Glu
    130                 135                 140

Lys Met Tyr Val Arg Asp Gly Val Leu Lys Gly Asp Val Asn Met Ala
145                 150                 155                 160

Leu Leu Leu Glu Gly Gly Gly His Tyr Arg Cys Asp Phe Arg Ser Thr
                165                 170                 175

Tyr Lys Ala Lys Lys Arg Val Gln Leu Pro Asp Tyr His Phe Val Asp
            180                 185                 190

His Arg Ile Glu Ile Leu Ser His Asp Asn Asp Tyr Asn Thr Val Lys
        195                 200                 205

Leu Ser Glu Asn Ala Glu Ala Arg Tyr Ser Met Leu Pro Ser Gln Ala
    210                 215                 220

Lys
225


<210> SEQ ID NO 9
<211> LENGTH: 225
```

```
<212> TYPE: PRT
<213> ORGANISM: Montastraea cavernosa

<400> SEQUENCE: 9

Met Ser Val Ile Lys Pro Asp Met Lys Ile Lys Leu Arg Met Gln Gly
1               5                   10                  15

Val Val Asn Gly His Lys Phe Val Ile Lys Gly Glu Gly Glu Gly Lys
            20                  25                  30

Pro Phe Glu Gly Thr Gln Thr Ile Asn Leu Thr Val Lys Glu Gly Ala
        35                  40                  45

Pro Leu Pro Phe Ala Tyr Asp Ile Leu Thr Ser Ala Phe Gln Tyr Gly
    50                  55                  60

Asn Arg Val Phe Thr Lys Tyr Pro Asp Asp Ile Pro Asp Tyr Phe Lys
65                  70                  75                  80

Gln Thr Phe Pro Glu Gly Tyr Ser Trp Glu Arg Ile Met Ala Tyr Glu
                85                  90                  95

Asp Gln Ser Ile Cys Thr Ala Thr Ser Asp Ile Lys Met Glu Gly Asp
            100                 105                 110

Cys Phe Ile Tyr Glu Ile Gln Phe His Gly Val Asn Phe Pro Pro Asn
        115                 120                 125

Gly Pro Val Met Gln Lys Lys Thr Leu Lys Trp Glu Pro Ser Thr Glu
    130                 135                 140

Lys Met Tyr Val Arg Asp Gly Val Leu Lys Gly Asp Val Asn Met Ala
145                 150                 155                 160

Leu Leu Leu Glu Gly Gly Gly His Tyr Arg Cys Asp Phe Arg Ser Thr
                165                 170                 175

Tyr Lys Ala Lys Lys Asp Val His Leu Pro Asp Tyr His Tyr Val Asp
            180                 185                 190

His Arg Ile Glu Ile Leu Ser His Asp Lys Asp Tyr Lys Asn Val Thr
        195                 200                 205

Leu Tyr Glu His Ala Lys Ala Arg Tyr Ser Met Leu Pro Ser Lys Ala
    210                 215                 220

Lys
225


<210> SEQ ID NO 10
<211> LENGTH: 230
<212> TYPE: PRT
<213> ORGANISM: Scolymia cubensis

<400> SEQUENCE: 10

Met Ser Ala Ile Lys Thr Val Val Lys Gln Phe Met Lys Ile Lys Met
1               5                   10                  15

Ser Leu Glu Gly Thr Val Asn Gly His Tyr Phe Lys Ile Val Gly Glu
            20                  25                  30

Gly Asp Gly Thr Pro Phe Glu Gly Lys Gln Thr Leu His Leu Lys Val
        35                  40                  45

Lys Glu Gly Ala Pro Leu Pro Phe Ala Tyr Asp Ile Leu Thr Thr Ala
    50                  55                  60

Leu His Tyr Gly Asn Arg Val Phe Val Glu Tyr Pro Glu Asn Ile Pro
65                  70                  75                  80

Asp Tyr Phe Lys Gln Ser Phe Pro Lys Gly Tyr Ser Trp Glu Arg Ser
                85                  90                  95

Leu Thr Phe Glu Asp Gly Gly Ile Cys Ile Ala Arg Ser Asp Ile Lys
            100                 105                 110
```

-continued

```
Met Val Gly Asp Thr Phe His Asn Glu Val Gln Phe Tyr Gly Val Asn
        115                 120                 125

Phe Pro Pro Asn Gly Pro Val Met Gln Arg His Thr Val Lys Trp Glu
    130                 135                 140

Pro Ser Thr Glu Lys Ile Tyr Val Arg Asp Gly Val Leu Thr Gly Asp
145                 150                 155                 160

Ile Thr Met Ala Leu Leu Leu Lys Gly Gly Thr His Tyr Arg Cys Asp
                165                 170                 175

Phe Arg Thr Thr Tyr Lys Ala Lys Glu Lys Gly Pro Lys Phe Pro Gly
            180                 185                 190

Tyr His Leu Val Asp His Cys Ile Glu Ile Thr Ser His Asp Lys Asp
        195                 200                 205

Tyr Asn Val Val Glu Leu Tyr Glu His Ala Val Ala His Ser Gly Leu
    210                 215                 220

Pro Asp Ser Ala Asn Arg
225                 230
```

<210> SEQ ID NO 11
<211> LENGTH: 726
<212> TYPE: DNA
<213> ORGANISM: Montastraea cavernosa

<400> SEQUENCE: 11

```
ttgattgatt gaaggagaaa tatcatgagt gtgattaagt cagacatgaa gatcaagctg     60

cctatggaag gcactgtaaa cgggcacaag tttgtcatca caggagaagg agaaggcaag    120

cctttccagg gaacacacac tataaccctt aaagtcaaag aaggggggacc tctgcctttc    180

ccttacgaca tcttgacaac agcattccag tacggcaaca gggtattcac caaataccca    240

agagacatac cagactattt caagcagtcg tttcctgagg ggtattcctg ggaaagaagc    300

atgactttcg aagaccaggg catttgcacc gtcacaagcg acataaagtt ggaaggcgac    360

tgttttttct acgaaattcg attttatggt gtgaactttc cctccaatgg tccagttatg    420

cagaagaaga cgctgaaatg ggagccatcc actgagaata tgtacgtgcg tgatggagtg    480

ctactggggg atgttaacag gactctgttg cttgaaggag ataaacatca ccgatgtaac    540

ttcagaagta cttacagggc gaagaagggt gtcgtgttgc cagaatatca ctttgtggac    600

caccgaattg aaattctgag ccatgacaaa gattacaaca ccgttgaggt gtatgagaat    660

gccgttgctc gcccttctat gctgccgagt aaggccgaaa gtgcacatca ccatcaccat    720

cactaa                                                               726
```

<210> SEQ ID NO 12
<211> LENGTH: 729
<212> TYPE: DNA
<213> ORGANISM: Montastraea cavernosa

<400> SEQUENCE: 12

```
ttgattgatt gaaggagaaa tatcatgagt gtgattaaac cagacatgaa gatcaagctg     60

cgtatggaag gcgctgtaaa cgggcacaac ttcgtgattg aaggagaagg aaaaggcaag    120

cctttcgagg gaacacagac tataaacctt acagtcaaag aaggcggacc tctgcctttt    180

gcttacgata tcttgacagc agcattccag tacggcaaca gggcattcac caaataccca    240

agagacatag cagactattt caagcagtct tttcctgagg ggtattcctg ggaacgaagc    300

atgacttatg aagaccaggg catttgcatc atcaagagcg acataagaat ggaaggcgac    360

tgctttatct atgaaattcg atatgatggt gtgaactttc cccaagtgg tccagttatg    420
```

-continued

```
caaaagaaga cgctgaaatg ggagccatcc actgagaaaa tgtatgtgcg tgatggagtg    480

ctgaagggtg atgttaacat ggctctgttg cttgaaggag gtggccatta ccgatgtgac    540

tttcgaagta cttacaaagc gaagaaacgt gttcagttgc cagactatca ctttgtggac    600

caccgcattg agattttgag ccatgacaat gactacaaca ccgtaaagct gtctgagaat    660

gccgaggctc gctattctat gctgccgagt caggccaagg aaagtgcaca tcaccatcac    720

catcactaa                                                            729
```

<210> SEQ ID NO 13
<211> LENGTH: 729
<212> TYPE: DNA
<213> ORGANISM: Montastraea cavernosa

<400> SEQUENCE: 13

```
ttgattgatt gaaggagaaa tatcatgagt gtgattaaac cagatatgaa gatcaagctg     60

cgtatgcaag gcgttgtaaa cggcacaag ttcgtgatta aaggagaagg agagggcaag    120

cctttcgagg gaacgcagac tataaacctt acagtcaaag aaggcgcacc tctccctttt    180

gcttacgaca tcttgacatc agcattccag tatggcaaca gggtattcac caaatatcca    240

gacgatatac cagactattt caagcagacg tttcctgaag ggtattcgtg ggagcgaatc    300

atggcttatg aagaccagag tatttgcacg gccacaagcg acataaaaat ggaaggcgac    360

tgttttatct acgaaattca atttcatggt gtgaactttc cacccaatgg tccagttatg    420

cagaagaaga cgctgaaatg ggaaccatcc accgagaaaa tgtatgtgcg tgatggagtg    480

ctgaagggtg atgttaacat ggctctgttg cttgaaggag gtggccatta ccgatgtgac    540

ttcagaagta cttacaaagc gaagaaggat gttcatttgc cagactatca ctacgtggac    600

caccgcattg agattttgag ccatgacaaa gattacaaaa atgttacgct gtatgagcat    660

gccaaagctc gctattctat gctgccgagt aaggccaagg aaagtgcaca tcaccatcac    720

catcactaa                                                            729
```

<210> SEQ ID NO 14
<211> LENGTH: 741
<212> TYPE: DNA
<213> ORGANISM: Scolymia cubensis

<400> SEQUENCE: 14

```
ttgattgatt gaaggagaaa tatcatgtct gccatcaaga ctgtggtaaa gcaattcatg     60

aagatcaaga tgtctttgga aggcactgta aacgggcact acttcaagat tgtaggagag    120

ggtgatggca ctccttttga gggaaaacag actttacacc tcaaggtcaa agagggcgca    180

cctctgcctt ttgcctacga tatcctgaca acagctcttc attacggaaa cagggtattc    240

gtcgaatacc cagaaaacat cccagactat ttcaagcagt cgttccctaa gggatattca    300

tgggaaagaa gcctaacttt cgaagacggg ggaatttgca tcgccagaag cgacatcaaa    360

atggttggcg acactttcca taacgaggtt caattttacg gggtaaactt tcccccccaat    420

ggtcctgtta tgcagaggca cacggtgaaa tgggagccat ccactgagaa gatttatgtg    480

cgtgatggag tgttgacggg tgatattacc atggctctgt tgcttaaagg aggtacccat    540

taccgatgtg acttcagaac tacttataaa gctaaggaga agggtcccaa gttcccaggc    600

tatcaccttg tcgatcattg tattgagatt acaagccatg acaaagatta caacgtggtt    660

gagctgtatg agcatgccgt cgctcattct ggattgccgg acagtgccaa tcgattgatt    720
```

```
gattgaagga gaaatatcta a                                              741


<210> SEQ ID NO 15
<211> LENGTH: 234
<212> TYPE: PRT
<213> ORGANISM: Montastraea cavernosa

<400> SEQUENCE: 15

Met Ser Val Ile Lys Ser Asp Met Lys Ile Lys Leu Pro Met Glu Gly
1               5                   10                  15

Thr Val Asn Gly His Lys Phe Val Ile Thr Gly Glu Gly Glu Gly Lys
            20                  25                  30

Pro Phe Gln Gly Thr His Thr Ile Thr Leu Lys Val Lys Glu Gly Gly
        35                  40                  45

Pro Leu Pro Phe Pro Tyr Asp Ile Leu Thr Thr Ala Phe Gln Tyr Gly
    50                  55                  60

Asn Arg Val Phe Thr Lys Tyr Pro Arg Asp Ile Pro Asp Tyr Phe Lys
65                  70                  75                  80

Gln Ser Phe Pro Glu Gly Tyr Ser Trp Glu Arg Ser Met Thr Phe Glu
                85                  90                  95

Asp Gln Gly Ile Cys Thr Val Thr Ser Asp Ile Lys Leu Glu Gly Asp
            100                 105                 110

Cys Phe Phe Tyr Glu Ile Arg Phe Tyr Gly Val Asn Phe Pro Ser Asn
        115                 120                 125

Gly Pro Val Met Gln Lys Lys Thr Leu Lys Trp Glu Pro Ser Thr Glu
    130                 135                 140

Asn Met Tyr Val Arg Asp Gly Val Leu Leu Gly Asp Val Asn Arg Thr
145                 150                 155                 160

Leu Leu Leu Glu Gly Asp Lys His His Arg Cys Asn Phe Arg Ser Thr
                165                 170                 175

Tyr Arg Ala Lys Lys Gly Val Val Leu Pro Glu Tyr His Phe Val Asp
            180                 185                 190

His Arg Ile Glu Ile Leu Ser His Asp Lys Asp Tyr Asn Thr Val Glu
        195                 200                 205

Val Tyr Glu Asn Ala Val Ala Arg Pro Ser Met Leu Pro Ser Lys Ala
    210                 215                 220

Lys Glu Ser Ala His His His His His His
225                 230


<210> SEQ ID NO 16
<211> LENGTH: 234
<212> TYPE: PRT
<213> ORGANISM: Montastraea cavernosa

<400> SEQUENCE: 16

Met Ser Val Ile Lys Pro Asp Met Lys Ile Lys Leu Arg Met Glu Gly
1               5                   10                  15

Ala Val Asn Gly His Asn Phe Val Ile Glu Gly Glu Gly Lys Gly Lys
            20                  25                  30

Pro Phe Glu Gly Thr Gln Thr Ile Asn Leu Thr Val Lys Glu Gly Gly
        35                  40                  45

Pro Leu Pro Phe Ala Tyr Asp Ile Leu Thr Ala Ala Phe Gln Tyr Gly
    50                  55                  60

Asn Arg Ala Phe Thr Lys Tyr Pro Arg Asp Ile Ala Asp Tyr Phe Lys
65                  70                  75                  80

Gln Ser Phe Pro Glu Gly Tyr Ser Trp Glu Arg Ser Met Thr Tyr Glu
```

-continued

```
                85                  90                  95

Asp Gln Gly Ile Cys Ile Ile Lys Ser Asp Ile Arg Met Glu Gly Asp
            100                 105                 110

Cys Phe Ile Tyr Glu Ile Arg Tyr Asp Gly Val Asn Phe Pro Pro Ser
        115                 120                 125

Gly Pro Val Met Gln Lys Lys Thr Leu Lys Trp Glu Pro Ser Thr Glu
    130                 135                 140

Lys Met Tyr Val Arg Asp Gly Val Leu Lys Gly Asp Val Asn Met Ala
145                 150                 155                 160

Leu Leu Leu Glu Gly Gly Gly His Tyr Arg Cys Asp Phe Arg Ser Thr
                165                 170                 175

Tyr Lys Ala Lys Lys Arg Val Gln Leu Pro Asp Tyr His Phe Val Asp
            180                 185                 190

His Arg Ile Glu Ile Leu Ser His Asp Asn Asp Tyr Asn Thr Val Lys
        195                 200                 205

Leu Ser Glu Asn Ala Glu Ala Arg Tyr Ser Met Leu Pro Ser Gln Ala
    210                 215                 220

Lys Glu Ser Ala His His His His His His
225                 230


<210> SEQ ID NO 17
<211> LENGTH: 234
<212> TYPE: PRT
<213> ORGANISM: Montastraea cavernosa

<400> SEQUENCE: 17

Met Ser Val Ile Lys Pro Asp Met Lys Ile Lys Leu Arg Met Gln Gly
1               5                   10                  15

Val Val Asn Gly His Lys Phe Val Ile Lys Gly Glu Gly Glu Gly Lys
            20                  25                  30

Pro Phe Glu Gly Thr Gln Thr Ile Asn Leu Thr Val Lys Glu Gly Ala
        35                  40                  45

Pro Leu Pro Phe Ala Tyr Asp Ile Leu Thr Ser Ala Phe Gln Tyr Gly
    50                  55                  60

Asn Arg Val Phe Thr Lys Tyr Pro Asp Asp Ile Pro Asp Tyr Phe Lys
65                  70                  75                  80

Gln Thr Phe Pro Glu Gly Tyr Ser Trp Glu Arg Ile Met Ala Tyr Glu
                85                  90                  95

Asp Gln Ser Ile Cys Thr Ala Thr Ser Asp Ile Lys Met Glu Gly Asp
            100                 105                 110

Cys Phe Ile Tyr Glu Ile Gln Phe His Gly Val Asn Phe Pro Pro Asn
        115                 120                 125

Gly Pro Val Met Gln Lys Lys Thr Leu Lys Trp Glu Pro Ser Thr Glu
    130                 135                 140

Lys Met Tyr Val Arg Asp Gly Val Leu Lys Gly Asp Val Asn Met Ala
145                 150                 155                 160

Leu Leu Leu Glu Gly Gly Gly His Tyr Arg Cys Asp Phe Arg Ser Thr
                165                 170                 175

Tyr Lys Ala Lys Lys Asp Val His Leu Pro Asp Tyr His Tyr Val Asp
            180                 185                 190

His Arg Ile Glu Ile Leu Ser His Asp Lys Asp Tyr Lys Asn Val Thr
        195                 200                 205

Leu Tyr Glu His Ala Lys Ala Arg Tyr Ser Met Leu Pro Ser Lys Ala
    210                 215                 220
```

-continued

```
Lys Glu Ser Ala His His His His His His
225                 230


<210> SEQ ID NO 18
<211> LENGTH: 238
<212> TYPE: PRT
<213> ORGANISM: Scolymia cubensis

<400> SEQUENCE: 18

Met Ser Ala Ile Lys Thr Val Val Lys Gln Phe Met Lys Ile Lys Met
1               5                   10                  15

Ser Leu Glu Gly Thr Val Asn Gly His Tyr Phe Lys Ile Val Gly Glu
            20                  25                  30

Gly Asp Gly Thr Pro Phe Glu Gly Lys Gln Thr Leu His Leu Lys Val
        35                  40                  45

Lys Glu Gly Ala Pro Leu Pro Phe Ala Tyr Asp Ile Leu Thr Thr Ala
    50                  55                  60

Leu His Tyr Gly Asn Arg Val Phe Val Glu Tyr Pro Glu Asn Ile Pro
65                  70                  75                  80

Asp Tyr Phe Lys Gln Ser Phe Pro Lys Gly Tyr Ser Trp Glu Arg Ser
                85                  90                  95

Leu Thr Phe Glu Asp Gly Gly Ile Cys Ile Ala Arg Ser Asp Ile Lys
            100                 105                 110

Met Val Gly Asp Thr Phe His Asn Glu Val Gln Phe Tyr Gly Val Asn
        115                 120                 125

Phe Pro Pro Asn Gly Pro Val Met Gln Arg His Thr Val Lys Trp Glu
    130                 135                 140

Pro Ser Thr Glu Lys Ile Tyr Val Arg Asp Gly Val Leu Thr Gly Asp
145                 150                 155                 160

Ile Thr Met Ala Leu Leu Leu Lys Gly Gly Thr His Tyr Arg Cys Asp
                165                 170                 175

Phe Arg Thr Thr Tyr Lys Ala Lys Glu Lys Gly Pro Lys Phe Pro Gly
            180                 185                 190

Tyr His Leu Val Asp His Cys Ile Glu Ile Thr Ser His Asp Lys Asp
        195                 200                 205

Tyr Asn Val Val Glu Leu Tyr Glu His Ala Val Ala His Ser Gly Leu
    210                 215                 220

Pro Asp Ser Ala Asn Arg Gln Ser His His His His His His
225                 230                 235


<210> SEQ ID NO 19
<211> LENGTH: 765
<212> TYPE: DNA
<213> ORGANISM: Acropora aculeus

<400> SEQUENCE: 19

ttgattgatt gaaggagaaa tatcatgatc aagccatcta tcctcaacat gtcttattca      60

aagcagggca tcgtacaaga aatgaagacg aaataccgta tggaaggcag tgtcaatggc     120

catgaattca cgatcgaagg tgtaggaact gggtaccctt acgaagggaa acagatgtcc     180

gaattagtga tcatcaagcc taagggaaag cccccttccat tctcctttga catactgtca    240

tcagtctttc aatatggaaa caggtgcttc acaaagtacc ctgcagacat gcctgactat     300

ttcaagcaag cattcccaga tggaatgtca tatgaaaggt catttctatt tgaggatgga     360

gcagttgcta cagccagctg gaacattcgt ctcgaaggaa attgcttcat ccacaattcc     420

atctttcatg gcgtaaactt tcccgatgat ggacccgtaa tgaaaaagaa gacaattggc     480
```

```
tgggataagt ccttcgaaaa aatgactgtg tctaaagagg tgttaagagg tgatgtgact    540

atgtttctta tgctcgaagg aggtggttac cacagatgcc agtttcactc cacttacaaa    600

acagagaagc cggtcgaact gcccccgaat catgtcgtag aacatcaaat tgtgaggacc    660

gaccttggcc aaagtgcaaa aggcttcacg gtcaagctgg aagcacatgc tgcggctcat    720

gttaaccctt tgaaggttca acagcaccat caccatcact aataa                    765


<210> SEQ ID NO 20
<211> LENGTH: 765
<212> TYPE: DNA
<213> ORGANISM: Acropora aculeus

<400> SEQUENCE: 20

ttgattgatt gaaggagaaa tatcatgatc aagccatcta tcctcaacat gtctctttca     60

aagcatggca tcacacaaga aatgccgacg aaataccata tgaaaggcag tgtcaatggc    120

catgaattcg agatcgaagg tgtaggaact ggacaccctt acgaagggac acacatggcc    180

gaattagtga tcataaagcc tgcgggaaaa ccccttccat tctcctttga catactgtca    240

acagtcattc aatacggaaa cagatgcttc actaagtacc ctgcagacct gcctgactat    300

ttcaagcaag catacccagg tggaatgtca tatgaaaggt catttgtgta tcaggatgga    360

ggaattgcta cagcgagctg gaacgttagt ctcgagggaa attgcttcat ccacaaatcc    420

acctatcttg gtgtaaactt tcctgctgat ggacccgtaa tgacaaagaa gacaattggc    480

tgggataaag cctttgaaaa aatgactggg ttcaatgagg tgttaagagg tgatgtgact    540

gagtttctta tgctcgaagg aggtggttac cattcatgcc agtttcactc cacttacaaa    600

ccagagaagc cggtcgaact gcccccgaat catgtcatag aacatcacat tgtgaggacc    660

gaccttggca agactgcaaa aggcttcatg gtcaagctgg tacaacatgc tgcggctcat    720

gttaacactt tgaaggttca acatcaccat caccatcact aataa                    765


<210> SEQ ID NO 21
<211> LENGTH: 716
<212> TYPE: DNA
<213> ORGANISM: Acropora aculeus

<400> SEQUENCE: 21

ttgtcttatt caaagcaggg catcgtacaa gaaatgaaga cgaaataccg tatggaaggc     60

agtgtcaatg gccatgaatt cacgatcgaa ggtgtaggaa ctgggtaccc ttacgaaggg    120

aagcagatgt ccgaattagt gatcgtcaag cctaagggaa agccccttcc attctccttt    180

gacatactgt catcagtctt tcaatatgga aacaggtgct tcacaaagta ccctgcagac    240

atgcctgact atttcaagca agcattccca gatggaatgt catatgaaag gtcatttcta    300

tttgaggatg gagcagttgc tacagccagc tggaacattc gtctcgaagg aaattgcttc    360

atccacaatt ccatctttca tggcgtaaac tttcccgctg atggacccgt aatgaaaaag    420

aagacaattg gctgggataa gtccttcgaa aaaatgactg tgtctaaaga ggtgttaaga    480

ggtgatgtga ctatgtttct tatgctcgaa ggaggtggtt accacagatg ccagtttcac    540

tccacttaca aaacagtgaa gccggtcgaa ctgcccccga atcatgtcgt agaacatcaa    600

attgtgagga ccgaccttgg ccaaagtgca aaaggcttca cagtcaagct ggaagcacat    660

gctgcggctc atgtaaccct ttgaaggttc aacatcacca tcaccatcac taataa        716


<210> SEQ ID NO 22
```

-continued

<211> LENGTH: 765
<212> TYPE: DNA
<213> ORGANISM: Acropora aculeus

<400> SEQUENCE: 22

```
ttgattgatt gaaggagaaa tatcatgatc aagccatcta tcctcaacat gtctctttca     60

aagcatggca tcacacaaga aatgccgacg aaataccata tgaaaggcag tgtcaatggc    120

catgaattcg agatcgaagg tgtaggaact ggacaccctt acgaagggac acacatggcc    180

gaattagtga tcataaagcc tgcgggaaaa ccccttccat tctcctttga catactgtca    240

acagtcattc aatacggaaa cagatgcttc actaagtacc ctgcagacct gcctgactat    300

ttcaagcaag catacccagg tggaatgtca tatgaaaggt catttgtatt tcaggatgga    360

ggaattgcta cagcgagctg gaacgtcggt ctcgagggaa attgcttcat ccacaaatcc    420

acctatcttg gtgtaaactt tcctgctgat ggacccgtaa tgacaaagaa gacaattggc    480

tgggataaag cctttgaaaa aatgactggg ttcaatgagg tgttaagagg tgatgtgact    540

gagtttctta tgctcgaagg aggtggttac cattcatgcc agtttcactc cacttacaaa    600

ccagagaagc cggtcaaact gcccccgaat catgtcatag aacatcacat tgtgaggacc    660

gaccttggca agactgcaaa aggcttcatg gtcaagctgg tacaacatgc tgcggctcat    720

gttaaccctt tgaaggttca acatcaccat caccatcact aataa                     765
```

<210> SEQ ID NO 23
<211> LENGTH: 765
<212> TYPE: DNA
<213> ORGANISM: Acropora aculeus

<400> SEQUENCE: 23

```
ttgattgatt gaaggagaaa tatcatgatc aagccatcta tcctcaacat gtctctttca     60

aagcatggca tcacacaaga aatgccgacg aaataccata tgaaaggcaa tgtcaatggc    120

catgaattcg agatcgaagg tgtaggaact ggacaccctt acgaagggac acacatggcc    180

gaattagtga tcataaagcc tgcgggaaaa ccccttccat tctcctttga catactgtca    240

acagtcattc aatacggaaa cagatgcttc actaagtacc ctgcagacct gcctgactat    300

ttcaagcaag cgtacccagg tggaatgtca tatgaaaggt catttgtatt tcaggatgga    360

ggaattgcta cagcgagctg gaacgttggt ctcgagggaa attgcttcat ccacaaatcc    420

acctatcttg gtgtaaactt tcctgctgat ggacccgtaa tgacaaagaa gacaattggc    480

tgggataaag cctttgaaaa aatgactggg ttcaatgagg tgttaagagg cgatgtgact    540

gggtttctta tgctcgaagg aggtggttac cattcatgcc agtttcactc cacttacaaa    600

ccagagaagc cggtcaaact gcccccgaat catgtcatag aacatcacat tgtgaggacc    660

gaccttggca agactgcaaa aggcttcatg gtcaagctgg tacaacatgc tgcggctcat    720

gtgaaccctt tgaaggttca acatcaccat caccatcact aataa                     765
```

<210> SEQ ID NO 24
<211> LENGTH: 711
<212> TYPE: DNA
<213> ORGANISM: Acropora aculeus

<400> SEQUENCE: 24

```
ttgattgatt gaaggagaaa tatcatgagt gtgatcgcta aacaaatgac ctacaaggtt     60

tatatgtcag gcacggtcaa tggacattac tttgaggtcg aaggcgatgg aaaaggaaag    120

ccttacgagg gggagcagac ggtgaagctc actgtcacca agggaggacc tctgccattt    180
```

```
gcttgggata ttttatcacc acagtcacag tacggaagca taccattcac caaataccct    240

gacgacatcc ctgactatgt aaagcagtca ttcccggagg gatatacatg ggagaggatc    300

atgaactttg aagatggtgc agtgtgtact gtcagcaatg attccagcat ccaaggcaac    360

tgtttcatct acaatgtcaa gttctctggt ttgaactttc ctcccaatgg accggttatg    420

cagaagaaga cacagggctg ggaacccaac actgagcgtc tctttgcacg agatggaatg    480

ctgataggaa acaactttat ggctctgaag ttagaaggag gtggtcacta tttgtgtgaa    540

ttcaaatcta cttacaaggc aaagaagcct gtgaggatgc cagggtatca ctatgttgac    600

cgcaaactgg atgtaaccaa tcacaacagg gattacactt ccgttgagca gcgtgaaatt    660

tccattgcac gcaaacctgt ggtcgcccat caccatcacc atcactaata a             711
```

<210> SEQ ID NO 25
<211> LENGTH: 735
<212> TYPE: DNA
<213> ORGANISM: Acropora aculeus

<400> SEQUENCE: 25

```
ttgattgatt gaaggagaaa tatcatggct gcgctactta gtctcaatat gagtgtgatc     60

gctaaacaaa tgacctacaa ggtttatatg tcaggcacgg tcaatggaca ttactttgag    120

gtcgaaggcg atggaaaagg aaagccttac gagggggagc agacggtgaa gctcactgtc    180

accaagggag gacctctgcc atttgcttgg gatattttat caccgcagtc acagtacgga    240

agcataccat tcaccaaata ccctgacgac atccctgact atgtaaagca gtcattcccg    300

gagggatata catgggagag gatcatgaac tttgaggatg gtgcagtgtg tactgtcagc    360

aatgattcca gcatccaagg caactgtttc atctacaatg tcaagttctc tggtttgaac    420

tttcctccca atggaccggt tatgcggaag aagacacggg gctgggaacc caacactgag    480

cgtctctttg cacgggatgg aatgctgata ggaaacaact ttatggctct gaagttagaa    540

ggaggtggtc actatttgtg tgaattcaaa tctacttaca aggcaaagaa gcctgtgagg    600

atgccagggt atcactatgt tgaccgcaaa ctggatgtaa ccaatcacaa cagggattac    660

acttccgttg agcagtgtga aatttccatt gcacgcaaac ctgtggtcgc ccatcaccat    720

caccatcact aataa                                                     735
```

<210> SEQ ID NO 26
<211> LENGTH: 711
<212> TYPE: DNA
<213> ORGANISM: Acropora hyacinthus

<400> SEQUENCE: 26

```
ttgattgatt gaaggagaaa tatcatgagt gtgatcgcta cacaaatgac ctacaaggtt     60

tatatgtcag gcacggtcaa tggacactac tttgaggtcg aaggcgatgg aaaaggaaag    120

ccttacgagg gggagcaaac ggtaaggctg actgtcacca agggcggacc tctgccgttt    180

gcttgggata ttttatcacc acagtcacag tacggaagca taccattcac caagtaccct    240

gaagacatcc ctgactatgt gaagcagtca ttcccggagg gatatacatg ggagaggatc    300

atgaactttg aagatggtgc agtgtgtact gtcagcaatg attccagcat ccaaggcaac    360

tgtttcatct accatgtcaa gttctctggt ttgaactttc ctcccaatgg acctgttatg    420

cagaagaaga cacagggctg ggaacccaac actgagcgtc tctttgcacg agatggagtt    480

ctgataggaa acaactttat ggccctgaag ttagaaggag gtggtcacta tttgtgtgaa    540
```

-continued

```
ttcaaatcta cttacaaggc aaagaagcct gtgaagatgc ctgggtatca ctttgttgac    600

cgcaaactgg atgtaaccaa tcacaacaag gattacactt ctgttgagca gcgtgaaatt    660

tccattgcac gcaaacctgt ggtcgcccac caccatcacc atcactaata a             711
```

<210> SEQ ID NO 27
<211> LENGTH: 741
<212> TYPE: DNA
<213> ORGANISM: Acropora millepora

<400> SEQUENCE: 27

```
ttgattgatt gaaggagaaa tatcatgtct tattcaaagc agggcatcgc acaagtaatg     60

aagacgaaat accatatgga aggcagtgtc aatggccatg aattcacgat cgaaggtgta    120

ggaactggaa acccttacga aggcacacag atgtccgaat tagtgatcac cgagcctgca    180

ggaaaacccc ttccattctc ctttgacatt ctgtcaacag tctttcagta tggaaacagg    240

tgcttcacaa agtaccctga aggaatgact gactatttca agcaagcatt cccagatgga    300

atgtcatttg aaaggtcatt tctatatgag gatggaggag ttgctacagc cagctggaac    360

attcgtcttg agagagattg cttcatccac aaatccatct atcatggcgt taactttccc    420

gctgatggac ccgtaatgaa aaagaagacc attggctggg ataaagcctt cgaaaaaatg    480

actgtgtcca aagacgtttt aagaggtgat gtgactgagt ttcttatgct cgaaggaggt    540

ggttaccaca gctgccagtt tcactccact tacaaaccag agaagccggt tacactgccc    600

cctaatcatg tcgtggaaca tcacattgtg aggactgacc ttggccaaac tgcaaaaggc    660

ttcacagtca agctggaaga acatgctgcg gctcatgtta accctttgaa ggttcaccat    720

caccatcacc atcactaata a                                              741
```

<210> SEQ ID NO 28
<211> LENGTH: 726
<212> TYPE: DNA
<213> ORGANISM: Acropora millepora

<400> SEQUENCE: 28

```
ttgattgatt gaaggagaaa tatcatgaag ccatctatcc tcaacatgtc ttattcaaag     60

caaggcatcg tacaagaaat gaagacgaaa taccatatgg aaggcagtgt caatggccat    120

gaattcacga tcgaaggtgt aggaactggg tacccttacg aagggaaaca gatatccgaa    180

ttagtgatca tcaagcctgc gggaaaaccc cttccattct cctttgacat actgtcatca    240

gtctttcaat atggaaacag gtgcttcaca aagtaccctg cagacatgcc tgactatttc    300

aagcaagcat tcccagatgg aatgtcatat gaaaggtcat ttctatttga ggatggagca    360

gttgccacag ccagctggaa cattcgtctc gaaggaaatt gcttcatcca caaatccatc    420

tttcatggcg taaactttcc cgctgatgga cccgtaatga aaaagaagac aattgactgg    480

gataagtcct tcgaaaaaat gactgtgtct aaagaggtgc taagaggtga cgtgactatg    540

tttcttatgc tcgaaggagg tggttctcac agatgccaat ttcactccac ttacaaaaca    600

gagaagccgg tcacactgcc cccgaatcat gtcgtagaac atcaaattgt gaggaccgac    660

cttggccaaa ctgcaaaagg cttcacagtc aagctggaag aacatgctgc ggctcatgtt    720

agccta                                                               726
```

<210> SEQ ID NO 29
<211> LENGTH: 761
<212> TYPE: DNA
<213> ORGANISM: Acropora millepora -continued

<400> SEQUENCE: 29

```
ttgattgatt gaaggagaaa tatcatgaag ccatctatcc tcaacatgtc ttattcaaag     60
caaggcatcg tacaagaaat gaagacgaaa taccatatgg aaggcagtgt caatggccat    120
gaattcacga tcgaaggtgt aggaactggg taccccttacg aagggaaaca gatgtccgaa    180
ttagtgatca tcaagcctgc gggaaaaccc cttccattct cctttgacat actgtcatca    240
gtctttcaat atggaaacag gtgcttcaca aagtaccctg cagacatgcc tgactatttc    300
aagcaagcat tcccagatgg aatgtcatat gaaaggtcat ttctatttga ggatggagca    360
gttgccacag ccagctggaa cattcgtctc gaaggaaatt gcttcatcca caaatccatc    420
tttcatggcg taaactttcc cgctgatgga cccgtaatga aaaagaagac aattgactgg    480
gataagtcct tcgaaaaaat gactgtgtct aaagaggtgc taagaggtga cgtgactatg    540
tttcttatgc tcgaaggagg tggttctcac agatgccaat ttcactccac ttacaaaaca    600
gagaagccgg tcacactgcc cccgaatcat gtcgtagaac atcaaattgt gaggaccgac    660
cttggccaaa ctgcaaaagg cttcacagtc aagctggaag aacatgctgc ggctcatgta    720
acccttttgaa ggttcaacat caccatcacc atcactaata a                         761
```

<210> SEQ ID NO 30
<211> LENGTH: 762
<212> TYPE: DNA
<213> ORGANISM: Acropora millepora

<400> SEQUENCE: 30

```
ttgattgatt gaaggagaaa tatcatgagg caatctatcc tcaacatgtc ttattcaaag     60
cagggcatcg tacaagaaat gaagacgaaa taccgtatgg aaggcagtgt caatggccat    120
gaattcacga tcgaaggtgt aggaactggg taccccttacg aagggaagca gatgtccgaa    180
ttagtgatcg tcaagcctaa gggaaagccc cttccattct cctttgacat actgtcatca    240
gtctttcaat atggaaacag gtgcttcaca aagtaccctg cagacatgcc tgactatttc    300
aagcaagcat tcccagatgg aatgtcatat gaaaggtcat ttctatttga ggatggagca    360
gttgctacag ccagctggaa cattcgtctc gaaggaaatt gcttcatcca caattccatc    420
tttcatggcg taaactttcc cgctgatgga cccgtaatga aaaagaagac aattggctgg    480
gataagtcct tcgaaaaaat gactgtgtct aaagaggtgt taagaggtga tgtgactatg    540
tttcttatgc tcgaaggagg tggttaccac agatgccagt ttcactccac ttacaaaaca    600
gtgaagccgg tcgaactgcc cccgaatcat gtcgtagaac atcaaattgt gaggaccgac    660
cttggccaaa gtgcaaaagg cttcacagtc aagctggaag cacatgctgc ggctcatgtt    720
aacccttttga aggttcaaca tcaccatcac catcactaat aa                        762
```

<210> SEQ ID NO 31
<211> LENGTH: 762
<212> TYPE: DNA
<213> ORGANISM: Acropora millepora

<400> SEQUENCE: 31

```
ttgattgatt gaaggagaaa tatcatgaag ccatctatcc tcaacatgtc tcattcaaag     60
caaggcatcg cacaagtaat gaagacgaaa taccatatgg aaggcagtgt caatggccat    120
gaattcacga tcgaaggtgt aggaactgga aacccttacg aaggctcaca gatgtccgag    180
ttagtgatca ccaagcctgc aggaaaaccc cttccattct cctttgacat tctctcaaca    240
```

-continued

```
gtctttcaat atggaaacag gtgcttcaca aagtaccctg aaggaatgac tgactatttc    300

aagcaagcat tcccagatgg aatgtcatat gaaaggtcat ttctatatga ggatggagga    360

gttgctacag ccagctggaa cattcgtctt gagagaggtt gcttcatcca caaatccatc    420

tatcatggcg ttaactttcc cgctgatgga cccgtaatga aaaagaagac cattggctgg    480

gataaggcct tcgaaaaaat gactgtgtcc aaagacgtgt taagaggtga tgtgactggg    540

tttcttatgc tcgaaggagg tggttaccac aactgccagt ttcactccac ttacaaacca    600

gaaaagccgg ttacactgcc cccgaatcat gtcgtggaac atcacattgt gaggactgac    660

cttggccaaa ctgcaaaagg cttcacagcc aagctggaag aacatgctgc ggctcatgta    720

aacccttga aggttcaaca tcaccatcac catcactaat aa                        762
```

```
<210> SEQ ID NO 32
<211> LENGTH: 741
<212> TYPE: DNA
<213> ORGANISM: Acropora millepora

<400> SEQUENCE: 32

ttgattgatt gaaggagaaa tatcatgtct tattcaaagc agggcatcgt acaagaaatg     60

aagacgaaat accatatgga aggcagtgtc aatggccatg aattcacgat cgaaggtgta    120

ggaactgggt acccttacga agggaaacag atgtccgaat tagtgatcat caagcctgcg    180

ggaaaacccc ttccattctc ctttgacata ctgtcatcag tctttcaata tggaaacagg    240

tgcttcacaa agtaccctgc agacatgcct gactatttca agcaagcatt cccagatgga    300

atgtcatatg aaaggtcatt tctatttgag gatggagcag ttgctacagc cagctggaac    360

attcgtctcg aaggaaattg cttcatccac aaatccatct ttcatggcgt aaactttccc    420

gctgatggac ccgtaatgaa aaagaagaca attgactggg ataagtcctt cgaaaaaatg    480

actgtgtcta aagaggtgct aagaggtgac gtgactatgt ttcttatgct cgaaggaggt    540

ggttctcaca gatgccaatt tcactccact tacaaaacag agaagccggt cacactgccc    600

ccgaatcatg tcgtagaaca tcaaattgtg aggaccgacc ttggccaaag tgcaaaaggc    660

tttacagtca agctggaagc acatgctgcg gctcatgtta acccttgaa ggttaaacat    720

caccatcacc atcactaata a                                              741
```

```
<210> SEQ ID NO 33
<211> LENGTH: 744
<212> TYPE: DNA
<213> ORGANISM: Acropora millepora

<400> SEQUENCE: 33

ttgattgatt gaaggagaaa tatcatggct ctgtcaaagc acggtttaac aaaggacatg     60

acgatgaaat accacatgga agggtctgtc gatgggcata aatttgtgat cacgggccac    120

ggcaatggaa atcctttcga agggaaacag actatgaatc tgtgtgtggt tgaaggggga    180

cccctgccat tctccgaaga cattttgtct gctacgtttg actacggaaa cagggtcttc    240

actgaatatc ctcaaggcat ggttgacttt ttcaagaatt catgtccagc tggatacaca    300

tggcacaggt ctttactctt tgaagatgga gcagtttgca caactagtgc agatataaca    360

gtgagtgttg aggagaactg cttttatcac aattccaagt ttcatggagt gaactttcct    420

gctgatggac ctgtgatgaa aaagatgaca actaattggg agccatcctg cgagaaaatc    480

ataccagtac ctagacaggg gatattgaaa ggggatattg ccatgtacct ccttctgaag    540

gatggtgggc gttatcggtg ccagttcgac acaatttaca aagcaaagtc tgacccgaaa    600
```

```
gagatgccgg agtggcactt catccaacat aagctcaccc gggaagaccg cagcgatgct    660

aagaaccaga aatggcaact ggtagaacat gctgttgctt cccgatccgc attgcccgga    720

catcaccatc accatcacta ataa                                           744
```

<210> SEQ ID NO 34
<211> LENGTH: 711
<212> TYPE: DNA
<213> ORGANISM: Acropora millepora

<400> SEQUENCE: 34

```
ttgattgatt gaaggagaaa tatcatgagt gtgatcgcta aacaaatgac ctacaaggtt     60

tatatgtcag gcacggtcaa tggacactac tttgaggtcg aaggcgatgg aaaaggtaag    120

ccctacgagg gggagcagac ggtaaagctc actgtcacca agggcggacc tctgccattt    180

gcttgggata ttttatcacc acagtgtcag tacggaagca taccattcac caagtaccct    240

gaagacatcc ctgactatgt aaagcagtca ttcccggagg gctatacatg ggagaggatc    300

atgaactttg aagatggtgc agtgtgtact gtcagcaatg attccagcat ccaaggcaac    360

tgtttcatct accatgtcaa gttctctggt ttgaactttc ctcccaatgg acctgtcatg    420

cagaagaaga cacagggctg ggaacccaac actgagcgtc tctttgcacg agatggaatg    480

ctgctaggaa acaactttat ggctctgaag ttagaaggag gcggtcacta tttgtgtgaa    540

ttcaaaacta cttacaaggc aaagaagcct gtgaagatgc cagggtatca ctatgttgac    600

cgcaaactgg atgtaaccaa tcacaacaag gattacactt cggttgagca gtgtgaaatt    660

tccattgcac gcaaacctgt ggtcgcccat caccatcacc atcactaata a             711
```

<210> SEQ ID NO 35
<211> LENGTH: 765
<212> TYPE: DNA
<213> ORGANISM: Acropora nobilis

<400> SEQUENCE: 35

```
ttgattgatt gaaggagaaa tatcatgatc aagccatcta tcctcaacat gtcttattca     60

aagcaaggca tcgcacaagt aatgaagacg aaataccata tggaaggcag tgtcaatggc    120

catgaattca cgatcgaagg tgtaggaact ggaaaccctt acgaaggcac acagatgtcc    180

gaattagtga tcaccaagcc tgcaggaaaa ccccttccat tctcctttga cattctgtca    240

acagtctttc aatatggaaa caggtgcttc acaaagtacc ctgaaggaat gactgactat    300

ttcaagcaag cattcccaga tggaatgtca tgtgaaaggt catttctata tgaggatgga    360

ggagttgcta cagccagctg gaacattcgt cttgagagag attgcttcat ccacaaatcc    420

atctatcatg gcgttaactt tcccgctgat ggacccgtaa tgaaaaagaa gaccattggc    480

tgggataaag ccttcgaaaa aatgactgtg tccaaagacg tgttaagagg tgatgtgact    540

gagtttctta tgctcgaagg aggtggttac cacagctgcc agtttcactc cacttacaaa    600

ccagaaaagc cggctgcact gcccccgaat catgtcgtag aacatcacat tgtgaggact    660

gaccttggcc aaagtgcaaa aggcttcaca gtcaagctgg aagaacatgc tgcggctcat    720

gttaaccctt tgaaggttca acatcaccat caccatcact aataa                    765
```

<210> SEQ ID NO 36
<211> LENGTH: 741
<212> TYPE: DNA
<213> ORGANISM: Acropora nobilis -continued

<400> SEQUENCE: 36

```
ttgattgatt gaaggagaaa tatcatgtct tattcaaagc agggcatcgc acaagtaatg     60

aagacgaaat accatatgga aggcagtgtc aatggccatg aattcacgat cgaaggtgta    120

ggaactggaa acccttacga aggcacacag atgtccgaat tggtgatcac caagcctgca    180

ggaaaacccc ttccattctc ctttgacatt ctgtcaacag tctttcaata tggaaacagg    240

tgcttcacaa agtaccctga aggaatgact gactatttca agcaagcatt cccagatgga    300

atgtcatatg aaaggtcatt tctatatgag gatggaggag ttgctacagc cggctggaac    360

attcgtcttg agagagattg cttcatccac aaatccatct atcatggcgt taactttccc    420

gctgatggac ccgtaatgaa gaagaagacc attggctggg ataaagcctt cgaaaaaatg    480

actgtgtcca aagacgtgtt aagaggtgat gtgactgggt ttcttatgct cgaaggaggt    540

ggttaccaca gctgccagtt tcactccact tacaaaccag aaaagccggc tgcactgccc    600

ccgaatcatg tcgtagaaca tcacattgtg aggactgacc ttggccaaag tgcaaaaggc    660

ttcacagtca agctggaaga acatgctgcg gctcatgtta accctttgaa ggttcaacat    720

caccatcacc atcactaata a                                              741
```

<210> SEQ ID NO 37
<211> LENGTH: 741
<212> TYPE: DNA
<213> ORGANISM: Acropora nobilis

<400> SEQUENCE: 37

```
ttgattgatt gaaggagaaa tatcatgtct tattcaaagc agggcatcgc acaagaaatg     60

aagacgaaat accatatgga aggcagtgtc aatggccatg aattcacggt cgaaggtgta    120

gggactgggt acccttacga aggggaacag atgtccgaat tagtgatcat cgagcctgcg    180

ggaaaacccc ttccattctc ctttgacata ctgtcatcag tctttcagta tggaaacagg    240

tgcttcacaa aataccctgc agacatgcct gactatttca agcaagcatt tccagatgga    300

atgtcatatg aaaggtcatt tctatttgag gatggagcag ttgctacagc cagctggaaa    360

attcgtctcg aaggaaattg cttcatccac aactccatct ttaatggcgt aaactttccc    420

gctgatggac ccgtaatgga aaagaagaca attggctggg ataagtcctt cgaaaaaatg    480

actgtgtcta aagaggtgct aagaggtgat gtgactatgt ttcttatgct cgaaggaggt    540

ggttctcaca gatgccagtt tcactccact tacaaaacag agaagccggt cacactgccc    600

ccgaatcatg tcgtagaaca tcaaattgtg aggaccgacc ttggccaaag tgcaaaaggc    660

tttacagtca agctggaagc acatgctgcg gctcatgtta accctttgaa ggttaaacat    720

caccatcacc atcactaata a                                              741
```

<210> SEQ ID NO 38
<211> LENGTH: 726
<212> TYPE: DNA
<213> ORGANISM: Agaricia fragilis

<400> SEQUENCE: 38

```
ttgattgatt gaaggagaaa tatcatgagt gtgattgtaa aggaaatgat gactaagcta     60

cacatggaag gtactgttaa cgggcacgcc cttacaattg aaggcaaagg aaaaggcgat    120

ccttacaatg gagtgcagtc tatgaacctt gacgtcaaag gcggtgcgcc tttgccgttc    180

tctttcgatc tcttgacgcc agcattcatg tacggcaaca gagtgttcgc gaagtatcca    240

gaagacatac cagacttttt caagcaggtg tttcctgaag ggtaccactg ggaaagaagt    300
```

-continued

```
attacctttg aagatcaggc cgtttgtacg gcaaccagcc acataaggct ggaccagaaa    360

gagatgtgtt ttatctatga cgtccgtttt cacggtgtga actttcccgc caatggccca    420

atcatgcaga agaagatact gggatgggag ccatccactg agaaaatgta tgcacgtgat    480

ggggtgctga agggtgatgt taatatgact cttcgtgttg aaggaggtgg ccattaccga    540

gctgacttca gaactactta caaagcaaag aagccagtca acctgccagg ctatcacttc    600

atagaccacc gcattgagat taccaagcac agcaaagatt acaccaatgt tgctttgtat    660

gaggcagcag ttgctcgtca ttctccgctg cctaaggttg ctcatcacca tcaccatcac    720

taataa                                                                726
```

```
<210> SEQ ID NO 39
<211> LENGTH: 725
<212> TYPE: DNA
<213> ORGANISM: Agaricia fragilis

<400> SEQUENCE: 39

ttgattgatt gaaggagaaa tatcatgagt gtgattgtaa aggaaatgat gactaagcta     60

cacatggaag gtactgttaa cgggcacgcc tttacaattg aaggcaaagg aaaaggcgat    120

ccttacaatg gagtgcagtc tatgaacctt gacgtcaaag gcggtgcgcc tttgccgttc    180

tctttcgatc tcttgacgcc agcattcatg tacggcaaca gagtgttcac gaagtatcca    240

gaagacatac cagacttttt caagcaggtg tttcctgaag ggtaccactg ggaaagaagt    300

attacctttg aagatcaggc cgtttgtacg gcaaccagcc acataaggct ggaccagaaa    360

gagatgtgtt ttatctatga cgtccgtttt cacggtgtga actttcccgc caatggccca    420

atcatgcaga agaagatact gggatgggag ccatccactg agaaaatgta tgcacgtgat    480

ggggtgctga agggtgatgt taatatgact cttcgtgttg aaggaggtgg ccattaccga    540

gctgacttca gaactactta caaagcaaag aagccagtca acctgccagg ctatcacttc    600

atagaccacc gcattgagat taccaagcac agcaaagatt acaccaatgt tgctttgtat    660

gaggcagcag ttgctcgtca ttctccgctg cctaaggttg ctcatcacca tcacatcact    720

aataa                                                                 725
```

```
<210> SEQ ID NO 40
<211> LENGTH: 726
<212> TYPE: DNA
<213> ORGANISM: Agaricia fragilis

<400> SEQUENCE: 40

ttgattgatt gaaggagaaa tatcatgagt gtgattgtaa aggaaatgat gactaagcta     60

cacatggaag gtactgttaa cgggcacgcc tttacaattg aaggcaaagg aaaaggcgat    120

ccttacaatg gagtgcagtc tatgaacctt gacgtcaaag gcggtgcgcc tttgccgttc    180

tctttcgatc tcttgacgcc agcattcatg tacggcaaca gagtgttcac gaagtatcca    240

gaagacatac cagacttttt caagcaggtg tttcctgaag ggtaccactg ggaaagaagt    300

attacctttg aagatcaggc cgtttgtacg gcaaccagcc acataaggct ggaccagaaa    360

gagatgtgtt ttatctatga cgtccgtttt cacggtgtga actttcccgc caatggccca    420

atcatgcaga agaagatact gggatgggag ccatccactg agaaaatgta tgcacgtgat    480

ggggtgctga agggtgatgt taatatgact cttcgtgttg aaggaggtgg ccattaccga    540

gctgacttca gaactactta caaagcaaag aagccagtca acctgccagg ctatcacttc    600
```

-continued

```
atagaccacc gcattgagat taccaagcac agcaaagatt acaccaatgt tgctttgtat    660

ggggcagcag ttgctcgtca ttctccgctg cctaaggttt ctcatcacca tcaccatcac    720

taataa                                                                726
```

<210> SEQ ID NO 41
<211> LENGTH: 725
<212> TYPE: DNA
<213> ORGANISM: Agaricia fragilis

<400> SEQUENCE: 41

```
ttgattgatt gaaggaaaat atcatgagtg tgattgtaaa ggaaatgatg actaagctac     60

acatggaagg tactgttaac gggcacgcct ttacaattga aggcaaagga aaaggcgatc    120

cttacaatgg agtgcagtct atgaaccttg acgtcaaagg cggtgcgcct ttgccgttct    180

ctttcgatct cttgacgcca gcattcatgt acggcaacag agtgttcacg aagtatccag    240

aagacatacc agactttttc aagcaggtgt ttcctgaagg gtaccactgg gaaagaagta    300

ttacctttga agatcaggcc gtttgtacgg caaccagcca cataaggctg gaccagaaag    360

agatgtgttt tatctatgac gtccgttttc acggtgtgaa ctttcccgcc aatggcccaa    420

tcatgcagaa gaagatactg ggatgggagc catccactga gaaaatgtat gcacgtgatg    480

gggtgctgaa gggtgatgtt aatgtgactc ttcgtgttga aggaggtggc cattaccgag    540

ctgacttcag aactacttac aaagcaaaga agccagtcaa cctgccaggc tatcacttca    600

tagaccaccg cattgagatt accaagcaca gcaaagatta caccaatgtt gctttgtatg    660

aggcagcagt tgctcgtcat tctccgctgc ctaaggttgc tcatcaccat caccatcact    720

aataa                                                                 725
```

<210> SEQ ID NO 42
<211> LENGTH: 726
<212> TYPE: DNA
<213> ORGANISM: Agaricia fragilis

<400> SEQUENCE: 42

```
ttgattgatt gaaggagaaa tatcatgagt gtgattgtaa aggaaatgat gactaagcta     60

cacatggaag gtactgttaa cgggcacgcc tttacaattg aaggcaaagg agagggcgat    120

ccttacaatg gagtgcagtc tatgaacctt gacgtcaaag gcggtgcgcc tttgccgttc    180

tctttcgatc tcttgacgcc agcattcatg tacggcaaca gagtgttcac gaagtatcca    240

gaagacatac cagacttttt caagcaggtg tttcctgaag ggtaccactg ggaaagaagt    300

attacctttg aagatcaggc cgtttgtacg gctaccagcc acataaggct ggaccagaaa    360

gagatgtgtt ttatctatga cgtccgtttt cacggtgtga actttcccgc caatggccca    420

atcatgcaga agaagatact gggatgggag ccatccactg agaaaatgta tgcacgtgat    480

ggggtgctga agggtgatgt taatatgact cttcgtgttg aaggaggtgg ccattaccga    540

gctgacttca gaactactta caaagcaaag aagccagtca acctgccagg ctatcacttc    600

atagaccacc gcattgagat taccaagcac agcaaagatt acaccaatgt tgctttgtat    660

ggggcagcag ttgctcgtca ttctccgctg cctaaggttg ctcatcacca tcaccatcac    720

taataa                                                                726
```

<210> SEQ ID NO 43
<211> LENGTH: 726
<212> TYPE: DNA
<213> ORGANISM: Agaricia fragilis

<400> SEQUENCE: 43

```
ttgattgatt gaaggagaaa tatcatgagt gtgattgtaa aggaaatgat gactaagcta     60
cacatggaag gtactgttaa cgggcacgcc tttacaattg aaggcaaagg aaaaggcgat    120
ccttacaatg gagtgcagtc tatgaacctt gacgtcaaag gcggtgcgcc tttgccgttc    180
tctttcgatc tcttgacgcc agcattcatg tacggcaaca gagtgttcac gaagtatcca    240
gaagacatac cagacttttt caagcaggtg tttcctgaag ggtaccactg ggaaagaagt    300
attacctttg aagatcaggc cgtttgtacg gcaaccagcc acataaggct ggaccagaaa    360
gagatgtgtt ttatctatga cgtccgtttt cacggtgtga actttcccgc caatggccca    420
atcatgcaga agaagatact gggatgggag ccatccactg agaaaatgta tgcacgtgat    480
ggggtgctga agggtgatgt taatatgact cttcgtgttg aaggaggtgg ccattaccga    540
gctgacttca gaactactta caaagcaaag aagccagtca acctgccagg ctatcacttc    600
atagaccacc gcattgagat taccaagcac agcaaagatt acaccaatgt tgctttgtat    660
gaggcagcag ttgctcgtca ttctccgctg cctaaggttg ctcatcacca tcaccatcac    720
taataa                                                               726
```

<210> SEQ ID NO 44
<211> LENGTH: 726
<212> TYPE: DNA
<213> ORGANISM: Agaricia fragilis

<400> SEQUENCE: 44

```
ttgattgatt gaaggagaaa tatcatgagt gtgattgtaa aggaaatgat gactaagcta     60
cacatggaag gtactgttaa cgggcacgcc tttacaattg aaggcaaagg aaaaggcgat    120
ccttacaatg gagtgcagtc tatgaacctt gacgtcaaag gcggtgcgcc tttgccgttc    180
tctttcgatc tcttgacgcc agcattcatg tacggcaaca gagtgttcac gaagtatcca    240
gaagacatac cagacttttt caagcaggtg tttcctgaag ggtaccactg ggaaagaagt    300
attacctttg aagatcaggc cgtttgtacg gcaaccagcc acataaggct ggaccagaaa    360
gagatgtgtt ttatctatga cgtccgtttt cacggtgtga actttcccgc caatggccca    420
atcatgcaga agaagatact gggatgggag ccatccactg agaaaatgta tgcacgtgat    480
ggggtgctga agggtgatgt taatacgact cttcgtgttg aaggaggtgg ccattaccga    540
gctgacttca gaactactta caaagcaaag aagccagtca acctgccagg ctatcacttc    600
atagaccacc gcattgagat taccaagcac agcaaagatt acaccaatgt tgctttgtat    660
gaggcagcag ttgctcgtca ttctccgctg cctaaggttg ctcatcacca tcaccatcac    720
taataa                                                               726
```

<210> SEQ ID NO 45
<211> LENGTH: 237
<212> TYPE: PRT
<213> ORGANISM: Acropora aculeus

<400> SEQUENCE: 45

```
Met Ser Tyr Ser Lys Gln Gly Ile Val Gln Glu Met Lys Thr Lys Tyr
1               5                   10                  15

Arg Met Glu Gly Ser Val Asn Gly His Glu Phe Thr Ile Glu Gly Val
            20                  25                  30

Gly Thr Gly Tyr Pro Tyr Glu Gly Lys Gln Met Ser Glu Leu Val Ile
        35                  40                  45
```

```
Ile Lys Pro Lys Gly Lys Pro Leu Pro Phe Ser Phe Asp Ile Leu Ser
    50                  55                  60

Ser Val Phe Gln Tyr Gly Asn Arg Cys Phe Thr Lys Tyr Pro Ala Asp
65                  70                  75                  80

Met Pro Asp Tyr Phe Lys Gln Ala Phe Pro Asp Gly Met Ser Tyr Glu
                85                  90                  95

Arg Ser Phe Leu Phe Glu Asp Gly Ala Val Ala Thr Ala Ser Trp Asn
            100                 105                 110

Ile Arg Leu Glu Gly Asn Cys Phe Ile His Asn Ser Ile Phe His Gly
        115                 120                 125

Val Asn Phe Pro Asp Asp Gly Pro Val Met Lys Lys Lys Thr Ile Gly
    130                 135                 140

Trp Asp Lys Ser Phe Glu Lys Met Thr Val Ser Lys Glu Val Leu Arg
145                 150                 155                 160

Gly Asp Val Thr Met Phe Leu Met Leu Glu Gly Gly Gly Tyr His Arg
                165                 170                 175

Cys Gln Phe His Ser Thr Tyr Lys Thr Glu Lys Pro Val Glu Leu Pro
            180                 185                 190

Pro Asn His Val Val Glu His Gln Ile Val Arg Thr Asp Leu Gly Gln
        195                 200                 205

Ser Ala Lys Gly Phe Thr Val Lys Leu Glu Ala His Ala Ala Ala His
    210                 215                 220

Val Asn Pro Leu Lys Val Gln Gln His His His His His
225                 230                 235


<210> SEQ ID NO 46
<211> LENGTH: 237
<212> TYPE: PRT
<213> ORGANISM: Acropora aculeus

<400> SEQUENCE: 46

Met Ser Leu Ser Lys His Gly Ile Thr Gln Glu Met Pro Thr Lys Tyr
1               5                   10                  15

His Met Lys Gly Ser Val Asn Gly His Glu Phe Glu Ile Glu Gly Val
            20                  25                  30

Gly Thr Gly His Pro Tyr Glu Gly Thr His Met Ala Glu Leu Val Ile
        35                  40                  45

Ile Lys Pro Ala Gly Lys Pro Leu Pro Phe Ser Phe Asp Ile Leu Ser
    50                  55                  60

Thr Val Ile Gln Tyr Gly Asn Arg Cys Phe Thr Lys Tyr Pro Ala Asp
65                  70                  75                  80

Leu Pro Asp Tyr Phe Lys Gln Ala Tyr Pro Gly Gly Met Ser Tyr Glu
                85                  90                  95

Arg Ser Phe Val Tyr Gln Asp Gly Gly Ile Ala Thr Ala Ser Trp Asn
            100                 105                 110

Val Ser Leu Glu Gly Asn Cys Phe Ile His Lys Ser Thr Tyr Leu Gly
        115                 120                 125

Val Asn Phe Pro Ala Asp Gly Pro Val Met Thr Lys Lys Thr Ile Gly
    130                 135                 140

Trp Asp Lys Ala Phe Glu Lys Met Thr Gly Phe Asn Glu Val Leu Arg
145                 150                 155                 160

Gly Asp Val Thr Glu Phe Leu Met Leu Glu Gly Gly Gly Tyr His Ser
                165                 170                 175

Cys Gln Phe His Ser Thr Tyr Lys Pro Glu Lys Pro Val Glu Leu Pro
```

-continued

```
            180                 185                 190

Pro Asn His Val Ile Glu His His Ile Val Arg Thr Asp Leu Gly Lys
        195                 200                 205

Thr Ala Lys Gly Phe Met Val Lys Leu Val Gln His Ala Ala Ala His
    210                 215                 220

Val Asn Thr Leu Lys Val Gln His His His His His His
225                 230                 235


<210> SEQ ID NO 47
<211> LENGTH: 265
<212> TYPE: PRT
<213> ORGANISM: Acropora aculeus

<400> SEQUENCE: 47

Met Thr Met Ile Thr Pro Ser Tyr Leu Gly Asp Thr Ile Glu Tyr Ser
1               5                   10                  15

Ser Tyr Ala Ser Asn Ala Leu Gly Ala Leu Pro Tyr Gly Arg Pro Ala
            20                  25                  30

Gly Gly Arg Thr Ser Asp Leu Ser Tyr Ser Lys Gln Gly Ile Val Gln
        35                  40                  45

Glu Met Lys Thr Lys Tyr Arg Met Glu Gly Ser Val Asn Gly His Glu
    50                  55                  60

Phe Thr Ile Glu Gly Val Gly Thr Gly Tyr Pro Tyr Glu Gly Lys Gln
65                  70                  75                  80

Met Ser Glu Leu Val Ile Val Lys Pro Lys Gly Lys Pro Leu Pro Phe
                85                  90                  95

Ser Phe Asp Ile Leu Ser Ser Val Phe Gln Tyr Gly Asn Arg Cys Phe
            100                 105                 110

Thr Lys Tyr Pro Ala Asp Met Pro Asp Tyr Phe Lys Gln Ala Phe Pro
        115                 120                 125

Asp Gly Met Ser Tyr Glu Arg Ser Phe Leu Phe Glu Asp Gly Ala Val
    130                 135                 140

Ala Thr Ala Ser Trp Asn Ile Arg Leu Glu Gly Asn Cys Phe Ile His
145                 150                 155                 160

Asn Ser Ile Phe His Gly Val Asn Phe Pro Ala Asp Gly Pro Val Met
                165                 170                 175

Lys Lys Lys Thr Ile Gly Trp Asp Lys Ser Phe Glu Lys Met Thr Val
            180                 185                 190

Ser Lys Glu Val Leu Arg Gly Asp Val Thr Met Phe Leu Met Leu Glu
        195                 200                 205

Gly Gly Gly Tyr His Arg Cys Gln Phe His Ser Thr Tyr Lys Thr Val
    210                 215                 220

Lys Pro Val Glu Leu Pro Pro Asn His Val Val Glu His Gln Ile Val
225                 230                 235                 240

Arg Thr Asp Leu Gly Gln Ser Ala Lys Gly Phe Thr Val Lys Leu Glu
                245                 250                 255

Ala His Ala Ala Ala His Val Thr Leu
            260                 265


<210> SEQ ID NO 48
<211> LENGTH: 237
<212> TYPE: PRT
<213> ORGANISM: Acropora aculeus

<400> SEQUENCE: 48

Met Ser Leu Ser Lys His Gly Ile Thr Gln Glu Met Pro Thr Lys Tyr
```

-continued

```
1               5                   10                  15

His Met Lys Gly Ser Val Asn Gly His Glu Phe Glu Ile Glu Gly Val
            20                  25                  30

Gly Thr Gly His Pro Tyr Glu Gly Thr His Met Ala Glu Leu Val Ile
        35                  40                  45

Ile Lys Pro Ala Gly Lys Pro Leu Pro Phe Ser Phe Asp Ile Leu Ser
    50                  55                  60

Thr Val Ile Gln Tyr Gly Asn Arg Cys Phe Thr Lys Tyr Pro Ala Asp
65                  70                  75                  80

Leu Pro Asp Tyr Phe Lys Gln Ala Tyr Pro Gly Gly Met Ser Tyr Glu
                85                  90                  95

Arg Ser Phe Val Phe Gln Asp Gly Gly Ile Ala Thr Ala Ser Trp Asn
            100                 105                 110

Val Gly Leu Glu Gly Asn Cys Phe Ile His Lys Ser Thr Tyr Leu Gly
        115                 120                 125

Val Asn Phe Pro Ala Asp Gly Pro Val Met Thr Lys Lys Thr Ile Gly
    130                 135                 140

Trp Asp Lys Ala Phe Glu Lys Met Thr Gly Phe Asn Glu Val Leu Arg
145                 150                 155                 160

Gly Asp Val Thr Glu Phe Leu Met Leu Glu Gly Gly Gly Tyr His Ser
                165                 170                 175

Cys Gln Phe His Ser Thr Tyr Lys Pro Glu Lys Pro Val Lys Leu Pro
            180                 185                 190

Pro Asn His Val Ile Glu His His Ile Val Arg Thr Asp Leu Gly Lys
        195                 200                 205

Thr Ala Lys Gly Phe Met Val Lys Leu Val Gln His Ala Ala Ala His
    210                 215                 220

Val Asn Pro Leu Lys Val Gln His His His His His His
225                 230                 235


<210> SEQ ID NO 49
<211> LENGTH: 237
<212> TYPE: PRT
<213> ORGANISM: Acropora aculeus

<400> SEQUENCE: 49

Met Ser Leu Ser Lys His Gly Ile Thr Gln Glu Met Pro Thr Lys Tyr
1               5                   10                  15

His Met Lys Gly Asn Val Asn Gly His Glu Phe Glu Ile Glu Gly Val
            20                  25                  30

Gly Thr Gly His Pro Tyr Glu Gly Thr His Met Ala Glu Leu Val Ile
        35                  40                  45

Ile Lys Pro Ala Gly Lys Pro Leu Pro Phe Ser Phe Asp Ile Leu Ser
    50                  55                  60

Thr Val Ile Gln Tyr Gly Asn Arg Cys Phe Thr Lys Tyr Pro Ala Asp
65                  70                  75                  80

Leu Pro Asp Tyr Phe Lys Gln Ala Tyr Pro Gly Gly Met Ser Tyr Glu
                85                  90                  95

Arg Ser Phe Val Phe Gln Asp Gly Gly Ile Ala Thr Ala Ser Trp Asn
            100                 105                 110

Val Gly Leu Glu Gly Asn Cys Phe Ile His Lys Ser Thr Tyr Leu Gly
        115                 120                 125

Val Asn Phe Pro Ala Asp Gly Pro Val Met Thr Lys Lys Thr Ile Gly
    130                 135                 140
```

-continued

```
Trp Asp Lys Ala Phe Glu Lys Met Thr Gly Phe Asn Glu Val Leu Arg
145                 150                 155                 160

Gly Asp Val Thr Gly Phe Leu Met Leu Glu Gly Gly Gly Tyr His Ser
                165                 170                 175

Cys Gln Phe His Ser Thr Tyr Lys Pro Glu Lys Pro Val Lys Leu Pro
            180                 185                 190

Pro Asn His Val Ile Glu His His Ile Val Arg Thr Asp Leu Gly Lys
        195                 200                 205

Thr Ala Lys Gly Phe Met Val Lys Leu Val Gln His Ala Ala Ala His
    210                 215                 220

Val Asn Pro Leu Lys Val Gln His His His His His His
225                 230                 235


<210> SEQ ID NO 50
<211> LENGTH: 227
<212> TYPE: PRT
<213> ORGANISM: Acropora aculeus

<400> SEQUENCE: 50

Met Ser Val Ile Ala Lys Gln Met Thr Tyr Lys Val Tyr Met Ser Gly
1               5                   10                  15

Thr Val Asn Gly His Tyr Phe Glu Val Glu Gly Asp Gly Lys Gly Lys
            20                  25                  30

Pro Tyr Glu Gly Glu Gln Thr Val Lys Leu Thr Val Thr Lys Gly Gly
        35                  40                  45

Pro Leu Pro Phe Ala Trp Asp Ile Leu Ser Pro Gln Ser Gln Tyr Gly
    50                  55                  60

Ser Ile Pro Phe Thr Lys Tyr Pro Asp Asp Ile Pro Asp Tyr Val Lys
65                  70                  75                  80

Gln Ser Phe Pro Glu Gly Tyr Thr Trp Glu Arg Ile Met Asn Phe Glu
                85                  90                  95

Asp Gly Ala Val Cys Thr Val Ser Asn Asp Ser Ser Ile Gln Gly Asn
            100                 105                 110

Cys Phe Ile Tyr Asn Val Lys Phe Ser Gly Leu Asn Phe Pro Pro Asn
        115                 120                 125

Gly Pro Val Met Gln Lys Lys Thr Gln Gly Trp Glu Pro Asn Thr Glu
    130                 135                 140

Arg Leu Phe Ala Arg Asp Gly Met Leu Ile Gly Asn Asn Phe Met Ala
145                 150                 155                 160

Leu Lys Leu Glu Gly Gly Gly His Tyr Leu Cys Glu Phe Lys Ser Thr
                165                 170                 175

Tyr Lys Ala Lys Lys Pro Val Arg Met Pro Gly Tyr His Tyr Val Asp
            180                 185                 190

Arg Lys Leu Asp Val Thr Asn His Asn Arg Asp Tyr Thr Ser Val Glu
        195                 200                 205

Gln Arg Glu Ile Ser Ile Ala Arg Lys Pro Val Val Ala His His His
    210                 215                 220

His His His
225


<210> SEQ ID NO 51
<211> LENGTH: 227
<212> TYPE: PRT
<213> ORGANISM: Acropora aculeus

<400> SEQUENCE: 51
```

-continued

```
Met Ser Val Ile Ala Lys Gln Met Thr Tyr Lys Val Tyr Met Ser Gly
1               5                   10                  15

Thr Val Asn Gly His Tyr Phe Glu Val Glu Gly Asp Gly Lys Gly Lys
            20                  25                  30

Pro Tyr Glu Gly Glu Gln Thr Val Lys Leu Thr Val Thr Lys Gly Gly
        35                  40                  45

Pro Leu Pro Phe Ala Trp Asp Ile Leu Ser Pro Gln Ser Gln Tyr Gly
    50                  55                  60

Ser Ile Pro Phe Thr Lys Tyr Pro Asp Asp Ile Pro Asp Tyr Val Lys
65                  70                  75                  80

Gln Ser Phe Pro Glu Gly Tyr Thr Trp Glu Arg Ile Met Asn Phe Glu
                85                  90                  95

Asp Gly Ala Val Cys Thr Val Ser Asn Asp Ser Ser Ile Gln Gly Asn
            100                 105                 110

Cys Phe Ile Tyr Asn Val Lys Phe Ser Gly Leu Asn Phe Pro Pro Asn
        115                 120                 125

Gly Pro Val Met Arg Lys Lys Thr Arg Gly Trp Glu Pro Asn Thr Glu
    130                 135                 140

Arg Leu Phe Ala Arg Asp Gly Met Leu Ile Gly Asn Asn Phe Met Ala
145                 150                 155                 160

Leu Lys Leu Glu Gly Gly Gly His Tyr Leu Cys Glu Phe Lys Ser Thr
                165                 170                 175

Tyr Lys Ala Lys Lys Pro Val Arg Met Pro Gly Tyr His Tyr Val Asp
            180                 185                 190

Arg Lys Leu Asp Val Thr Asn His Asn Arg Asp Tyr Thr Ser Val Glu
        195                 200                 205

Gln Cys Glu Ile Ser Ile Ala Arg Lys Pro Val Val Ala His His His
    210                 215                 220

His His His
225
```

<210> SEQ ID NO 52
<211> LENGTH: 227
<212> TYPE: PRT
<213> ORGANISM: Acropora hyacinthus

<400> SEQUENCE: 52

```
Met Ser Val Ile Ala Thr Gln Met Thr Tyr Lys Val Tyr Met Ser Gly
1               5                   10                  15

Thr Val Asn Gly His Tyr Phe Glu Val Glu Gly Asp Gly Lys Gly Lys
            20                  25                  30

Pro Tyr Glu Gly Glu Gln Thr Val Arg Leu Thr Val Thr Lys Gly Gly
        35                  40                  45

Pro Leu Pro Phe Ala Trp Asp Ile Leu Ser Pro Gln Ser Gln Tyr Gly
    50                  55                  60

Ser Ile Pro Phe Thr Lys Tyr Pro Glu Asp Ile Pro Asp Tyr Val Lys
65                  70                  75                  80

Gln Ser Phe Pro Glu Gly Tyr Thr Trp Glu Arg Ile Met Asn Phe Glu
                85                  90                  95

Asp Gly Ala Val Cys Thr Val Ser Asn Asp Ser Ser Ile Gln Gly Asn
            100                 105                 110

Cys Phe Ile Tyr His Val Lys Phe Ser Gly Leu Asn Phe Pro Pro Asn
        115                 120                 125

Gly Pro Val Met Gln Lys Lys Thr Gln Gly Trp Glu Pro Asn Thr Glu
    130                 135                 140
```

-continued

```
Arg Leu Phe Ala Arg Asp Gly Val Leu Ile Gly Asn Asn Phe Met Ala
145                 150                 155                 160

Leu Lys Leu Glu Gly Gly Gly His Tyr Leu Cys Glu Phe Lys Ser Thr
                165                 170                 175

Tyr Lys Ala Lys Lys Pro Val Lys Met Pro Gly Tyr His Phe Val Asp
            180                 185                 190

Arg Lys Leu Asp Val Thr Asn His Asn Lys Asp Tyr Thr Ser Val Glu
        195                 200                 205

Gln Arg Glu Ile Ser Ile Ala Arg Lys Pro Val Val Ala His His His
    210                 215                 220

His His His
225
```

<210> SEQ ID NO 53
<211> LENGTH: 237
<212> TYPE: PRT
<213> ORGANISM: Acropora millepora

<400> SEQUENCE: 53

```
Met Ser Tyr Ser Lys Gln Gly Ile Ala Gln Val Met Lys Thr Lys Tyr
1               5                   10                  15

His Met Glu Gly Ser Val Asn Gly His Glu Phe Thr Ile Glu Gly Val
            20                  25                  30

Gly Thr Gly Asn Pro Tyr Glu Gly Thr Gln Met Ser Glu Leu Val Ile
        35                  40                  45

Thr Glu Pro Ala Gly Lys Pro Leu Pro Phe Ser Phe Asp Ile Leu Ser
    50                  55                  60

Thr Val Phe Gln Tyr Gly Asn Arg Cys Phe Thr Lys Tyr Pro Glu Gly
65                  70                  75                  80

Met Thr Asp Tyr Phe Lys Gln Ala Phe Pro Asp Gly Met Ser Phe Glu
                85                  90                  95

Arg Ser Phe Leu Tyr Glu Asp Gly Gly Val Ala Thr Ala Ser Trp Asn
            100                 105                 110

Ile Arg Leu Glu Arg Asp Cys Phe Ile His Lys Ser Ile Tyr His Gly
        115                 120                 125

Val Asn Phe Pro Ala Asp Gly Pro Val Met Lys Lys Lys Thr Ile Gly
    130                 135                 140

Trp Asp Lys Ala Phe Glu Lys Met Thr Val Ser Lys Asp Val Leu Arg
145                 150                 155                 160

Gly Asp Val Thr Glu Phe Leu Met Leu Glu Gly Gly Gly Tyr His Ser
                165                 170                 175

Cys Gln Phe His Ser Thr Tyr Lys Pro Glu Lys Pro Val Thr Leu Pro
            180                 185                 190

Pro Asn His Val Val Glu His His Ile Val Arg Thr Asp Leu Gly Gln
        195                 200                 205

Thr Ala Lys Gly Phe Thr Val Lys Leu Glu Glu His Ala Ala Ala His
    210                 215                 220

Val Asn Pro Leu Lys Val His His His His His His His
225                 230                 235
```

<210> SEQ ID NO 54
<211> LENGTH: 311
<212> TYPE: PRT
<213> ORGANISM: Acropora millepora

<400> SEQUENCE: 54

-continued

```
Met Ser Tyr Ser Lys Gln Gly Ile Val Gln Glu Met Lys Thr Lys Tyr
1               5                   10                  15

His Met Glu Gly Ser Val Asn Gly His Glu Phe Thr Ile Glu Gly Val
            20                  25                  30

Gly Thr Gly Tyr Pro Tyr Glu Gly Lys Gln Ile Ser Glu Leu Val Ile
        35                  40                  45

Ile Lys Pro Ala Gly Lys Pro Leu Pro Phe Ser Phe Asp Ile Leu Ser
    50                  55                  60

Ser Val Phe Gln Tyr Gly Asn Arg Cys Phe Thr Lys Tyr Pro Ala Asp
65                  70                  75                  80

Met Pro Asp Tyr Phe Lys Gln Ala Phe Pro Asp Gly Met Ser Tyr Glu
                85                  90                  95

Arg Ser Phe Leu Phe Glu Asp Gly Ala Val Ala Thr Ala Ser Trp Asn
            100                 105                 110

Ile Arg Leu Glu Gly Asn Cys Phe Ile His Lys Ser Ile Phe His Gly
        115                 120                 125

Val Asn Phe Pro Ala Asp Gly Pro Val Met Lys Lys Lys Thr Ile Asp
    130                 135                 140

Trp Asp Lys Ser Phe Glu Lys Met Thr Val Ser Lys Glu Val Leu Arg
145                 150                 155                 160

Gly Asp Val Thr Met Phe Leu Met Leu Glu Gly Gly Gly Ser His Arg
                165                 170                 175

Cys Gln Phe His Ser Thr Tyr Lys Thr Glu Lys Pro Val Thr Leu Pro
            180                 185                 190

Pro Asn His Val Val Glu His Gln Ile Val Arg Thr Asp Leu Gly Gln
        195                 200                 205

Thr Ala Lys Gly Phe Thr Val Lys Leu Glu Glu His Ala Ala Ala His
    210                 215                 220

Val Ser Leu Ile Pro Arg Pro Trp Arg Pro Gly Ala Cys Asp Val Gly
225                 230                 235                 240

Pro Asn Ser Pro Tyr Ser Glu Ser Tyr Tyr Asn Ser Leu Ala Val Val
                245                 250                 255

Leu Gln Arg Arg Asp Trp Glu Asn Pro Gly Val Thr Gln Leu Asn Arg
            260                 265                 270

Leu Ala Ala His Pro Pro Phe Ala Ser Trp Arg Asn Ser Glu Glu Ala
        275                 280                 285

Arg Thr Asp Arg Pro Ser Gln Gln Leu Arg Ser Leu Asn Gly Glu Trp
    290                 295                 300

Thr Arg Pro Val Ala Ala His
305                 310
```

<210> SEQ ID NO 55
<211> LENGTH: 227
<212> TYPE: PRT
<213> ORGANISM: Acropora millepora

<400> SEQUENCE: 55

```
Met Ser Tyr Ser Lys Gln Gly Ile Val Gln Glu Met Lys Thr Lys Tyr
1               5                   10                  15

His Met Glu Gly Ser Val Asn Gly His Glu Phe Thr Ile Glu Gly Val
            20                  25                  30

Gly Thr Gly Tyr Pro Tyr Glu Gly Lys Gln Met Ser Glu Leu Val Ile
        35                  40                  45

Ile Lys Pro Ala Gly Lys Pro Leu Pro Phe Ser Phe Asp Ile Leu Ser
```

```
    50                  55                  60

Ser Val Phe Gln Tyr Gly Asn Arg Cys Phe Thr Lys Tyr Pro Ala Asp
65                  70                  75                  80

Met Pro Asp Tyr Phe Lys Gln Ala Phe Pro Asp Gly Met Ser Tyr Glu
                85                  90                  95

Arg Ser Phe Leu Phe Glu Asp Gly Ala Val Ala Thr Ala Ser Trp Asn
            100                 105                 110

Ile Arg Leu Glu Gly Asn Cys Phe Ile His Lys Ser Ile Phe His Gly
        115                 120                 125

Val Asn Phe Pro Ala Asp Gly Pro Val Met Lys Lys Lys Thr Ile Asp
    130                 135                 140

Trp Asp Lys Ser Phe Glu Lys Met Thr Val Ser Lys Glu Val Leu Arg
145                 150                 155                 160

Gly Asp Val Thr Met Phe Leu Met Leu Glu Gly Gly Gly Ser His Arg
                165                 170                 175

Cys Gln Phe His Ser Thr Tyr Lys Thr Glu Lys Pro Val Thr Leu Pro
            180                 185                 190

Pro Asn His Val Val Glu His Gln Ile Val Arg Thr Asp Leu Gly Gln
        195                 200                 205

Thr Ala Lys Gly Phe Thr Val Lys Leu Glu Glu His Ala Ala Ala His
    210                 215                 220

Val Thr Leu
225


<210> SEQ ID NO 56
<211> LENGTH: 237
<212> TYPE: PRT
<213> ORGANISM: Acropora millepora

<400> SEQUENCE: 56

Met Ser Tyr Ser Lys Gln Gly Ile Val Gln Glu Met Lys Thr Lys Tyr
1               5                   10                  15

Arg Met Glu Gly Ser Val Asn Gly His Glu Phe Thr Ile Glu Gly Val
            20                  25                  30

Gly Thr Gly Tyr Pro Tyr Glu Gly Lys Gln Met Ser Glu Leu Val Ile
        35                  40                  45

Val Lys Pro Lys Gly Lys Pro Leu Pro Phe Ser Phe Asp Ile Leu Ser
    50                  55                  60

Ser Val Phe Gln Tyr Gly Asn Arg Cys Phe Thr Lys Tyr Pro Ala Asp
65                  70                  75                  80

Met Pro Asp Tyr Phe Lys Gln Ala Phe Pro Asp Gly Met Ser Tyr Glu
                85                  90                  95

Arg Ser Phe Leu Phe Glu Asp Gly Ala Val Ala Thr Ala Ser Trp Asn
            100                 105                 110

Ile Arg Leu Glu Gly Asn Cys Phe Ile His Asn Ser Ile Phe His Gly
        115                 120                 125

Val Asn Phe Pro Ala Asp Gly Pro Val Met Lys Lys Lys Thr Ile Gly
    130                 135                 140

Trp Asp Lys Ser Phe Glu Lys Met Thr Val Ser Lys Glu Val Leu Arg
145                 150                 155                 160

Gly Asp Val Thr Met Phe Leu Met Leu Glu Gly Gly Gly Tyr His Arg
                165                 170                 175

Cys Gln Phe His Ser Thr Tyr Lys Thr Val Lys Pro Val Glu Leu Pro
            180                 185                 190
```

-continued

```
Pro Asn His Val Val Glu His Gln Ile Val Arg Thr Asp Leu Gly Gln
        195                 200                 205

Ser Ala Lys Gly Phe Thr Val Lys Leu Glu Ala His Ala Ala Ala His
    210                 215                 220

Val Asn Pro Leu Lys Val Gln His His His His His His
225                 230                 235


<210> SEQ ID NO 57
<211> LENGTH: 237
<212> TYPE: PRT
<213> ORGANISM: Acropora millepora

<400> SEQUENCE: 57

Met Ser His Ser Lys Gln Gly Ile Ala Gln Val Met Lys Thr Lys Tyr
1               5                   10                  15

His Met Glu Gly Ser Val Asn Gly His Glu Phe Thr Ile Glu Gly Val
            20                  25                  30

Gly Thr Gly Asn Pro Tyr Glu Gly Ser Gln Met Ser Glu Leu Val Ile
        35                  40                  45

Thr Lys Pro Ala Gly Lys Pro Leu Pro Phe Ser Phe Asp Ile Leu Ser
    50                  55                  60

Thr Val Phe Gln Tyr Gly Asn Arg Cys Phe Thr Lys Tyr Pro Glu Gly
65                  70                  75                  80

Met Thr Asp Tyr Phe Lys Gln Ala Phe Pro Asp Gly Met Ser Tyr Glu
                85                  90                  95

Arg Ser Phe Leu Tyr Glu Asp Gly Gly Val Ala Thr Ala Ser Trp Asn
            100                 105                 110

Ile Arg Leu Glu Arg Gly Cys Phe Ile His Lys Ser Ile Tyr His Gly
        115                 120                 125

Val Asn Phe Pro Ala Asp Gly Pro Val Met Lys Lys Lys Thr Ile Gly
    130                 135                 140

Trp Asp Lys Ala Phe Glu Lys Met Thr Val Ser Lys Asp Val Leu Arg
145                 150                 155                 160

Gly Asp Val Thr Gly Phe Leu Met Leu Glu Gly Gly Gly Tyr His Asn
                165                 170                 175

Cys Gln Phe His Ser Thr Tyr Lys Pro Glu Lys Pro Val Thr Leu Pro
            180                 185                 190

Pro Asn His Val Val Glu His His Ile Val Arg Thr Asp Leu Gly Gln
        195                 200                 205

Thr Ala Lys Gly Phe Thr Ala Lys Leu Glu Glu His Ala Ala Ala His
    210                 215                 220

Val Asn Pro Leu Lys Val Gln His His His His His His
225                 230                 235


<210> SEQ ID NO 58
<211> LENGTH: 237
<212> TYPE: PRT
<213> ORGANISM: Acropora millepora

<400> SEQUENCE: 58

Met Ser Tyr Ser Lys Gln Gly Ile Val Gln Glu Met Lys Thr Lys Tyr
1               5                   10                  15

His Met Glu Gly Ser Val Asn Gly His Glu Phe Thr Ile Glu Gly Val
            20                  25                  30

Gly Thr Gly Tyr Pro Tyr Glu Gly Lys Gln Met Ser Glu Leu Val Ile
        35                  40                  45
```

-continued

```
Ile Lys Pro Ala Gly Lys Pro Leu Pro Phe Ser Phe Asp Ile Leu Ser
    50                  55                  60

Ser Val Phe Gln Tyr Gly Asn Arg Cys Phe Thr Lys Tyr Pro Ala Asp
65                  70                  75                  80

Met Pro Asp Tyr Phe Lys Gln Ala Phe Pro Asp Gly Met Ser Tyr Glu
                85                  90                  95

Arg Ser Phe Leu Phe Glu Asp Gly Ala Val Ala Thr Ala Ser Trp Asn
            100                 105                 110

Ile Arg Leu Glu Gly Asn Cys Phe Ile His Lys Ser Ile Phe His Gly
        115                 120                 125

Val Asn Phe Pro Ala Asp Gly Pro Val Met Lys Lys Lys Thr Ile Asp
    130                 135                 140

Trp Asp Lys Ser Phe Glu Lys Met Thr Val Ser Lys Glu Val Leu Arg
145                 150                 155                 160

Gly Asp Val Thr Met Phe Leu Met Leu Glu Gly Gly Gly Ser His Arg
                165                 170                 175

Cys Gln Phe His Ser Thr Tyr Lys Thr Glu Lys Pro Val Thr Leu Pro
            180                 185                 190

Pro Asn His Val Val Glu His Gln Ile Val Arg Thr Asp Leu Gly Gln
        195                 200                 205

Ser Ala Lys Gly Phe Thr Val Lys Leu Glu Ala His Ala Ala Ala His
    210                 215                 220

Val Asn Pro Leu Lys Val Lys His His His His His His
225                 230                 235
```

<210> SEQ ID NO 59
<211> LENGTH: 238
<212> TYPE: PRT
<213> ORGANISM: Acropora millepora

<400> SEQUENCE: 59

```
Met Ala Leu Ser Lys His Gly Leu Thr Lys Asp Met Thr Met Lys Tyr
1               5                   10                  15

His Met Glu Gly Ser Val Asp Gly His Lys Phe Val Ile Thr Gly His
            20                  25                  30

Gly Asn Gly Asn Pro Phe Glu Gly Lys Gln Thr Met Asn Leu Cys Val
        35                  40                  45

Val Glu Gly Gly Pro Leu Pro Phe Ser Glu Asp Ile Leu Ser Ala Thr
    50                  55                  60

Phe Asp Tyr Gly Asn Arg Val Phe Thr Glu Tyr Pro Gln Gly Met Val
65                  70                  75                  80

Asp Phe Phe Lys Asn Ser Cys Pro Ala Gly Tyr Thr Trp His Arg Ser
                85                  90                  95

Leu Leu Phe Glu Asp Gly Ala Val Cys Thr Thr Ser Ala Asp Ile Thr
            100                 105                 110

Val Ser Val Glu Glu Asn Cys Phe Tyr His Asn Ser Lys Phe His Gly
        115                 120                 125

Val Asn Phe Pro Ala Asp Gly Pro Val Met Lys Lys Met Thr Thr Asn
    130                 135                 140

Trp Glu Pro Ser Cys Glu Lys Ile Ile Pro Val Pro Arg Gln Gly Ile
145                 150                 155                 160

Leu Lys Gly Asp Ile Ala Met Tyr Leu Leu Leu Lys Asp Gly Gly Arg
                165                 170                 175

Tyr Arg Cys Gln Phe Asp Thr Ile Tyr Lys Ala Lys Ser Asp Pro Lys
            180                 185                 190
```

-continued

```
Glu Met Pro Glu Trp His Phe Ile Gln His Lys Leu Thr Arg Glu Asp
        195                 200                 205

Arg Ser Asp Ala Lys Asn Gln Lys Trp Gln Leu Val Glu His Ala Val
    210                 215                 220

Ala Ser Arg Ser Ala Leu Pro Gly His His His His His His
225                 230                 235


<210> SEQ ID NO 60
<211> LENGTH: 227
<212> TYPE: PRT
<213> ORGANISM: Acropora millepora

<400> SEQUENCE: 60

Met Ser Val Ile Ala Lys Gln Met Thr Tyr Lys Val Tyr Met Ser Gly
1               5                   10                  15

Thr Val Asn Gly His Tyr Phe Glu Val Glu Gly Asp Gly Lys Gly Lys
            20                  25                  30

Pro Tyr Glu Gly Glu Gln Thr Val Lys Leu Thr Val Thr Lys Gly Gly
        35                  40                  45

Pro Leu Pro Phe Ala Trp Asp Ile Leu Ser Pro Gln Cys Gln Tyr Gly
    50                  55                  60

Ser Ile Pro Phe Thr Lys Tyr Pro Glu Asp Ile Pro Asp Tyr Val Lys
65                  70                  75                  80

Gln Ser Phe Pro Glu Gly Tyr Thr Trp Glu Arg Ile Met Asn Phe Glu
                85                  90                  95

Asp Gly Ala Val Cys Thr Val Ser Asn Asp Ser Ser Ile Gln Gly Asn
            100                 105                 110

Cys Phe Ile Tyr His Val Lys Phe Ser Gly Leu Asn Phe Pro Pro Asn
        115                 120                 125

Gly Pro Val Met Gln Lys Lys Thr Gln Gly Trp Glu Pro Asn Thr Glu
    130                 135                 140

Arg Leu Phe Ala Arg Asp Gly Met Leu Leu Gly Asn Asn Phe Met Ala
145                 150                 155                 160

Leu Lys Leu Glu Gly Gly Gly His Tyr Leu Cys Glu Phe Lys Thr Thr
                165                 170                 175

Tyr Lys Ala Lys Lys Pro Val Lys Met Pro Gly Tyr His Tyr Val Asp
            180                 185                 190

Arg Lys Leu Asp Val Thr Asn His Asn Lys Asp Tyr Thr Ser Val Glu
        195                 200                 205

Gln Cys Glu Ile Ser Ile Ala Arg Lys Pro Val Val Ala His His His
    210                 215                 220

His His His
225


<210> SEQ ID NO 61
<211> LENGTH: 237
<212> TYPE: PRT
<213> ORGANISM: Acropora nobilis

<400> SEQUENCE: 61

Met Ser Tyr Ser Lys Gln Gly Ile Ala Gln Val Met Lys Thr Lys Tyr
1               5                   10                  15

His Met Glu Gly Ser Val Asn Gly His Glu Phe Thr Ile Glu Gly Val
            20                  25                  30

Gly Thr Gly Asn Pro Tyr Glu Gly Thr Gln Met Ser Glu Leu Val Ile
        35                  40                  45
```

```
Thr Lys Pro Ala Gly Lys Pro Leu Pro Phe Ser Phe Asp Ile Leu Ser
    50                  55                  60

Thr Val Phe Gln Tyr Gly Asn Arg Cys Phe Thr Lys Tyr Pro Glu Gly
65                  70                  75                  80

Met Thr Asp Tyr Phe Lys Gln Ala Phe Pro Asp Gly Met Ser Cys Glu
                85                  90                  95

Arg Ser Phe Leu Tyr Glu Asp Gly Gly Val Ala Thr Ala Ser Trp Asn
            100                 105                 110

Ile Arg Leu Glu Arg Asp Cys Phe Ile His Lys Ser Ile Tyr His Gly
        115                 120                 125

Val Asn Phe Pro Ala Asp Gly Pro Val Met Lys Lys Lys Thr Ile Gly
    130                 135                 140

Trp Asp Lys Ala Phe Glu Lys Met Thr Val Ser Lys Asp Val Leu Arg
145                 150                 155                 160

Gly Asp Val Thr Glu Phe Leu Met Leu Glu Gly Gly Gly Tyr His Ser
                165                 170                 175

Cys Gln Phe His Ser Thr Tyr Lys Pro Glu Lys Pro Ala Ala Leu Pro
            180                 185                 190

Pro Asn His Val Val Glu His His Ile Val Arg Thr Asp Leu Gly Gln
        195                 200                 205

Ser Ala Lys Gly Phe Thr Val Lys Leu Glu Glu His Ala Ala Ala His
    210                 215                 220

Val Asn Pro Leu Lys Val Gln His His His His His His
225                 230                 235


<210> SEQ ID NO 62
<211> LENGTH: 237
<212> TYPE: PRT
<213> ORGANISM: Acropora nobilis

<400> SEQUENCE: 62

Met Ser Tyr Ser Lys Gln Gly Ile Ala Gln Val Met Lys Thr Lys Tyr
1               5                   10                  15

His Met Glu Gly Ser Val Asn Gly His Glu Phe Thr Ile Glu Gly Val
            20                  25                  30

Gly Thr Gly Asn Pro Tyr Glu Gly Thr Gln Met Ser Glu Leu Val Ile
        35                  40                  45

Thr Lys Pro Ala Gly Lys Pro Leu Pro Phe Ser Phe Asp Ile Leu Ser
    50                  55                  60

Thr Val Phe Gln Tyr Gly Asn Arg Cys Phe Thr Lys Tyr Pro Glu Gly
65                  70                  75                  80

Met Thr Asp Tyr Phe Lys Gln Ala Phe Pro Asp Gly Met Ser Tyr Glu
                85                  90                  95

Arg Ser Phe Leu Tyr Glu Asp Gly Gly Val Ala Thr Ala Gly Trp Asn
            100                 105                 110

Ile Arg Leu Glu Arg Asp Cys Phe Ile His Lys Ser Ile Tyr His Gly
        115                 120                 125

Val Asn Phe Pro Ala Asp Gly Pro Val Met Lys Lys Lys Thr Ile Gly
    130                 135                 140

Trp Asp Lys Ala Phe Glu Lys Met Thr Val Ser Lys Asp Val Leu Arg
145                 150                 155                 160

Gly Asp Val Thr Gly Phe Leu Met Leu Glu Gly Gly Gly Tyr His Ser
                165                 170                 175

Cys Gln Phe His Ser Thr Tyr Lys Pro Glu Lys Pro Ala Ala Leu Pro
```

-continued

```
            180                 185                 190

Pro Asn His Val Val Glu His His Ile Val Arg Thr Asp Leu Gly Gln
        195                 200                 205

Ser Ala Lys Gly Phe Thr Val Lys Leu Glu Glu His Ala Ala Ala His
    210                 215                 220

Val Asn Pro Leu Lys Val Gln His His His His His His
225                 230                 235


<210> SEQ ID NO 63
<211> LENGTH: 237
<212> TYPE: PRT
<213> ORGANISM: Acropora nobilis

<400> SEQUENCE: 63

Met Ser Tyr Ser Lys Gln Gly Ile Ala Gln Glu Met Lys Thr Lys Tyr
1               5                   10                  15

His Met Glu Gly Ser Val Asn Gly His Glu Phe Thr Val Glu Gly Val
            20                  25                  30

Gly Thr Gly Tyr Pro Tyr Glu Gly Glu Gln Met Ser Glu Leu Val Ile
        35                  40                  45

Ile Glu Pro Ala Gly Lys Pro Leu Pro Phe Ser Phe Asp Ile Leu Ser
    50                  55                  60

Ser Val Phe Gln Tyr Gly Asn Arg Cys Phe Thr Lys Tyr Pro Ala Asp
65                  70                  75                  80

Met Pro Asp Tyr Phe Lys Gln Ala Phe Pro Asp Gly Met Ser Tyr Glu
                85                  90                  95

Arg Ser Phe Leu Phe Glu Asp Gly Ala Val Ala Thr Ala Ser Trp Lys
            100                 105                 110

Ile Arg Leu Glu Gly Asn Cys Phe Ile His Asn Ser Ile Phe Asn Gly
        115                 120                 125

Val Asn Phe Pro Ala Asp Gly Pro Val Met Glu Lys Lys Thr Ile Gly
    130                 135                 140

Trp Asp Lys Ser Phe Glu Lys Met Thr Val Ser Lys Glu Val Leu Arg
145                 150                 155                 160

Gly Asp Val Thr Met Phe Leu Met Leu Glu Gly Gly Gly Ser His Arg
                165                 170                 175

Cys Gln Phe His Ser Thr Tyr Lys Thr Glu Lys Pro Val Thr Leu Pro
            180                 185                 190

Pro Asn His Val Val Glu His Gln Ile Val Arg Thr Asp Leu Gly Gln
        195                 200                 205

Ser Ala Lys Gly Phe Thr Val Lys Leu Glu Ala His Ala Ala Ala His
    210                 215                 220

Val Asn Pro Leu Lys Val Lys His His His His His His
225                 230                 235


<210> SEQ ID NO 64
<211> LENGTH: 232
<212> TYPE: PRT
<213> ORGANISM: Agaricia fragilis

<400> SEQUENCE: 64

Met Ser Val Ile Val Lys Glu Met Met Thr Lys Leu His Met Glu Gly
1               5                   10                  15

Thr Val Asn Gly His Ala Leu Thr Ile Glu Gly Lys Gly Lys Gly Asp
            20                  25                  30

Pro Tyr Asn Gly Val Gln Ser Met Asn Leu Asp Val Lys Gly Gly Ala
```

-continued

```
        35                  40                  45

Pro Leu Pro Phe Ser Phe Asp Leu Leu Thr Pro Ala Phe Met Tyr Gly
    50                  55                  60

Asn Arg Val Phe Ala Lys Tyr Pro Glu Asp Ile Pro Asp Phe Phe Lys
65                  70                  75                  80

Gln Val Phe Pro Glu Gly Tyr His Trp Glu Arg Ser Ile Thr Phe Glu
                85                  90                  95

Asp Gln Ala Val Cys Thr Ala Thr Ser His Ile Arg Leu Asp Gln Lys
            100                 105                 110

Glu Met Cys Phe Ile Tyr Asp Val Arg Phe His Gly Val Asn Phe Pro
        115                 120                 125

Ala Asn Gly Pro Ile Met Gln Lys Lys Ile Leu Gly Trp Glu Pro Ser
    130                 135                 140

Thr Glu Lys Met Tyr Ala Arg Asp Gly Val Leu Lys Gly Asp Val Asn
145                 150                 155                 160

Met Thr Leu Arg Val Glu Gly Gly Gly His Tyr Arg Ala Asp Phe Arg
                165                 170                 175

Thr Thr Tyr Lys Ala Lys Lys Pro Val Asn Leu Pro Gly Tyr His Phe
            180                 185                 190

Ile Asp His Arg Ile Glu Ile Thr Lys His Ser Lys Asp Tyr Thr Asn
        195                 200                 205

Val Ala Leu Tyr Glu Ala Ala Val Ala Arg His Ser Pro Leu Pro Lys
    210                 215                 220

Val Ala His His His His His His
225                 230


<210> SEQ ID NO 65
<211> LENGTH: 306
<212> TYPE: PRT
<213> ORGANISM: Agaricia fragilis

<400> SEQUENCE: 65

Met Ser Val Ile Val Lys Glu Met Met Thr Lys Leu His Met Glu Gly
1               5                   10                  15

Thr Val Asn Gly His Ala Phe Thr Ile Glu Gly Lys Gly Lys Gly Asp
            20                  25                  30

Pro Tyr Asn Gly Val Gln Ser Met Asn Leu Asp Val Lys Gly Gly Ala
        35                  40                  45

Pro Leu Pro Phe Ser Phe Asp Leu Leu Thr Pro Ala Phe Met Tyr Gly
    50                  55                  60

Asn Arg Val Phe Thr Lys Tyr Pro Glu Asp Ile Pro Asp Phe Phe Lys
65                  70                  75                  80

Gln Val Phe Pro Glu Gly Tyr His Trp Glu Arg Ser Ile Thr Phe Glu
                85                  90                  95

Asp Gln Ala Val Cys Thr Ala Thr Ser His Ile Arg Leu Asp Gln Lys
            100                 105                 110

Glu Met Cys Phe Ile Tyr Asp Val Arg Phe His Gly Val Asn Phe Pro
        115                 120                 125

Ala Asn Gly Pro Ile Met Gln Lys Lys Ile Leu Gly Trp Glu Pro Ser
    130                 135                 140

Thr Glu Lys Met Tyr Ala Arg Asp Gly Val Leu Lys Gly Asp Val Asn
145                 150                 155                 160

Met Thr Leu Arg Val Glu Gly Gly Gly His Tyr Arg Ala Asp Phe Arg
                165                 170                 175
```

```
Thr Thr Tyr Lys Ala Lys Lys Pro Val Asn Leu Pro Gly Tyr His Phe
            180                 185                 190

Ile Asp His Arg Ile Glu Ile Thr Lys His Ser Lys Asp Tyr Thr Asn
        195                 200                 205

Val Ala Leu Tyr Glu Ala Ala Val Ala Arg His Ser Pro Leu Pro Lys
    210                 215                 220

Val Ala His His His His Ile Thr Asn Lys Ser Arg Gly His Gly Gly
225                 230                 235                 240

Arg Glu His Ala Thr Ser Gly Pro Ile Arg Pro Ile Val Ser Arg Ile
                245                 250                 255

Thr Ile His Trp Pro Ser Phe Tyr Asn Val Val Thr Gly Lys Thr Leu
            260                 265                 270

Ala Leu Pro Asn Leu Ile Ala Leu Gln His Ile Pro Leu Ser Pro Ala
        275                 280                 285

Gly Val Ile Ala Lys Arg Pro Ala Pro Ile Ala Leu Pro Asn Ser Cys
    290                 295                 300

Ala Ala
305


<210> SEQ ID NO 66
<211> LENGTH: 232
<212> TYPE: PRT
<213> ORGANISM: Agaricia fragilis

<400> SEQUENCE: 66

Met Ser Val Ile Val Lys Glu Met Met Thr Lys Leu His Met Glu Gly
1               5                   10                  15

Thr Val Asn Gly His Ala Phe Thr Ile Glu Gly Lys Gly Lys Gly Asp
            20                  25                  30

Pro Tyr Asn Gly Val Gln Ser Met Asn Leu Asp Val Lys Gly Gly Ala
        35                  40                  45

Pro Leu Pro Phe Ser Phe Asp Leu Leu Thr Pro Ala Phe Met Tyr Gly
    50                  55                  60

Asn Arg Val Phe Thr Lys Tyr Pro Glu Asp Ile Pro Asp Phe Phe Lys
65                  70                  75                  80

Gln Val Phe Pro Glu Gly Tyr His Trp Glu Arg Ser Ile Thr Phe Glu
                85                  90                  95

Asp Gln Ala Val Cys Thr Ala Thr Ser His Ile Arg Leu Asp Gln Lys
            100                 105                 110

Glu Met Cys Phe Ile Tyr Asp Val Arg Phe His Gly Val Asn Phe Pro
        115                 120                 125

Ala Asn Gly Pro Ile Met Gln Lys Lys Ile Leu Gly Trp Glu Pro Ser
    130                 135                 140

Thr Glu Lys Met Tyr Ala Arg Asp Gly Val Leu Lys Gly Asp Val Asn
145                 150                 155                 160

Met Thr Leu Arg Val Glu Gly Gly Gly His Tyr Arg Ala Asp Phe Arg
                165                 170                 175

Thr Thr Tyr Lys Ala Lys Lys Pro Val Asn Leu Pro Gly Tyr His Phe
            180                 185                 190

Ile Asp His Arg Ile Glu Ile Thr Lys His Ser Lys Asp Tyr Thr Asn
        195                 200                 205

Val Ala Leu Tyr Gly Ala Ala Val Ala Arg His Ser Pro Leu Pro Lys
    210                 215                 220

Val Ser His His His His His His
225                 230
```

-continued

```
<210> SEQ ID NO 67
<211> LENGTH: 232
<212> TYPE: PRT
<213> ORGANISM: Agaricia fragilis

<400> SEQUENCE: 67

Met Ser Val Ile Val Lys Glu Met Met Thr Lys Leu His Met Glu Gly
1               5                   10                  15

Thr Val Asn Gly His Ala Phe Thr Ile Glu Gly Lys Gly Lys Gly Asp
            20                  25                  30

Pro Tyr Asn Gly Val Gln Ser Met Asn Leu Asp Val Lys Gly Gly Ala
        35                  40                  45

Pro Leu Pro Phe Ser Phe Asp Leu Leu Thr Pro Ala Phe Met Tyr Gly
    50                  55                  60

Asn Arg Val Phe Thr Lys Tyr Pro Glu Asp Ile Pro Asp Phe Phe Lys
65                  70                  75                  80

Gln Val Phe Pro Glu Gly Tyr His Trp Glu Arg Ser Ile Thr Phe Glu
                85                  90                  95

Asp Gln Ala Val Cys Thr Ala Thr Ser His Ile Arg Leu Asp Gln Lys
            100                 105                 110

Glu Met Cys Phe Ile Tyr Asp Val Arg Phe His Gly Val Asn Phe Pro
        115                 120                 125

Ala Asn Gly Pro Ile Met Gln Lys Lys Ile Leu Gly Trp Glu Pro Ser
    130                 135                 140

Thr Glu Lys Met Tyr Ala Arg Asp Gly Val Leu Lys Gly Asp Val Asn
145                 150                 155                 160

Val Thr Leu Arg Val Glu Gly Gly Gly His Tyr Arg Ala Asp Phe Arg
                165                 170                 175

Thr Thr Tyr Lys Ala Lys Lys Pro Val Asn Leu Pro Gly Tyr His Phe
            180                 185                 190

Ile Asp His Arg Ile Glu Ile Thr Lys His Ser Lys Asp Tyr Thr Asn
        195                 200                 205

Val Ala Leu Tyr Glu Ala Ala Val Ala Arg His Ser Pro Leu Pro Lys
    210                 215                 220

Val Ala His His His His His His
225                 230


<210> SEQ ID NO 68
<211> LENGTH: 232
<212> TYPE: PRT
<213> ORGANISM: Agaricia fragilis

<400> SEQUENCE: 68

Met Ser Val Ile Val Lys Glu Met Met Thr Lys Leu His Met Glu Gly
1               5                   10                  15

Thr Val Asn Gly His Ala Phe Thr Ile Glu Gly Lys Gly Glu Gly Asp
            20                  25                  30

Pro Tyr Asn Gly Val Gln Ser Met Asn Leu Asp Val Lys Gly Gly Ala
        35                  40                  45

Pro Leu Pro Phe Ser Phe Asp Leu Leu Thr Pro Ala Phe Met Tyr Gly
    50                  55                  60

Asn Arg Val Phe Thr Lys Tyr Pro Glu Asp Ile Pro Asp Phe Phe Lys
65                  70                  75                  80

Gln Val Phe Pro Glu Gly Tyr His Trp Glu Arg Ser Ile Thr Phe Glu
                85                  90                  95
```

-continued

```
Asp Gln Ala Val Cys Thr Ala Thr Ser His Ile Arg Leu Asp Gln Lys
            100                 105                 110

Glu Met Cys Phe Ile Tyr Asp Val Arg Phe His Gly Val Asn Phe Pro
        115                 120                 125

Ala Asn Gly Pro Ile Met Gln Lys Lys Ile Leu Gly Trp Glu Pro Ser
    130                 135                 140

Thr Glu Lys Met Tyr Ala Arg Asp Gly Val Leu Lys Gly Asp Val Asn
145                 150                 155                 160

Met Thr Leu Arg Val Glu Gly Gly Gly His Tyr Arg Ala Asp Phe Arg
                165                 170                 175

Thr Thr Tyr Lys Ala Lys Lys Pro Val Asn Leu Pro Gly Tyr His Phe
            180                 185                 190

Ile Asp His Arg Ile Glu Ile Thr Lys His Ser Lys Asp Tyr Thr Asn
        195                 200                 205

Val Ala Leu Tyr Gly Ala Ala Val Ala Arg His Ser Pro Leu Pro Lys
    210                 215                 220

Val Ala His His His His His His
225                 230


<210> SEQ ID NO 69
<211> LENGTH: 232
<212> TYPE: PRT
<213> ORGANISM: Agaricia fragilis

<400> SEQUENCE: 69

Met Ser Val Ile Val Lys Glu Met Met Thr Lys Leu His Met Glu Gly
1               5                   10                  15

Thr Val Asn Gly His Ala Phe Thr Ile Glu Gly Lys Gly Lys Gly Asp
            20                  25                  30

Pro Tyr Asn Gly Val Gln Ser Met Asn Leu Asp Val Lys Gly Gly Ala
        35                  40                  45

Pro Leu Pro Phe Ser Phe Asp Leu Leu Thr Pro Ala Phe Met Tyr Gly
    50                  55                  60

Asn Arg Val Phe Thr Lys Tyr Pro Glu Asp Ile Pro Asp Phe Phe Lys
65                  70                  75                  80

Gln Val Phe Pro Glu Gly Tyr His Trp Glu Arg Ser Ile Thr Phe Glu
                85                  90                  95

Asp Gln Ala Val Cys Thr Ala Thr Ser His Ile Arg Leu Asp Gln Lys
            100                 105                 110

Glu Met Cys Phe Ile Tyr Asp Val Arg Phe His Gly Val Asn Phe Pro
        115                 120                 125

Ala Asn Gly Pro Ile Met Gln Lys Lys Ile Leu Gly Trp Glu Pro Ser
    130                 135                 140

Thr Glu Lys Met Tyr Ala Arg Asp Gly Val Leu Lys Gly Asp Val Asn
145                 150                 155                 160

Met Thr Leu Arg Val Glu Gly Gly Gly His Tyr Arg Ala Asp Phe Arg
                165                 170                 175

Thr Thr Tyr Lys Ala Lys Lys Pro Val Asn Leu Pro Gly Tyr His Phe
            180                 185                 190

Ile Asp His Arg Ile Glu Ile Thr Lys His Ser Lys Asp Tyr Thr Asn
        195                 200                 205

Val Ala Leu Tyr Glu Ala Ala Val Ala Arg His Ser Pro Leu Pro Lys
    210                 215                 220

Val Ala His His His His His His
```

```
225                 230


<210> SEQ ID NO 70
<211> LENGTH: 232
<212> TYPE: PRT
<213> ORGANISM: Agaricia fragilis

<400> SEQUENCE: 70

Met Ser Val Ile Val Lys Glu Met Met Thr Lys Leu His Met Glu Gly
1               5                   10                  15

Thr Val Asn Gly His Ala Phe Thr Ile Glu Gly Lys Gly Lys Gly Asp
            20                  25                  30

Pro Tyr Asn Gly Val Gln Ser Met Asn Leu Asp Val Lys Gly Gly Ala
        35                  40                  45

Pro Leu Pro Phe Ser Phe Asp Leu Leu Thr Pro Ala Phe Met Tyr Gly
    50                  55                  60

Asn Arg Val Phe Thr Lys Tyr Pro Glu Asp Ile Pro Asp Phe Phe Lys
65                  70                  75                  80

Gln Val Phe Pro Glu Gly Tyr His Trp Glu Arg Ser Ile Thr Phe Glu
                85                  90                  95

Asp Gln Ala Val Cys Thr Ala Thr Ser His Ile Arg Leu Asp Gln Lys
            100                 105                 110

Glu Met Cys Phe Ile Tyr Asp Val Arg Phe His Gly Val Asn Phe Pro
        115                 120                 125

Ala Asn Gly Pro Ile Met Gln Lys Lys Ile Leu Gly Trp Glu Pro Ser
    130                 135                 140

Thr Glu Lys Met Tyr Ala Arg Asp Gly Val Leu Lys Gly Asp Val Asn
145                 150                 155                 160

Thr Thr Leu Arg Val Glu Gly Gly Gly His Tyr Arg Ala Asp Phe Arg
                165                 170                 175

Thr Thr Tyr Lys Ala Lys Lys Pro Val Asn Leu Pro Gly Tyr His Phe
            180                 185                 190

Ile Asp His Arg Ile Glu Ile Thr Lys His Ser Lys Asp Tyr Thr Asn
        195                 200                 205

Val Ala Leu Tyr Glu Ala Ala Val Ala Arg His Ser Pro Leu Pro Lys
    210                 215                 220

Val Ala His His His His His His
225                 230


<210> SEQ ID NO 71
<211> LENGTH: 717
<212> TYPE: DNA
<213> ORGANISM: Acropora aculeus

<400> SEQUENCE: 71

atgtcttatt caaagcaggg catcgtacaa gaaatgaaga cgaaataccg tatggaaggc      60

agtgtcaatg gccatgaatt cacgatcgaa ggtgtaggaa ctgggtaccc ttacgaaggg     120

aaacagatgt ccgaattagt gatcatcaag cctaagggaa agccccttcc attctccttt     180

gacatactgt catcagtctt tcaatatgga aacaggtgct tcacaaagta ccctgcagac     240

atgcctgact atttcaagca agcattccca gatggaatgt catatgaaag gtcatttcta     300

tttgaggatg gagcagttgc tacagccagc tggaacattc gtctcgaagg aaattgcttc     360

atccacaatt ccatctttca tggcgtaaac tttcccgatg atggacccgt aatgaaaaag     420

aagacaattg gctgggataa gtccttcgaa aaaatgactg tgtctaaaga ggtgttaaga     480
```

-continued

```
ggtgatgtga ctatgtttct tatgctcgaa ggaggtggtt accacagatg ccagtttcac    540

tccacttaca aaacagagaa gccggtcgaa ctgcccccga atcatgtcgt agaacatcaa    600

attgtgagga ccgaccttgg ccaaagtgca aaaggcttca cggtcaagct ggaagcacat    660

gctgcggctc atgttaaccc tttgaaggtt caacagcacc atcaccatca ctaataa       717
```

<210> SEQ ID NO 72
<211> LENGTH: 717
<212> TYPE: DNA
<213> ORGANISM: Acropora aculeus

<400> SEQUENCE: 72

```
atgtctcttt caaagcatgg catcacacaa gaaatgccga cgaaatacca tatgaaaggc     60

agtgtcaatg gccatgaatt cgagatcgaa ggtgtaggaa ctggacaccc ttacgaaggg    120

acacacatgg ccgaattagt gatcataaag cctgcgggaa aaccccttcc attctccttt    180

gacatactgt caacagtcat tcaatacgga aacagatgct tcactaagta ccctgcagac    240

ctgcctgact atttcaagca agcataccca ggtggaatgt catatgaaag gtcatttgtg    300

tatcaggatg gaggaattgc tacagcgagc tggaacgtta gtctcgaggg aaattgcttc    360

atccacaaat ccacctatct tggtgtaaac tttcctgctg atggacccgt aatgacaaag    420

aagacaattg gctgggataa agcctttgaa aaaatgactg ggttcaatga ggtgttaaga    480

ggtgatgtga ctgagtttct tatgctcgaa ggaggtggtt accattcatg ccagtttcac    540

tccacttaca aaccagagaa gccggtcgaa ctgcccccga atcatgtcat agaacatcac    600

attgtgagga ccgaccttgg caagactgca aaaggcttca tggtcaagct ggtacaacat    660

gctgcggctc atgttaacac tttgaaggtt caacatcacc atcaccatca ctaataa       717
```

<210> SEQ ID NO 73
<211> LENGTH: 665
<212> TYPE: DNA
<213> ORGANISM: Acropora aculeus

<400> SEQUENCE: 73

```
atggaaggca gtgtcaatgg ccatgaattc acgatcgaag gtgtaggaac tgggtaccct     60

tacgaaggga agcagatgtc cgaattagtg atcgtcaagc ctaagggaaa gccccttcca    120

ttctcctttg acatactgtc atcagtcttt caatatggaa acaggtgctt cacaaagtac    180

cctgcagaca tgcctgacta tttcaagcaa gcattcccag atggaatgtc atatgaaagg    240

tcatttctat ttgaggatgg agcagttgct acagccagct ggaacattcg tctcgaagga    300

aattgcttca tccacaattc catctttcat ggcgtaaact ttcccgctga tggacccgta    360

atgaaaaaga agacaattgg ctgggataag tccttcgaaa aaatgactgt gtctaaagag    420

gtgttaagag gtgatgtgac tatgtttctt atgctcgaag gaggtggtta ccacagatgc    480

cagtttcact ccacttacaa aacagtgaag ccggtcgaac tgcccccgaa tcatgtcgta    540

gaacatcaaa ttgtgaggac cgaccttggc caaagtgcaa aaggcttcac agtcaagctg    600

gaagcacatg ctgcggctca tgtaaccctt tgaaggttca acatcaccat caccatcact    660

aataa                                                                665
```

<210> SEQ ID NO 74
<211> LENGTH: 717
<212> TYPE: DNA
<213> ORGANISM: Acropora aculeus

<400> SEQUENCE: 74

```
atgtctcttt caaagcatgg catcacacaa gaaatgccga cgaaatacca tatgaaaggc     60

agtgtcaatg gccatgaatt cgagatcgaa ggtgtaggaa ctggacaccc ttacgaaggg    120

acacacatgg ccgaattagt gatcataaag cctgcgggaa aaccccttcc attctccttt    180

gacatactgt caacagtcat tcaatacgga aacagatgct tcactaagta ccctgcagac    240

ctgcctgact atttcaagca agcataccca ggtggaatgt catatgaaag gtcatttgta    300

tttcaggatg gaggaattgc tacagcgagc tggaacgtcg gtctcgaggg aaattgcttc    360

atccacaaat ccacctatct tggtgtaaac tttcctgctg atggacccgt aatgacaaag    420

aagacaattg gctgggataa agcctttgaa aaaatgactg ggttcaatga ggtgttaaga    480

ggtgatgtga ctgagtttct tatgctcgaa ggaggtggtt accattcatg ccagtttcac    540

tccacttaca aaccagagaa gccggtcaaa ctgcccccga atcatgtcat agaacatcac    600

attgtgagga ccgaccttgg caagactgca aaaggcttca tggtcaagct ggtacaacat    660

gctgcggctc atgttaaccc tttgaaggtt caacatcacc atcaccatca ctaataa       717
```

```
<210> SEQ ID NO 75
<211> LENGTH: 717
<212> TYPE: DNA
<213> ORGANISM: Acropora aculeus

<400> SEQUENCE: 75

atgtctcttt caaagcatgg catcacacaa gaaatgccga cgaaatacca tatgaaaggc     60

aatgtcaatg gccatgaatt cgagatcgaa ggtgtaggaa ctggacaccc ttacgaaggg    120

acacacatgg ccgaattagt gatcataaag cctgcgggaa aaccccttcc attctccttt    180

gacatactgt caacagtcat tcaatacgga aacagatgct tcactaagta ccctgcagac    240

ctgcctgact atttcaagca agcgtaccca ggtggaatgt catatgaaag gtcatttgta    300

tttcaggatg gaggaattgc tacagcgagc tggaacgttg gtctcgaggg aaattgcttc    360

atccacaaat ccacctatct tggtgtaaac tttcctgctg atggacccgt aatgacaaag    420

aagacaattg gctgggataa agcctttgaa aaaatgactg ggttcaatga ggtgttaaga    480

ggcgatgtga ctgggtttct tatgctcgaa ggaggtggtt accattcatg ccagtttcac    540

tccacttaca aaccagagaa gccggtcaaa ctgcccccga atcatgtcat agaacatcac    600

attgtgagga ccgaccttgg caagactgca aaaggcttca tggtcaagct ggtacaacat    660

gctgcggctc atgtgaaccc tttgaaggtt caacatcacc atcaccatca ctaataa       717
```

```
<210> SEQ ID NO 76
<211> LENGTH: 666
<212> TYPE: DNA
<213> ORGANISM: Acropora aculeus

<400> SEQUENCE: 76

atgacctaca aggtttatat gtcaggcacg gtcaatggac attactttga ggtcgaaggc     60

gatggaaaag gaaagcctta cgagggggag cagacggtga agctcactgt caccaaggga    120

ggacctctgc catttgcttg ggatatttta tcaccacagt cacagtacgg aagcatacca    180

ttcaccaaat accctgacga catccctgac tatgtaaagc agtcattccc ggagggatat    240

acatgggaga ggatcatgaa ctttgaagat ggtgcagtgt gtactgtcag caatgattcc    300

agcatccaag gcaactgttt catctacaat gtcaagttct ctggtttgaa ctttcctccc    360

aatggaccgg ttatgcagaa gaagacacag ggctgggaac ccaacactga gcgtctcttt    420
```

-continued

```
gcacgagatg gaatgctgat aggaaacaac tttatggctc tgaagttaga aggaggtggt    480
cactatttgt gtgaattcaa atctacttac aaggcaaaga agcctgtgag gatgccaggg    540
tatcactatg ttgaccgcaa actggatgta accaatcaca acagggatta cacttccgtt    600
gagcagcgtg aaatttccat tgcacgcaaa cctgtggtcg cccatcacca tcaccatcac    660
taataa                                                               666
```

<210> SEQ ID NO 77
<211> LENGTH: 687
<212> TYPE: DNA
<213> ORGANISM: Acropora aculeus

<400> SEQUENCE: 77

```
atgagtgtga tcgctaaaca aatgacctac aaggtttata tgtcaggcac ggtcaatgga     60
cattactttg aggtcgaagg cgatggaaaa ggaaagcctt acgaggggga gcagacggtg    120
aagctcactg tcaccaaggg aggacctctg ccatttgctt gggatatttt atcaccgcag    180
tcacagtacg gaagcatacc attcaccaaa taccctgacg acatccctga ctatgtaaag    240
cagtcattcc cggagggata tacatgggag aggatcatga actttgagga tggtgcagtg    300
tgtactgtca gcaatgattc cagcatccaa ggcaactgtt tcatctacaa tgtcaagttc    360
tctggtttga actttcctcc caatggaccg gttatgcgga agaagacacg gggctgggaa    420
cccaacactg agcgtctctt tgcacgggat ggaatgctga taggaaacaa ctttatggct    480
ctgaagttag aaggaggtgg tcactatttg tgtgaattca aatctactta caaggcaaag    540
aagcctgtga ggatgccagg gtatcactat gttgaccgca aactggatgt aaccaatcac    600
aacagggatt acacttccgt tgagcagtgt gaaatttcca ttgcacgcaa acctgtggtc    660
gcccatcacc atcaccatca ctaataa                                        687
```

<210> SEQ ID NO 78
<211> LENGTH: 666
<212> TYPE: DNA
<213> ORGANISM: Acropora hyacinthus

<400> SEQUENCE: 78

```
atgacctaca aggtttatat gtcaggcacg gtcaatggac actactttga ggtcgaaggc     60
gatggaaaag gaaagcctta cgagggggag caaacggtaa ggctgactgt caccaagggc    120
ggacctctgc cgtttgcttg ggatatttta tcaccacagt cacagtacgg aagcatacca    180
ttcaccaagt accctgaaga catccctgac tatgtgaagc agtcattccc ggagggatat    240
acatgggaga ggatcatgaa ctttgaagat ggtgcagtgt gtactgtcag caatgattcc    300
agcatccaag gcaactgttt catctaccat gtcaagttct ctggtttgaa ctttcctccc    360
aatggacctg ttatgcagaa gaagacacag ggctgggaac ccaacactga gcgtctcttt    420
gcacgagatg gagttctgat aggaaacaac tttatggccc tgaagttaga aggaggtggt    480
cactatttgt gtgaattcaa atctacttac aaggcaaaga agcctgtgaa gatgcctggg    540
tatcactttg ttgaccgcaa actggatgta accaatcaca acaaggatta cacttctgtt    600
gagcagcgtg aaatttccat tgcacgcaaa cctgtggtcg cccaccacca tcaccatcac    660
taataa                                                               666
```

<210> SEQ ID NO 79
<211> LENGTH: 684
<212> TYPE: DNA
<213> ORGANISM: Acropora millepora

<400> SEQUENCE: 79

```
atgaagacga aataccatat ggaaggcagt gtcaatggcc atgaattcac gatcgaaggt     60
gtaggaactg gaaaccctta cgaaggcaca cagatgtccg aattagtgat caccgagcct    120
gcaggaaaac cccttccatt ctcctttgac attctgtcaa cagtctttca gtatggaaac    180
aggtgcttca caaagtaccc tgaaggaatg actgactatt tcaagcaagc attcccagat    240
ggaatgtcat ttgaaaggtc atttctatat gaggatggag gagttgctac agccagctgg    300
aacattcgtc ttgagagaga ttgcttcatc cacaaatcca tctatcatgg cgttaacttt    360
cccgctgatg gacccgtaat gaaaaagaag accattggct gggataaagc cttcgaaaaa    420
atgactgtgt ccaaagacgt tttaagaggt gatgtgactg agtttcttat gctcgaagga    480
ggtggttacc acagctgcca gtttcactcc acttacaaac cagagaagcc ggttacactg    540
ccccctaatc atgtcgtgga acatcacatt gtgaggactg accttggcca aactgcaaaa    600
ggcttcacag tcaagctgga agaacatgct gcggctcatg ttaacccttt gaaggttcac    660
catcaccatc accatcacta ataa                                           684
```

<210> SEQ ID NO 80
<211> LENGTH: 681
<212> TYPE: DNA
<213> ORGANISM: Acropora millepora

<400> SEQUENCE: 80

```
atgtcttatt caaagcaagg catcgtacaa gaaatgaaga cgaaatacca tatggaaggc     60
agtgtcaatg gccatgaatt cacgatcgaa ggtgtaggaa ctgggtaccc ttacgaaggg    120
aaacagatat ccgaattagt gatcatcaag cctgcgggaa aaccccttcc attctccttt    180
gacatactgt catcagtctt tcaatatgga aacaggtgct tcacaaagta ccctgcagac    240
atgcctgact atttcaagca agcattccca gatggaatgt catatgaaag gtcatttcta    300
tttgaggatg gagcagttgc cacagccagc tggaacattc gtctcgaagg aaattgcttc    360
atccacaaat ccatctttca tggcgtaaac tttcccgctg atggacccgt aatgaaaaag    420
aagacaattg actgggataa gtccttcgaa aaaatgactg tgtctaaaga ggtgctaaga    480
ggtgacgtga ctatgtttct tatgctcgaa ggaggtggtt ctcacagatg ccaatttcac    540
tccacttaca aaacagagaa gccggtcaca ctgcccccga atcatgtcgt agaacatcaa    600
attgtgagga ccgaccttgg ccaaactgca aaaggcttca cagtcaagct ggaagaacat    660
gctgcggctc atgttagcct a                                              681
```

<210> SEQ ID NO 81
<211> LENGTH: 684
<212> TYPE: DNA
<213> ORGANISM: Acropora millepora

<400> SEQUENCE: 81

```
atgtcttatt caaagcaagg catcgtacaa gaaatgaaga cgaaatacca tatggaaggc     60
agtgtcaatg gccatgaatt cacgatcgaa ggtgtaggaa ctgggtaccc ttacgaaggg    120
aaacagatgt ccgaattagt gatcatcaag cctgcgggaa aaccccttcc attctccttt    180
gacatactgt catcagtctt tcaatatgga aacaggtgct tcacaaagta ccctgcagac    240
atgcctgact atttcaagca agcattccca gatggaatgt catatgaaag gtcatttcta    300
tttgaggatg gagcagttgc cacagccagc tggaacattc gtctcgaagg aaattgcttc    360
```

```
atccacaaat ccatctttca tggcgtaaac tttcccgctg atggacccgt aatgaaaaag    420

aagacaattg actgggataa gtccttcgaa aaaatgactg tgtctaaaga ggtgctaaga    480

ggtgacgtga ctatgtttct tatgctcgaa ggaggtggtt ctcacagatg ccaatttcac    540

tccacttaca aaacagagaa gccggtcaca ctgcccccga atcatgtcgt agaacatcaa    600

attgtgagga ccgaccttgg ccaaactgca aaaggcttca cagtcaagct ggaagaacat    660

gctgcggctc atgtaaccct ttga                                           684
```

<210> SEQ ID NO 82
<211> LENGTH: 717
<212> TYPE: DNA
<213> ORGANISM: Acropora millepora

<400> SEQUENCE: 82

```
atgtcttatt caaagcaggg catcgtacaa gaaatgaaga cgaaataccg tatggaaggc     60

agtgtcaatg gccatgaatt cacgatcgaa ggtgtaggaa ctgggtaccc ttacgaaggg    120

aagcagatgt ccgaattagt gatcgtcaag cctaagggaa agccccttcc attctccttt    180

gacatactgt catcagtctt tcaatatgga aacaggtgct tcacaaagta ccctgcagac    240

atgcctgact atttcaagca agcattccca gatggaatgt catatgaaag gtcatttcta    300

tttgaggatg gagcagttgc tacagccagc tggaacattc gtctcgaagg aaattgcttc    360

atccacaatt ccatctttca tggcgtaaac tttcccgctg atggacccgt aatgaaaaag    420

aagacaattg gctgggataa gtccttcgaa aaaatgactg tgtctaaaga ggtgttaaga    480

ggtgatgtga ctatgtttct tatgctcgaa ggaggtggtt accacagatg ccagtttcac    540

tccacttaca aaacagtgaa gccggtcgaa ctgcccccga atcatgtcgt agaacatcaa    600

attgtgagga ccgaccttgg ccaaagtgca aaaggcttca cagtcaagct ggaagcacat    660

gctgcggctc atgttaaccc tttgaaggtt caacatcacc atcaccatca ctaataa       717
```

<210> SEQ ID NO 83
<211> LENGTH: 717
<212> TYPE: DNA
<213> ORGANISM: Acropora millepora

<400> SEQUENCE: 83

```
atgtctcatt caaagcaagg catcgcacaa gtaatgaaga cgaaatacca tatggaaggc     60

agtgtcaatg gccatgaatt cacgatcgaa ggtgtaggaa ctggaaaccc ttacgaaggc    120

tcacagatgt ccgagttagt gatcaccaag cctgcaggaa aaccccttcc attctccttt    180

gacattctct caacagtctt tcaatatgga aacaggtgct tcacaaagta ccctgaagga    240

atgactgact atttcaagca agcattccca gatggaatgt catatgaaag gtcatttcta    300

tatgaggatg gaggagttgc tacagccagc tggaacattc gtcttgagag aggttgcttc    360

atccacaaat ccatctatca tggcgttaac tttcccgctg atggacccgt aatgaaaaag    420

aagaccattg gctgggataa ggccttcgaa aaaatgactg tgtccaaaga cgtgttaaga    480

ggtgatgtga ctgggtttct tatgctcgaa ggaggtggtt accacaactg ccagtttcac    540

tccacttaca aaccagaaaa gccggttaca ctgcccccga atcatgtcgt ggaacatcac    600

attgtgagga ctgaccttgg ccaaactgca aaaggcttca cagccaagct ggaagaacat    660

gctgcggctc atgtaaaccc tttgaaggtt caacatcacc atcaccatca ctaataa       717
```

<210> SEQ ID NO 84
<211> LENGTH: 684

<212> TYPE: DNA
<213> ORGANISM: Acropora millepora

<400> SEQUENCE: 84
atgaagacga aataccatat ggaaggcagt gtcaatggcc atgaattcac gatcgaaggt 60
gtaggaactg ggtaccctta cgaagggaaa cagatgtccg aattagtgat catcaagcct 120
gcgggaaaac cccttccatt ctcctttgac atactgtcat cagtctttca atatggaaac 180
aggtgcttca caaagtaccc tgcagacatg cctgactatt tcaagcaagc attcccagat 240
ggaatgtcat atgaaaggtc atttctattt gaggatggag cagttgctac agccagctgg 300
aacattcgtc tcgaaggaaa ttgcttcatc cacaaatcca tctttcatgg cgtaaacttt 360
cccgctgatg gacccgtaat gaaaaagaag acaattgact gggataagtc cttcgaaaaa 420
atgactgtgt ctaaagaggt gctaagaggt gacgtgacta tgtttcttat gctcgaagga 480
ggtggttctc acagatgcca atttcactcc acttacaaaa cagagaagcc ggtcacactg 540
cccccgaatc atgtcgtaga acatcaaatt gtgaggaccg accttggcca aagtgcaaaa 600
ggctttacag tcaagctgga agcacatgct gcggctcatg ttaacccttt gaaggttaaa 660
catcaccatc accatcacta ataa 684

<210> SEQ ID NO 85
<211> LENGTH: 687
<212> TYPE: DNA
<213> ORGANISM: Acropora millepora

<400> SEQUENCE: 85
atgacgatga aataccacat ggaagggtct gtcgatgggc ataaatttgt gatcacgggc 60
cacggcaatg gaaatccttt cgaagggaaa cagactatga atctgtgtgt ggttgaaggg 120
ggacccctgc cattctccga agacattttg tctgctacgt ttgactacgg aaacagggtc 180
ttcactgaat atcctcaagg catggttgac tttttcaaga attcatgtcc agctggatac 240
acatggcaca ggtctttact ctttgaagat ggagcagttt gcacaactag tgcagatata 300
acagtgagtg ttgaggagaa ctgcttttat cacaattcca agtttcatgg agtgaacttt 360
cctgctgatg gacctgtgat gaaaaagatg acaactaatt gggagccatc ctgcgagaaa 420
atcataccag tacctagaca ggggatattg aaaggggata ttgccatgta cctccttctg 480
aaggatggtg ggcgttatcg gtgccagttc gacacaattt acaaagcaaa gtctgacccg 540
aaagagatgc cggagtggca cttcatccaa cataagctca cccgggaaga ccgcagcgat 600
gctaagaacc agaaatggca actggtagaa catgctgttg cttcccgatc cgcattgccc 660
ggacatcacc atcaccatca ctaataa 687

<210> SEQ ID NO 86
<211> LENGTH: 666
<212> TYPE: DNA
<213> ORGANISM: Acropora millepora

<400> SEQUENCE: 86
atgacctaca aggtttatat gtcaggcacg gtcaatggac actactttga ggtcgaaggc 60
gatggaaaag gtaagcccta cgagggggag cagacggtaa agctcactgt caccaagggc 120
ggacctctgc catttgcttg ggatatttta tcaccacagt gtcagtacgg aagcatacca 180
ttcaccaagt accctgaaga catccctgac tatgtaaagc agtcattccc ggagggctat 240
acatgggaga ggatcatgaa ctttgaagat ggtgcagtgt gtactgtcag caatgattcc 300

-continued

```
agcatccaag gcaactgttt catctaccat gtcaagttct ctggtttgaa ctttcctccc    360

aatggacctg tcatgcagaa gaagacacag ggctgggaac ccaacactga gcgtctcttt    420

gcacgagatg gaatgctgct aggaaacaac tttatggctc tgaagttaga aggaggcggt    480

cactatttgt gtgaattcaa aactacttac aaggcaaaga agcctgtgaa gatgccaggg    540

tatcactatg ttgaccgcaa actggatgta accaatcaca acaaggatta cacttcggtt    600

gagcagtgtg aaatttccat tgcacgcaaa cctgtggtcg cccatcacca tcaccatcac    660

taataa                                                                666
```

<210> SEQ ID NO 87
<211> LENGTH: 717
<212> TYPE: DNA
<213> ORGANISM: Acropora nobilis

<400> SEQUENCE: 87

```
atgtcttatt caaagcaagg catcgcacaa gtaatgaaga cgaaatacca tatggaaggc     60

agtgtcaatg gccatgaatt cacgatcgaa ggtgtaggaa ctggaaaccc ttacgaaggc    120

acacagatgt ccgaattagt gatcaccaag cctgcaggaa aacccccttcc attctccttt    180

gacattctgt caacagtctt tcaatatgga aacaggtgct tcacaaagta ccctgaagga    240

atgactgact atttcaagca agcattccca gatggaatgt catgtgaaag gtcatttcta    300

tatgaggatg gaggagttgc tacagccagc tggaacattc gtcttgagag agattgcttc    360

atccacaaat ccatctatca tggcgttaac tttcccgctg atggacccgt aatgaaaaag    420

aagaccattg gctgggataa agccttcgaa aaaatgactg tgtccaaaga cgtgttaaga    480

ggtgatgtga ctgagtttct tatgctcgaa ggaggtggtt accacagctg ccagtttcac    540

tccacttaca aaccagaaaa gccggctgca ctgcccccga atcatgtcgt agaacatcac    600

attgtgagga ctgaccttgg ccaaagtgca aaaggcttca cagtcaagct ggaagaacat    660

gctgcggctc atgttaaccc tttgaaggtt caacatcacc atcaccatca ctaataa       717
```

<210> SEQ ID NO 88
<211> LENGTH: 684
<212> TYPE: DNA
<213> ORGANISM: Acropora nobilis

<400> SEQUENCE: 88

```
atgaagacga aataccatat ggaaggcagt gtcaatggcc atgaattcac gatcgaaggt     60

gtaggaactg gaaaccctta cgaaggcaca cagatgtccg aattggtgat caccaagcct    120

gcaggaaaac cccttccatt ctcctttgac attctgtcaa cagtctttca atatggaaac    180

aggtgcttca caaagtaccc tgaaggaatg actgactatt tcaagcaagc attcccagat    240

ggaatgtcat atgaaaggtc atttctatat gaggatggag gagttgctac agccggctgg    300

aacattcgtc ttgagagaga ttgcttcatc cacaaatcca tctatcatgg cgttaacttt    360

cccgctgatg gacccgtaat gaagaagaag accattggct gggataaagc cttcgaaaaa    420

atgactgtgt ccaaagacgt gttaagaggt gatgtgactg ggtttcttat gctcgaagga    480

ggtggttacc acagctgcca gtttcactcc acttacaaac cagaaaagcc ggctgcactg    540

cccccgaatc atgtcgtaga acatcacatt gtgaggactg accttggcca aagtgcaaaa    600

ggcttcacag tcaagctgga agaacatgct gcggctcatg ttaacccttt gaaggttcaa    660

catcaccatc accatcacta ataa                                            684
```

<210> SEQ ID NO 89
<211> LENGTH: 684
<212> TYPE: DNA
<213> ORGANISM: Acropora nobilis

<400> SEQUENCE: 89
atgaagacga aataccatat ggaaggcagt gtcaatggcc atgaattcac ggtcgaaggt 60
gtagggactg ggtaccctta cgaaggggaa cagatgtccg aattagtgat catcgagcct 120
gcgggaaaac cccttccatt ctcctttgac atactgtcat cagtctttca gtatggaaac 180
aggtgcttca caaaataccc tgcagacatg cctgactatt tcaagcaagc atttccagat 240
ggaatgtcat atgaaaggtc atttctattt gaggatggag cagttgctac agccagctgg 300
aaaattcgtc tcgaaggaaa ttgcttcatc cacaactcca tctttaatgg cgtaaacttt 360
cccgctgatg gacccgtaat ggaaaagaag acaattggct gggataagtc cttcgaaaaa 420
atgactgtgt ctaaagaggt gctaagaggt gatgtgacta tgtttcttat gctcgaagga 480
ggtggttctc acagatgcca gtttcactcc acttacaaaa cagagaagcc ggtcacactg 540
cccccgaatc atgtcgtaga acatcaaatt gtgaggaccg accttggcca aagtgcaaaa 600
ggctttacag tcaagctgga agcacatgct gcggctcatg ttaacccttt gaaggttaaa 660
catcaccatc accatcacta ataa 684

<210> SEQ ID NO 90
<211> LENGTH: 681
<212> TYPE: DNA
<213> ORGANISM: Agaricia fragilis

<400> SEQUENCE: 90
atgatgacta agctacacat ggaaggtact gttaacgggc acgcccttac aattgaaggc 60
aaaggaaaag gcgatcctta caatggagtg cagtctatga accttgacgt caaaggcggt 120
gcgcctttgc cgttctcttt cgatctcttg acgccagcat tcatgtacgg caacagagtg 180
ttcgcgaagt atccagaaga cataccagac tttttcaagc aggtgtttcc tgaagggtac 240
cactgggaaa gaagtattac ctttgaagat caggccgttt gtacggcaac cagccacata 300
aggctggacc agaaagagat gtgttttatc tatgacgtcc gttttcacgg tgtgaacttt 360
cccgccaatg gcccaatcat gcagaagaag atactgggat gggagccatc cactgagaaa 420
atgtatgcac gtgatggggt gctgaagggt gatgttaata tgactcttcg tgttgaagga 480
ggtggccatt accgagctga cttcagaact acttacaaag caaagaagcc agtcaacctg 540
ccaggctatc acttcataga ccaccgcatt gagattacca agcacagcaa agattacacc 600
aatgttgctt tgtatgaggc agcagttgct cgtcattctc cgctgcctaa ggttgctcat 660
caccatcacc atcactaata a 681

<210> SEQ ID NO 91
<211> LENGTH: 680
<212> TYPE: DNA
<213> ORGANISM: Agaricia fragilis

<400> SEQUENCE: 91
atgatgacta agctacacat ggaaggtact gttaacgggc acgcctttac aattgaaggc 60
aaaggaaaag gcgatcctta caatggagtg cagtctatga accttgacgt caaaggcggt 120
gcgcctttgc cgttctcttt cgatctcttg acgccagcat tcatgtacgg caacagagtg 180
ttcacgaagt atccagaaga cataccagac tttttcaagc aggtgtttcc tgaagggtac 240

-continued

```
cactgggaaa gaagtattac ctttgaagat caggccgttt gtacggcaac cagccacata    300

aggctggacc agaaagagat gtgttttatc tatgacgtcc gttttcacgg tgtgaacttt    360

cccgccaatg gcccaatcat gcagaagaag atactgggat gggagccatc cactgagaaa    420

atgtatgcac gtgatggggt gctgaagggt gatgttaata tgactcttcg tgttgaagga    480

ggtggccatt accgagctga cttcagaact acttacaaag caaagaagcc agtcaacctg    540

ccaggctatc acttcataga ccaccgcatt gagattacca agcacagcaa agattacacc    600

aatgttgctt tgtatgaggc agcagttgct cgtcattctc cgctgcctaa ggttgctcat    660

caccatcaca tcactaataa                                                680
```

```
<210> SEQ ID NO 92
<211> LENGTH: 681
<212> TYPE: DNA
<213> ORGANISM: Agaricia fragilis

<400> SEQUENCE: 92

atgatgacta agctacacat ggaaggtact gttaacgggc acgcctttac aattgaaggc     60

aaaggaaaag gcgatcctta caatggagtg cagtctatga accttgacgt caaaggcggt    120

gcgcctttgc cgttctcttt cgatctcttg acgccagcat tcatgtacgg caacagagtg    180

ttcacgaagt atccagaaga cataccagac tttttcaagc aggtgtttcc tgaagggtac    240

cactgggaaa gaagtattac ctttgaagat caggccgttt gtacggcaac cagccacata    300

aggctggacc agaaagagat gtgttttatc tatgacgtcc gttttcacgg tgtgaacttt    360

cccgccaatg gcccaatcat gcagaagaag atactgggat gggagccatc cactgagaaa    420

atgtatgcac gtgatggggt gctgaagggt gatgttaata tgactcttcg tgttgaagga    480

ggtggccatt accgagctga cttcagaact acttacaaag caaagaagcc agtcaacctg    540

ccaggctatc acttcataga ccaccgcatt gagattacca agcacagcaa agattacacc    600

aatgttgctt tgtatggggc agcagttgct cgtcattctc cgctgcctaa ggtttctcat    660

caccatcacc atcactaata a                                              681
```

```
<210> SEQ ID NO 93
<211> LENGTH: 678
<212> TYPE: DNA
<213> ORGANISM: Agaricia fragilis

<400> SEQUENCE: 93

atgactaagc tacacatgga aggtactgtt aacgggcacg cctttacaat tgaaggcaaa     60

ggaaaaggcg atccttacaa tggagtgcag tctatgaacc ttgacgtcaa aggcggtgcg    120

cctttgccgt tctctttcga tctcttgacg ccagcattca tgtacggcaa cagagtgttc    180

acgaagtatc cagaagacat accagacttt ttcaagcagg tgtttcctga agggtaccac    240

tgggaaagaa gtattacctt tgaagatcag gccgtttgta cggcaaccag ccacataagg    300

ctggaccaga aagagatgtg ttttatctat gacgtccgtt ttcacggtgt gaactttccc    360

gccaatggcc caatcatgca gaagaagata ctgggatggg agccatccac tgagaaaatg    420

tatgcacgtg atggggtgct gaagggtgat gttaatgtga ctcttcgtgt tgaaggaggt    480

ggccattacc gagctgactt cagaactact tacaaagcaa agaagccagt caacctgcca    540

ggctatcact tcatagacca ccgcattgag attaccaagc acagcaaaga ttacaccaat    600

gttgctttgt atgaggcagc agttgctcgt cattctccgc tgcctaaggt tgctcatcac    660

catcaccatc actaataa                                                  678
```

<210> SEQ ID NO 94
<211> LENGTH: 681
<212> TYPE: DNA
<213> ORGANISM: Agaricia fragilis

<400> SEQUENCE: 94

```
atgatgacta agctacacat ggaaggtact gttaacgggc acgcctttac aattgaaggc     60
aaaggagagg gcgatcctta caatggagtg cagtctatga accttgacgt caaaggcggt    120
gcgcctttgc cgttctcttt cgatctcttg acgccagcat tcatgtacgg caacagagtg    180
ttcacgaagt atccagaaga cataccagac tttttcaagc aggtgtttcc tgaagggtac    240
cactgggaaa gaagtattac ctttgaagat caggccgttt gtacggctac cagccacata    300
aggctggacc agaaagagat gtgttttatc tatgacgtcc gttttcacgg tgtgaacttt    360
cccgccaatg gcccaatcat gcagaagaag atactgggat gggagccatc cactgagaaa    420
atgtatgcac gtgatggggt gctgaagggt gatgttaata tgactcttcg tgttgaagga    480
ggtggccatt accgagctga cttcagaact acttacaaag caaagaagcc agtcaacctg    540
ccaggctatc acttcataga ccaccgcatt gagattacca agcacagcaa agattacacc    600
aatgttgctt tgtatggggc agcagttgct cgtcattctc cgctgcctaa ggttgctcat    660
caccatcacc atcactaata a                                              681
```

<210> SEQ ID NO 95
<211> LENGTH: 681
<212> TYPE: DNA
<213> ORGANISM: Agaricia fragilis

<400> SEQUENCE: 95

```
atgatgacta agctacacat ggaaggtact gttaacgggc acgcctttac aattgaaggc     60
aaaggaaaag gcgatcctta caatggagtg cagtctatga accttgacgt caaaggcggt    120
gcgcctttgc cgttctcttt cgatctcttg acgccagcat tcatgtacgg caacagagtg    180
ttcacgaagt atccagaaga cataccagac tttttcaagc aggtgtttcc tgaagggtac    240
cactgggaaa gaagtattac ctttgaagat caggccgttt gtacggcaac cagccacata    300
aggctggacc agaaagagat gtgttttatc tatgacgtcc gttttcacgg tgtgaacttt    360
cccgccaatg gcccaatcat gcagaagaag atactgggat gggagccatc cactgagaaa    420
atgtatgcac gtgatggggt gctgaagggt gatgttaata tgactcttcg tgttgaagga    480
ggtggccatt accgagctga cttcagaact acttacaaag caaagaagcc agtcaacctg    540
ccaggctatc acttcataga ccaccgcatt gagattacca agcacagcaa agattacacc    600
aatgttgctt tgtatgaggc agcagttgct cgtcattctc cgctgcctaa ggttgctcat    660
caccatcacc atcactaata a                                              681
```

<210> SEQ ID NO 96
<211> LENGTH: 681
<212> TYPE: DNA
<213> ORGANISM: Agaricia fragilis

<400> SEQUENCE: 96

```
atgatgacta agctacacat ggaaggtact gttaacgggc acgcctttac aattgaaggc     60
aaaggaaaag gcgatcctta caatggagtg cagtctatga accttgacgt caaaggcggt    120
gcgcctttgc cgttctcttt cgatctcttg acgccagcat tcatgtacgg caacagagtg    180
```

-continued

```
ttcacgaagt atccagaaga cataccagac tttttcaagc aggtgtttcc tgaagggtac    240

cactgggaaa gaagtattac ctttgaagat caggccgttt gtacggcaac cagccacata    300

aggctggacc agaaagagat gtgttttatc tatgacgtcc gttttcacgg tgtgaacttt    360

cccgccaatg gcccaatcat gcagaagaag atactgggat gggagccatc cactgagaaa    420

atgtatgcac gtgatggggt gctgaagggt gatgttaata cgactcttcg tgttgaagga    480

ggtggccatt accgagctga cttcagaact acttacaaag caaagaagcc agtcaacctg    540

ccaggctatc acttcataga ccaccgcatt gagattacca agcacagcaa agattacacc    600

aatgttgctt tgtatgaggc agcagttgct cgtcattctc cgctgcctaa ggttgctcat    660

caccatcacc atcactaata a                                               681
```